US012799105B2

(12) United States Patent
Banoglu et al.

(10) Patent No.: US 12,799,105 B2
(45) Date of Patent: Nov. 17, 2026

(54) ISOXAZOLE DERIVATIVES TARGETING TACC3 AS ANTICANCER AGENTS

(71) Applicants: Coiled Therapeutics, Inc., Edison, NJ (US); OncoCube Therapeutics LLC, Wilmington, DE (US)

(72) Inventors: Erden Banoglu, Ankara (TR); Burcu Caliskan, Ankara (TR); Ozgur Sahin, Charleston, SC (US); Deniz Lengerli, Ankara (TR); Ozge Akbulut, Ankara (TR); Chaemin Lim, New York, NY (US); Emmanuel Cruz, West Long Branch, NJ (US); Sridhar Vempati, Edison, NJ (US); Kubra Ibis, Ankara (TR)

(73) Assignees: OncoCube Therapeutics LLC, Wilmington, DE (US); Coiled Therapeutics, Inc., Edison, NJ (US)

( * ) Notice: Subject to any disclaimer, the term of this patent is extended or adjusted under 35 U.S.C. 154(b) by 926 days.

(21) Appl. No.: 17/776,767

(22) PCT Filed: Nov. 13, 2020

(86) PCT No.: PCT/US2020/060588

§ 371 (c)(1),
(2) Date: May 13, 2022

(87) PCT Pub. No.: WO2021/097352

PCT Pub. Date: May 20, 2021

(65) Prior Publication Data

US 2023/0027854 A1 Jan. 26, 2023

(30) Foreign Application Priority Data

Nov. 14, 2019 (EP) .................................... 19209120

(51) Int. Cl.
*C07D 413/14* (2006.01)
*A61K 9/00* (2006.01)
(Continued)

(52) U.S. Cl.
CPC .......... *C07D 413/14* (2013.01); *A61K 9/0053* (2013.01); *A61K 31/506* (2013.01);
(Continued)

(58) Field of Classification Search
CPC C07D 413/14; C07D 417/14; C07D 491/107; C07D 491/08; A61K 31/506;
(Continued)

(56) References Cited

U.S. PATENT DOCUMENTS

| | | | | |
|---|---|---|---|---|
| 9,630,953 B2 | 4/2017 | Yao et al. | | |
| 11,622,966 B2 * | 4/2023 | Banoglu | ................ | A61P 35/00 514/235.8 |

(Continued)

FOREIGN PATENT DOCUMENTS

| | | | |
|---|---|---|---|
| CN | 107089968 A | 8/2017 | |
| EP | 2857392 A1 | 4/2015 | |

(Continued)

OTHER PUBLICATIONS

CAS Registery No. 2322029-91-2 (May 31, 2019). (Year: 2019).*

(Continued)

*Primary Examiner* — Clinton A Brooks
*Assistant Examiner* — Izabela Schmidt
(74) *Attorney, Agent, or Firm* — Foley Hoag LLP; Lucas P. Watkins; Alexander J. Chatterley

(57) ABSTRACT

In one aspect, the present disclosure relates to compounds and compositions capable of inhibiting TACC3. In another aspect, the present disclosure relates to methods of treating TACC3 mediated diseases and disorders.

11 Claims, 29 Drawing Sheets

(51) Int. Cl.
*A61K 31/506* (2006.01)
*A61K 31/5377* (2006.01)
*A61K 31/541* (2006.01)
*A61P 1/00* (2006.01)
*A61P 13/08* (2006.01)
*A61P 35/00* (2006.01)
*C07D 417/08* (2006.01)
*C07D 417/14* (2006.01)
*C07D 491/08* (2006.01)
*C07D 491/107* (2006.01)

(52) U.S. Cl.
CPC ........ *A61K 31/5377* (2013.01); *A61K 31/541* (2013.01); *A61P 1/00* (2018.01); *A61P 13/08* (2018.01); *A61P 35/00* (2018.01); *C07D 417/14* (2013.01); *C07D 491/08* (2013.01); *C07D 491/107* (2013.01)

(58) Field of Classification Search
CPC .............. A61K 31/5377; A61K 31/541; A61K 9/0053; A61P 1/00; A61P 13/08; A61P 35/00
See application file for complete search history.

(56) References Cited

U.S. PATENT DOCUMENTS

| | | | |
|---|---|---|---|
| 2006/0069110 | A1 | 3/2006 | Andersen et al. |
| 2012/0225880 | A1 | 9/2012 | Jiaang et al. |
| 2016/0332989 | A1 | 11/2016 | Wu et al. |
| 2019/0337926 | A1 | 11/2019 | Hashizume et al. |
| 2021/0220369 | A1 | 7/2021 | Banoglu et al. |
| 2023/0183520 | A1 | 6/2023 | Fujita et al. |
| 2024/0156813 | A1 | 5/2024 | Lim et al. |
| 2024/0374590 | A1 | 11/2024 | Lim et al. |

FOREIGN PATENT DOCUMENTS

| | | | | |
|---|---|---|---|---|
| JP | 2016/065869 | A | 4/2016 | |
| WO | WO-03018022 | A1 * | 3/2003 | ........... C07D 413/14 |
| WO | WO-2006/037117 | A1 | 4/2006 | |
| WO | WO-2007/026251 | A2 | 3/2007 | |
| WO | WO-2008/005538 | A2 | 1/2008 | |
| WO | WO-2011/120026 | A1 | 9/2011 | |
| WO | WO-2012/117059 | A1 | 9/2012 | |
| WO | WO-2013/102431 | A1 | 7/2013 | |
| WO | WO-2015/082583 | A1 | 6/2015 | |
| WO | WO-2016/146220 | A1 | 9/2016 | |
| WO | WO-2016/173557 | A1 | 11/2016 | |
| WO | WO-2016/196776 | A2 | 12/2016 | |
| WO | WO-2017/136315 | A1 | 8/2017 | |
| WO | WO-2018/002217 | A1 | 1/2018 | |
| WO | WO-2018/045957 | A1 | 3/2018 | |
| WO | WO-2018/231910 | A1 | 12/2018 | |
| WO | WO-2019/101843 | A1 | 5/2019 | |
| WO | WO-2019/161224 | A1 | 8/2019 | |
| WO | WO-2019/177374 | A1 | 9/2019 | |
| WO | WO-2020/018039 | A2 | 1/2020 | |
| WO | WO-2021/030623 | A1 | 2/2021 | |
| WO | WO-2021/097352 | A1 | 5/2021 | |
| WO | WO-2022/221194 | A1 | 10/2022 | |
| WO | WO-2023/183520 | A1 | 9/2023 | |
| WO | WO-2025/072722 | A1 | 4/2025 | |

OTHER PUBLICATIONS https://aurorafinechemicals.com/ (printed Apr. 17, 2025) (Year: 2025). (Year: 2025).*

Costa R., Carneiro B. A., Taxter T., Tavora F. A., Kalyan A., Pai S. A., Chae Y., Giles F. J. FGFR3-TACC3 fusion in solid tumors: mini review. Oncotarget. 2016; 7: 55924-55938. (Year: 2016).*

Lengerli et al., "Isoxazole-pyrimidine derivatives as TACC3 inhibitors: A novel modality to targeted cancer therapy," Bioorganic Chemistry 156 (2025): 108204.

Supplementary Partial European Search Report for EP Application No. 22788722.1 dated Feb. 18, 2025.

U.S. Appl. No. 17/058,982, Issued.

U.S. Appl. No. 18/286,469, Pending.

U.S. Appl. No. 18/389,078, Pending.

Dever et al., "CRISPR/Cas9 β-globin gene targeting in human haematopoietic stem cells." Nature 539 (2016): 384-389.

Xu et al., "Quantitation of physiological and biochemical barriers to siRNA liver delivery via lipid nanoparticle platform." Molecular Pharmaceutics 11.5 (2014): 1424-1434.

Yin et al., "Therapeutic genome editing by combined viral and non-viral delivery of CRISPR system components in vivo." Nature Biotechnology 34 (2016): 328-333.

Zhang et al., "The development of an in vitro assay to screen lipid based nanoparticles for siRNA delivery." *Journal of controlled release* 174 (2014): 7-14.

Chu-Farseeva et al., "Design and synthesis of potent dual inhibitors of JAK2 and HDAC based on fusing the pharmacophores of XL019 and vorinostat," European Journal of Medicinal Chemistry 158 (2018): 593-619.

International Search Report and Written Opinion for International Application No. PCT/US24/48928 dated Dec. 22, 2024.

U.S. Appl. No. 18/389,078, Issued.

U.S. Appl. No. 18/849,309, Pending.

CAS Registry No. 499142-07-3 CA Index Name: 5-Pryimidinecarboxylic acid, 2-(methylthio)-4-[(3-phenyl-5-isoxazolyl)amino]-,ethyl ester Entered STN: Mar. 14, 2003.

Extended European Search Report for EP Application No. 20888312.4 dated Nov. 28, 2023.

ClinicalTrials, NCT06136884, "A First-In-Human, Phase 1 Study Evaluating Oral TACC3 PPI Inhibitor, AO-252, in Advanced Solid Tumors", National Institute of Health, 13 pages (Record updated Nov. 18, 2023).

Lengerli, "Studies on the Synthesis and Investigation of Their Mechanisms of Action of Anti-Cancer-Active 2,4-Diamineprimidine Derivative Compounds" Gazi University, 362 Pages (2021).

Saacti et al., "Targeting TACC3 represents a novel vulnerability in highly aggressive breast cancers with centrosome amplification" CDD press, 15 pages (2023).

Chu-Farseeva et al., "Design and synthesis of potent dual inhibitors of JAK2 and HDAC based on fusing the pharmacophores of XL019 and vorinostat", *European journal of medicinal chemistry* 158: 593-619 (2018).

International Search Report and Written Opinion for International Application No. PCT/US2023/016132 dated May 15, 2023.

Banoglu et al., "Inhibiting Transforming Acidic Coiled-Coil Protein 3(TACC3): A New Modality for Targeted Cancer Therapy", Medicinal Chemistry Frontiers, Chicago, May 12-15, 2025.

Gedik et al., "Targeting TACC3 Inhibits Metastasis in Breast Cancer with Centrosome Amplification", Medical University of South Carolina, 2025.

Supplementary European Search Report for EP Application No. 22788722.1 dated Jun. 30, 2025.

Vempati et al., "Novel TACC3 protein-protein interaction inhibitor, AO-252, shows potent activity in prostate, gastric cancers, and triple negative breast cancer with brain metastasis", A2A Pharma, New York, 2025.

Akbulut et al., "A Highly Potent TACC3 Inhibitor as a Novel Anticancer Drug Candidate," Molecular Cancer Therapeutics, 19(6): 1243-1254 (2020).

Akbulut et al., "A novel TACC3 inhibitor as an anti-cancer agent in breast cancer [abstract]," Cancer Research, 79(13): 4 pages (2019).

Akbulut et al., "A novel TACC3 inhibitor as an anti-cancer agent in breast cancer [abstract]," European Journal of Cancer, 103(S1): e71 Abstract 200(PB-051)(2018).

Campo et al., "Inhibition of TACC3 by a small molecule inhibitor in breast cancer," Biochemical and Biophysical Research Communications, 498(4): 1085-1092 (2018).

(56) References Cited

OTHER PUBLICATIONS

CAS Registry No. 2322029-91-2; CA Index Name: 4-Pyrimidinamine, 6-ethyl-5-fluoro-N-[3-(2-thienyl)-5-isoxazolyl]-; Entered STN: May 31, 2019.
CAS Registry No. 2326659-25-8; CA Index Name: 4-Pyrimidinamine, N-[3-(2-thienyl)-5-isoxazolyl]-6-(trifluoromethyl)-; Entered STN: Jun. 9, 2019.
CAS Registry No. 2328417-44-1; CA Index Name: 4-Pyrimidinamine, 2-cyclopropyl-6-methyl-N-[3-(2-thienyl)-5-isoxazolyl]-; Entered STN: Jun. 11, 2019.
CAS Registry No. 2329636-00-0; CA Index Name: 4-Pyrimidinamine, 6-ethyl-N-[3-(2-thienyl)-5-isoxazolyl]-; Entered STN: Jun. 11, 2019.
CAS Registry No. 2329672-37-7; CA Index Name: 4-Pyrimidinamine, 2-methyl-N-[3-(2-thienyl)-5-isoxazolyl]-6-(trifluoromethyl)-; Entered STN: Jun. 11, 2019.
CAS Registry No. 2329697-20-1; CA Index Name: 2-Pyridinecarboxylic acid, 4-[3-(2-thienyl)-5-isoxazolyl]amino]-, methyl ester; Entered STN: Jun. 11, 2019.
CAS Registry No. 2329701-76-8; CA Index Name: 4-Pyrimidinamine, 5,6-dimethyl-N-[3-(2-thienyl)-5-isoxazolyl]-; Entered STN: Jun. 11, 2019.
CAS Registry No. 2329961-45-5; CA Index Name: 4-Pyrimidinamine, 2-(1-methylethyl)-N-[3-(2-thienyl)-5-isoxazolyl]-; Entered STN: Jun. 12, 2019.
CAS Registry No. 2330400-57-0; CA Index Name: 4-Pyrimidinamine, 2-methyl-N-[3-(2-thienyl)-5-isoxazolyl]-; Entered STN: Jun. 12, 2019.
CAS Registry No. 2330488-91-8; CA Index Name: 4-Pyrimidinamine, 2,6-dimethyl-N-[3-(2-thienyl)-5-isoxazolyl]-; Entered STN: Jun. 12, 2019.
CAS Registry No. 2330625-68-6; CA Index Name: 4-Pyrimidinamine, 6-methyl-N-[3-(2-thienyl)-5-isoxazolyl]-; Entered STN: Jun. 12, 2019.
Extended European Search Report for EP Application No. 19209120.5 dated Mar. 17, 2020.
Extended European Search Report for EP Application No. EP 19837587 dated Mar. 9, 2022.
International Search Report and Written Opinion for International Application No. PCT/TR2019/050164 dated Feb. 21, 2020.
International Search Report and Written Opinion for International Application No. PCT/TR2019/050951 dated Aug. 14, 2020.
International Search Report and Written Opinion for International Application No. PCT/US2020/060588 dated Mar. 4, 20201.
Wurdak et al., "A small molecule accelerates neuronal differentiation in the adult rat," PNAS, 107(38): 16542-16547 (2010).
Yao et al. "A small compound targeting TACC3 revealed its different spatiotemporal contributions for spindle assembly in cancer cells," Oncogene, 33(33): 4242-4252 (2013).
Ha et al., "TACC3 deregulates the DNA damage response and confers sensitivity to radiation and PARP inhibition", Oncogene, 34: 1667-1678, (2015).
Ha et al., "Transforming acidic coiled-coil proteins (TACCs) in human cancer", Cancer Letters, 336(1): 24-33, (2013).
Lengerli et al., "Studies on the Synthesis and Anticancer Potential of Novel 2,4-Diaminopyrimidine Derivatives," EFMC-YMSC Abstract: 1 page (Sep. 8, 2022).
Lin et al., "Discovery and evaluation of 3-phenyl-1 H-5-pyrazolylamine-based derivatives as potent, selective and efficacious inhibitors of FMS-like tyrosine kinase-3 (FLT3). Bioorganic & medicinal chemistry", 19(14): 4173-4182, (2011).
Turk et al., "From cancer to pain target by automated selectivity inversion of a clinical candidate", Journal of Medicinal Chemistry, 61(11): 4851-4859, (2018).
Lengerli, D., Akbulut O., Caliskan, B., Sahin, O., Banoglu, E., *Studies on the Synthesis and Anticancer Potential of Novel 2,4-Diaminopyrimidine Derivatives.* The 9th Young Medicinal Chemist Symposium (EFMC-YMCS 2022), Nice—France, Sep. 8-9, 2022 (International Congress, Oral Presentation). Scientific Programme.
Lengerli, D., Akbulut, Ö., Çalişkan, B., Şahin, Ö., Banoğlu, E., *TACC3 İnhibitörü Yeni 2,4-Diaminopirimidin Türevlerinin Sentezi, Anti-Kanser Etki Potansiyelleri ve İlaç Benzeri Özelliklerinin Değerlendirilmesi Üzerine Çalişmalar.* VI. Ulusal Farmasötik Kimya Kongresi (UMFKK2022), Istanbul-Türkiye, Aug. 26-29, 2022 (National Congress, Oral Presentation).
Turkish Examination Report for TR application No. 2018/07464 dated Jun. 28, 2020.
Turkish Search Report for TR application No. 2018/07464 dated Feb. 21, 2020.

* cited by examiner

FIG. 2

| Parameter | n | HR | *P* |
|---|---|---|---|
| TACC3 expression | | 2.727 | 7.65E-09 |
| Low | 476 | | |
| High | 476 | | |
| Tumor Grade | | 1.079 | 0.44 |
| 1 | 102 | | |
| 2 | 353 | | |
| 3 | 455 | | |
| Tumor Stage | | 1.038 | 0.594 |
| 0 | 200 | | |
| 1 | 186 | | |
| 2 | 299 | | |
| 3 | 36 | | |
| 4 | 5 | | |
| ER Status | | 0.904 | 0.57 |
| Negative | 235 | | |
| Positive | 717 | | |
| Her2 Status | | 1.14 | 0.499 |
| Negative | 854 | | |
| Positive | 98 | | |
| PR Status | | 0.953 | 0.779 |
| Negative | 455 | | |
| Positive | 497 | | |

Abbreviations: PR, progesterone receptor; ER, estrogen receptor; n, number of patients; HR, hazard ratio

B-1

B-2

| Group | Days after treatment | | | | | | | |
|---|---|---|---|---|---|---|---|---|
| | 0 | 1 | 2 | 3 | 4 | 5 | 6 | 7 |
| 100 mg/kg Compound 5 | 19.9 | 17.8 | 18.4 | 18.9 | 18.9 | 19.4 | 19.2 | 19.1 |
| | 19.6 | 20.4 | 19 | 19.4 | 20.6 | 20.6 | 21 | 21 |
| | 18.8 | 18.9 | 16.8 | 17.8 | 18.5 | 17.7 | 18.3 | 18 |
| | 17.3 | 17.4 | 16.2 | 16.3 | 17 | 16.5 | 16.7 | 16.8 |

| Group | Days after treatment | | | |
|---|---|---|---|---|
| | 0 | 1 | 2 | 3 |
| Vehicle | 26.3 | 26.9 | | |
| | 23.7 | 23.4 | | |
| | 22.5 | 21.8 | 21.7 | |
| 500 mg/kg Compound 5 | 26 | 23.2 | | |
| | 24.9 | 21.1 | 20.9 | 21.5 |
| | 23.6 | 21.9 | 21.9 | 21.9 |

FIG. 14

| | | | | |
|---|---|---|---|---|
| **Molecular Weight (g/mol)** | 353.38 | | | |
| **Solubility at pH 7.4 (μM)**[a] | < 1 | | | |
| **LogD at pH 7.4**[b] | 2.31 | | | |
| **Human PPB (%bound)**[c] | 98.87 | | | |
| **$T_{1/2}$ (min)**[d] | $5_{(MLM)}$ | | $12_{(HLM)}$ | |
| **$Cl_{int}$ (μL/min/mg protein)**[e] | $329.2_{(MLM)}$ | | $117.5_{(HLM)}$ | |
| **CYP ($IC_{50}$ μM)**[f] | *CYP2C9* | *CYP2D6* | *CYP3A4* | *CYP3A4* |
| | 2.63 ± 0.19 | 18.46 ± 0.23 | 30.04 ± 4.24 | 8.59 ± 1.68 |
| **Caco-2 $P_{app}$ (nm/s)**[g] | 190.60 ± 61.82 $_{(A\rightarrow B)}$ | | 241.03 ± 8.18 $_{(B\rightarrow A)}$ | |

ISOXAZOLE DERIVATIVES TARGETING TACC3 AS ANTICANCER AGENTS

RELATED APPLICATIONS

This application is the § 371 National Stage of PCT/US2020/060588, filed Nov. 13, 2020, which claims the right of priority to EP Patent Application No. 19209120.5, filed on Nov. 14, 2019; the contents of each of the aforementioned applications are hereby incorporated by reference in their entirety.

TECHNICAL FIELD

The present disclosure relates to substituted compounds of Formula (I), useful as transforming acidic coiled-coil protein 3 (TACC3) inhibitors, pharmaceutical compositions of such compounds, methods of preparation and use thereof. More particularly, TACC3 inhibitors are useful for treating or ameliorating TACC3-mediated cancers including breast, leukemia, lung, colon, melanoma, prostate, ovarian, renal and CNS cancer.

(I)

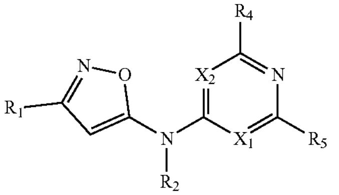

BACKGROUND OF THE DISCLOSURE

Cancer is a complex disease characterized by uncontrolled cell division. Among cancer types, breast cancer is the most common cancer among women and is one of the main reasons of cancer deaths. With the understanding of tumor biology, targeted medical therapies have continuously been developed to increase the patient survival rate.

Although the Food and Drug Administration (FDA) has approved approximately two dozen drugs to be used for the treatment of breast cancer, there is still half a million-breast cancer death all round the world each year. In particular, considering the side effects of currently available chemotherapy agents, the development of targeted therapies causing less toxicity has been a major focus in recent years. Since cancer is characterized as abnormal and uncontrollable cell growth with the potential to invade or spread to the other parts of the body or a malignant tumor, drugs or substances that target and inhibit the function of specific macromolecules responsible for the proliferation and survival of tumor cells are used in breast cancer-targeted therapies.

Since microtubule re-organization is an important step during cell division, drugs that interfere with this process have been a major focus of cancer research. Anti-mitotic drugs disrupt the polymerization dynamics of microtubules by activating the spindle assembly check point (SAC), which prevents the transition from metaphase to anaphase. As a result, cells stop division, and these mitotically arrested cells eventually die. A continuous investigation of the mechanism of mitotic events may lead to new target protein candidates and/or pathways, which are very important for providing more effective therapeutic options for cancer patients. Anti-microtubule agents, such as vinca alkaloids, maytansinoids and taxanes are examples of such drugs that are widely used as chemotherapeutic agents for a variety of tumors (Marzo & Naval, 2013). However, a significant concern about these drugs is the drug toxicity to non-tumorigenic cells resulting in serious side effects.

Drug resistance is also another major problem leaving patients' response to these drugs highly unpredictable (Gascoigne & Taylor, 2009). To overcome these problems and improve chemotherapy response, anti-mitotic, cancer specific therapies targeting mitosis-specific kinases and microtubule-motor proteins were identified (Dominguez-Brauer et al., 2015). Importantly, since phosphorylation is a critical step in cell cycle regulation and spindle assembly, kinases having role in these processes have been studied for a long time as potential targets. Among these, specific inhibitors against cyclin-dependent kinases (CDKs), Aurora kinases and Polo-like kinases (PLKs) have been developed and clinically tested (Sanchez-Martinez, Gelbert, Lallena, & de Dios, 2015; Strebhardt & Ullrich, 2006; Tang et al., 2017). Compared to anti-microtubule agents, none of these anti-mitotic drugs demonstrated a spectacular clinical outcome despite their low toxicity profile, leading to limited clinical efficiency (Chan, Koh, & Li, 2012). Thus, alternative target molecules that selectively and effectively target dividing cancer cells remain to be elucidated and developed.

TACC3, one of the TACC members, is a non-kinase microtubule binding protein and plays a key role in centrosome regulation and ensures microtubule stability (Singh, Thomas, Gireesh, & Manna, 2014). This TACC3 gene also has an important role in the nucleation of TACC3 centrosomal microtubules. Its elevated levels are observed in many cancer types including prostate cancer, hepatocellular carcinoma, non-small cell lung cancer and breast cancer an so on. Accordingly, knockdown of TACC3 suppresses tumorigenesis and cell growth in renal cell carcinoma (RCC) (Guo & Liu, 2018). Disruption of TACC3 function also causes a range of different cellular outcomes including multi-polar spindle formation leading to mitotic arrest (Yao et al., 2012), chromosome misalignment resulting in caspase-dependent apoptosis (Schneider et al., 2007) and, in some cases, senescence (Schmidt et al., 2010). These studies show that TACC3 is a critical molecule enrolled in spindle assembly of cancer cells, which makes it an important and potential target for cancer targeted therapy.

KHS101, a small molecule TACC3 inhibitor, was first identified to promote neuronal differentiation in rats (Wurdak et al., 2010). Although tumor growth of glioblastoma (GBM) xenografts were suppressed through KHS101 treatment (Polson et al., 2018), it requires to be pharmacologically optimized in order to be translated into clinics due to low systemic stability and high working doses (Wurdak et al., 2010). Another TACC3 inhibitor, SPL-B, has been shown to inhibit the centrosome microtubule nucleation in ovarian cancer cells and suppress tumor growth in ovarian cancer xenografts (Yao et al., 2014). In conclusion; currently available two TACC3 inhibitors, KHS101 and SPL-B, were shown to reduce tumor growth in glioblastoma and ovarian cancer xenografts, respectively. However, none of these inhibitors has yet reached clinical phases due to low potency or low systemic stability.

All of the above evidence supports a key role of TACC3 in cancer, and inhibition of TACC3 function would be effective for the treatment or amelioration of a variety of human cancers. Furthermore, there still remains a need for TACC3 inhibitor compounds that have pharmacokinetic and pharmacodynamic properties suitable for use as human pharmaceuticals.

BRIEF DESCRIPTION OF THE DISCLOSURE

In one aspect, the present disclosure relates to compounds of Formula (I):

(I)

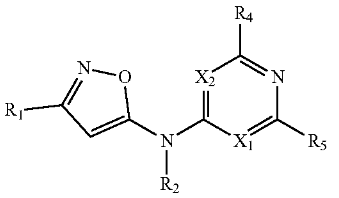

or a pharmaceutically acceptable salt thereof, wherein $X_1$ is N or $CR_6$;

$X_2$ is N or $CR_3$;

$R_1$ is aryl or heteroaryl;

$R_2$ is H or alkyl;

$R_3$, $R_4$ and $R_6$ are each independently H, alkyl, alkenyl, alkynyl, halo, hydroxyl, carboxyl, acyl, acetyl, ester, thioester, alkoxy, phosphoryl, amino, amide, cyano, nitro, azido, alkylthio, alkenyl, alkynyl, cycloalkyl, or sulfonamide; and $R_5$ is heterocyclyl, alkyl, or amino.

In another aspect, the present disclosure relates to methods of treating TACC3 mediated disesas and disorders with the compounds disclosed herein. In certain embodiments, the TACC3 mediated disease or disorder is cancer.

In one aspect, an objective of the present disclosure is to reduce undesirable side effects by using smaller doses of TACC3 inhibitor with high potency as a mitotic blocker than specific inhibitors available in the cancer therapy.

As an example to all compounds, Compound 5 showed a superior anti-proliferative effect to known TACC3 inhibitors in different breast cancer cell lines with different subtypes while it has minor effects on normal breast cell line. In addition to breast cancer cells, Compound 5 demonstrated highly effective cytotoxicity (~90% have less than 1 μM $GI_{50}$ value) against multiple cancer types including colon, melanoma, lung, central nervous system, ovarian, leukemia, renal and prostate cancer cell lines in the NCI-60 panel. Moreover, Compound 5 showed a remarkable anti-cancer effect on FGFR3-TACC3 fusion protein harboring cells, whose activity correlated with TACC3 levels of these cells. Compound 5 also decreased ERK1/2 phosphorylation, which is a marker for activated FGFR signaling, along with a strong induction of mitotic arrest and apoptosis.

Furthermore, Compound 5 was found to induce mitotic arrest, apoptosis and DNA damage at lower doses compared to other two TACC3 inhibitors. It also induced aberrant spindle formations in a dose-dependent manner. Significantly, oral administration of Compound 5 suppressed tumor growth in both immunodeficient and immunocompetent mouse models of breast cancer. Compound 5 also impaired metastatic outgrowth and significantly improved the overall survival of mice harboring highly aggressive breast cancer metastases. Similar to breast cancer tumor models, Compound 5 significantly suppressed tumor growth of colon carcinoma xenografts and immunocompetent syngeneic models. Therefore, the present disclosure provides a novel TACC3 inhibitor with high potency as a mitotic blocker for the treatment of both primary and metastatic breast and potentially other cancers.

In certain aspects, the present disclosure (i) provides a compound selected from a group represented by the general formula I as a TACC3 inhibitor, (ii) provides a compound selected from a group represented by the general formula I as an anticancer agent, which are responsive to TACC3 inhibition, (iii) provides a comprehensive analysis of compound 5 as an example to all compounds on breast cancer cell lines, (iv) reveals that this compound demonstrates superior effects on various cellular processes, such as mitotic arrest, DNA damage and apoptosis to other available TACC3 inhibitors, (v) demonstrates in vivo anti-tumor effectiveness of compound 5 with no observable toxicity when given orally in breast cancer and colon cancer animal models, and (vi) shows its capacity to impair metastatic growth and to improve overall survival of metastases-bearing mice suggesting that it can be used as a mitotic blocker for the treatment for breast and other cancers that respond to TACC3 inhibition.

BRIEF DESCRIPTION OF THE DRAWINGS

FIG. 1 shows that TACC3 is upregulated in several different cancer types, and its high level is associated with worse overall survival. FIG. 1**B are plots that show that the effect of TACC3 level on overall survival of breast (B-1) and gastric (B-2) cancer, relapse-free survival of lung cancer (B-3) and disease-free survival of prostate (B-4) cancer patients retrieved from METABRIC, KM Plotter databases, GSE31210 and TCGA datasets, respectively. Log-rank test was used for statistical analyses.

FIG. 2: shows multivariate analysis performed in METABRIC patients by selecting TACC3 level, tumor grade, tumor stage, ER, PR and HER2 status as co-variates. TACC3 expression is separated based on $25^{th}$ percentiles.

FIG. 3: Generally, FIG. 3 shows that TACC3 inhibition induces mitotic arrest, apoptosis and DNA damage.

FIG. 4: Generally, FIG. 4 shows that compound 5, a novel TACC3 inhibitor, binds to TACC3.

FIG. 5: Generally, FIG. 5 shows that compound 5 is more potent than currently available TACC3 inhibitors, SPL-B and KHS101.

FIG. 6: Generally, FIG. 6 shows depicts that compound 5 shows remarkable anti-cancer activity in FGFR3-TACC3 fusion protein harboring cell lines and in NCI-60 cancer cell lines.

FIG. 7: Generally, FIG. 7 shows that TACC3 level is critical for compound 5 response.

FIG. 8: Generally, FIG. 8 shows that compound 5 impairs tumor growth significantly more than SPL-B does.

FIG. 9: Generally, FIG. 9 shows that different doses and administration routes of compound 5 inhibits tumor growth in in vivo JIMT-1 xenografts without affecting mouse body weight.

FIG. 10: Generally, FIG. 10 shows that compound 5 significantly impairs tumor growth and improves survival in immunocompetent mice.

FIG. 11 shows that targeting TACC3 with compound 5 significantly impairs tumor growth in colorectal carcinoma mouse models. FIG. 11**B shows the percent body weight changes of HCT-116 and CT-26 xenografts following treatment.

FIG. 12: Generally, FIG. 12 shows the effects of TACC3 targeting with compound 5 on metastatic outgrowth in 4T1.luc2 model.

FIG. 13: Generally, FIG. 113 shows the effects of high dose compound 5 on mouse body weight and internal organs.

FIG. 14: shows a summary of drug specific physico-chemical properties of compound 5. [a]Kinetic solubility in sodium phosphate buffer at pH 7.4 at 25° C. after 2 h (Buttar et al., 2010). [b]Log D: distribution coefficient in octanol/sodium phosphate buffer (50 mM, pH 7.4) (Unger et al., 1978). [c]PPB: plasma protein binding assessed by equilibrium dialysis in human at 37° C. (Buttar et al., 2010). [d]T1/2: half-life in mouse and human liver microsomes (MLM and HLM respectively) (Kalvass et al., 2001). ° Clint: intrinsic clearance in MLM and HLM (Kalvass et al., 2001). [f]CYP: cytochrome P450 isozymes inhibition by compound 5 evaluated in HLM (Bourrie et al., 1996). [g]Papp: apperant permeability coefficients in Caco-2 cell monolayer (Camenisch et al., 1998).

DETAILED DESCRIPTION OF THE DISCLOSURE

Elevated TACC3 levels are observed in many different cancer types, which makes it highly attractive target for cancer therapy. TACC3 has important roles in regulating microtubule and centrosome and maintaining spindle stability (Schneider et al., 2007; Thakur et al., 2013).

Figure 1A:
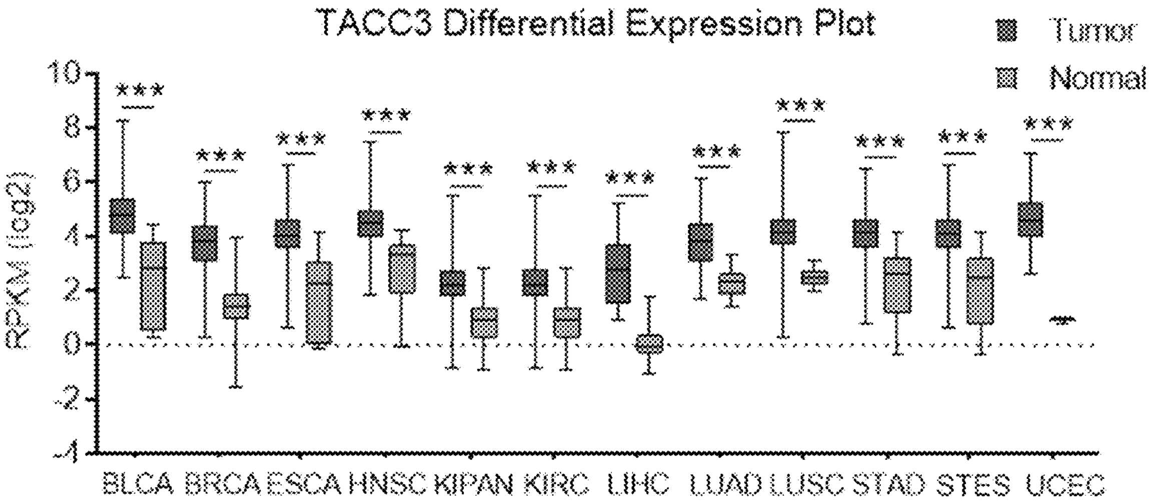
FIG. 1A are differential mRNA expression plots of TACC3 between tumor and normal tissues of TCGA patients represented as Reads Per Kilobase Million (RPKM) (log 2) values. *: $p<0.001$. (BLCA: Bladder Urothelial Carcinoma; BRCA: Breast Invasive Carcinoma; ESCA: Esophageal Carcinoma; HNSC: Head and Neck Squamous Cell Carcinoma; KIPAN: Pan Kidney Cohort (KICH+KIRC+KIRP); KIRC: Kidney Renal Clear Cell Carcinoma; LIHC: Liver Hepatocellular Carcinoma; LUAD: Lung Adenocarcinoma; LUSC: Lung Squamus Cell Carcinoma; STAD: Stomach Adenocarcinoma; STES: Stomach and Esophageal Carcinoma; UCEC: Uterine Corpus Endometrial Carcinoma).
Figure 1B:
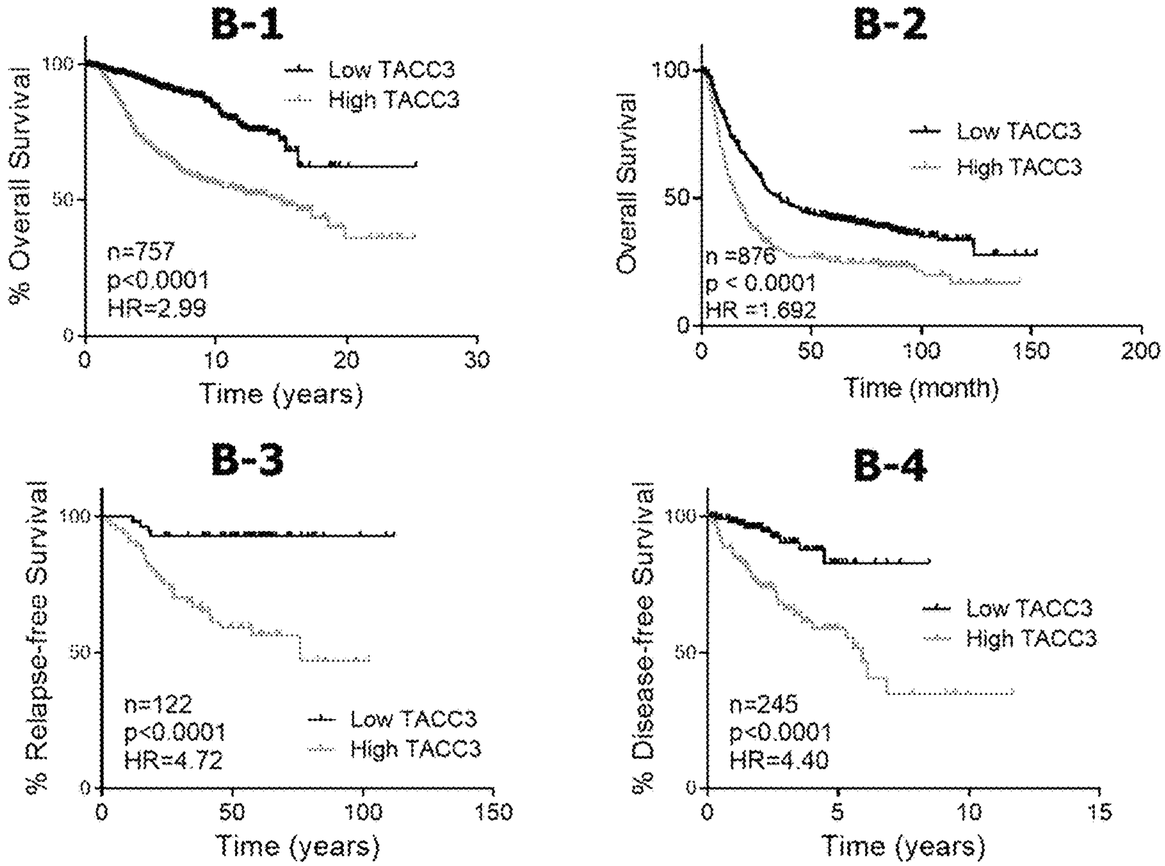
FIG. 1: Generally.

To further investigate the TACC3 level in different tumor types, the present inventors have conducted analyses of the TACC3 levels in many different cancer types and their normal tissue counterparts (FIG. 1A). It was found that TACC3 is significantly overexpressed in many different cancer types including breast cancer. Then, different patient survival datasets using different databases (METABRIC and KM Plotter) and datasets (GSE31210 and TCGA) were analyzed. High TACC3 levels were found to significantly correlate with worse overall survival rates in breast (FIG. 1B-1) and gastric cancer (FIG. 1B-2). Moreover, high TACC3 levels associate with worse relapse-free survival of lung cancer patients (FIG. 1B-3) and disease-free survival of prostate cancer patients (FIG. 1B-4). Importantly, multivariate Cox regression analyses demonstrated that TACC3 expression is an independent prognostic factor in breast cancer (FIG. 2). Altogether, these results indicate that TACC3 is a clinically relevant target and is strongly prognostic in several different cancers, whose expression level is an important factor defining the severity of the disease and patient survival. Therefore, inhibition of TACC3 function is a promising therapeutic strategy to improve survival of breast and other cancer patients.

Figure 3A:
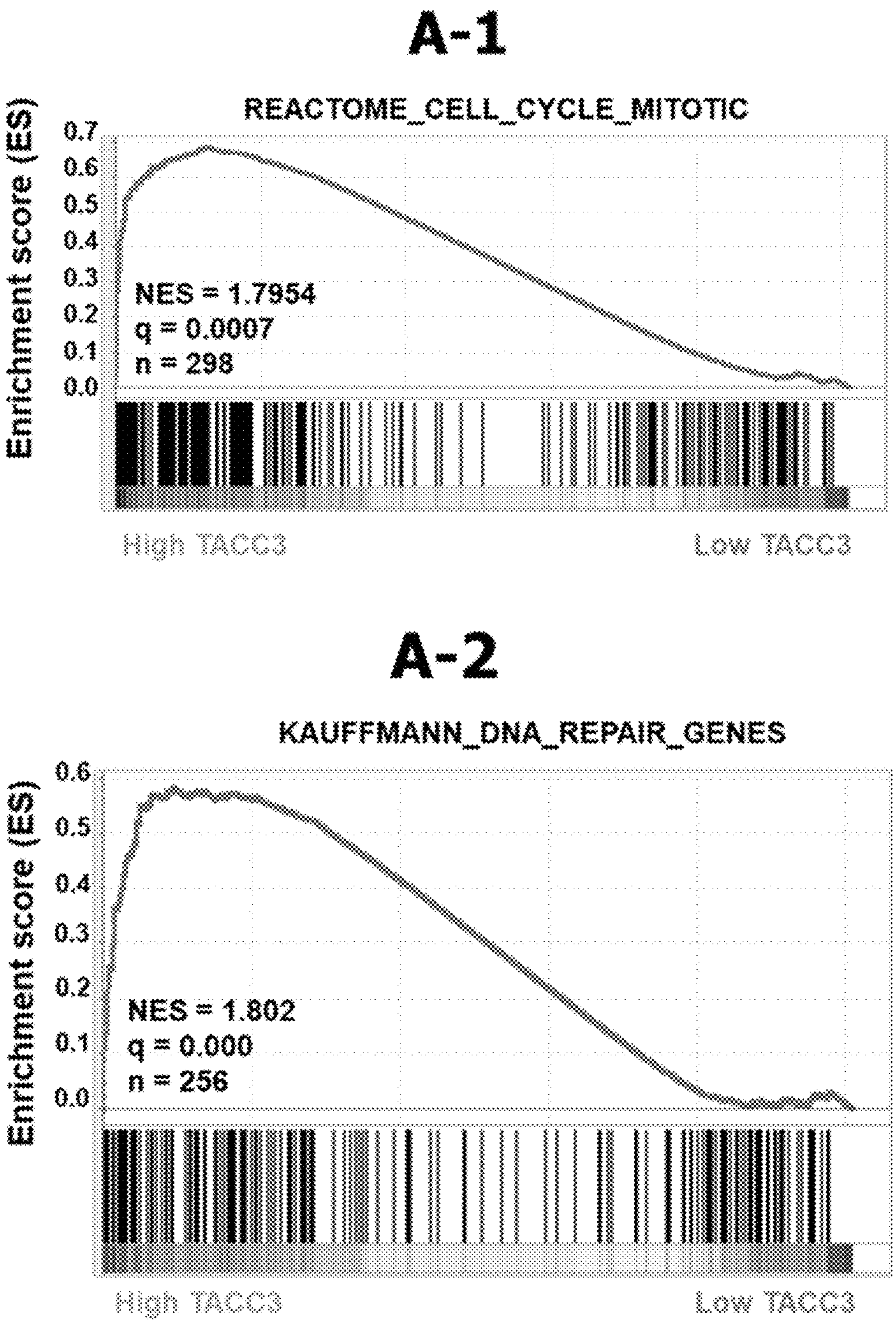
FIG. 3A is an enrichment plot from GSEA conducted with mitosis and DNA repair-related gene sets in METABRIC patients separated according to their TACC3 expression level. Data significance is presented as Normalized Enrichment Score (NES) and FDR (q) value. N indicates total number of the genes used in the analysis.
Figure 3B:
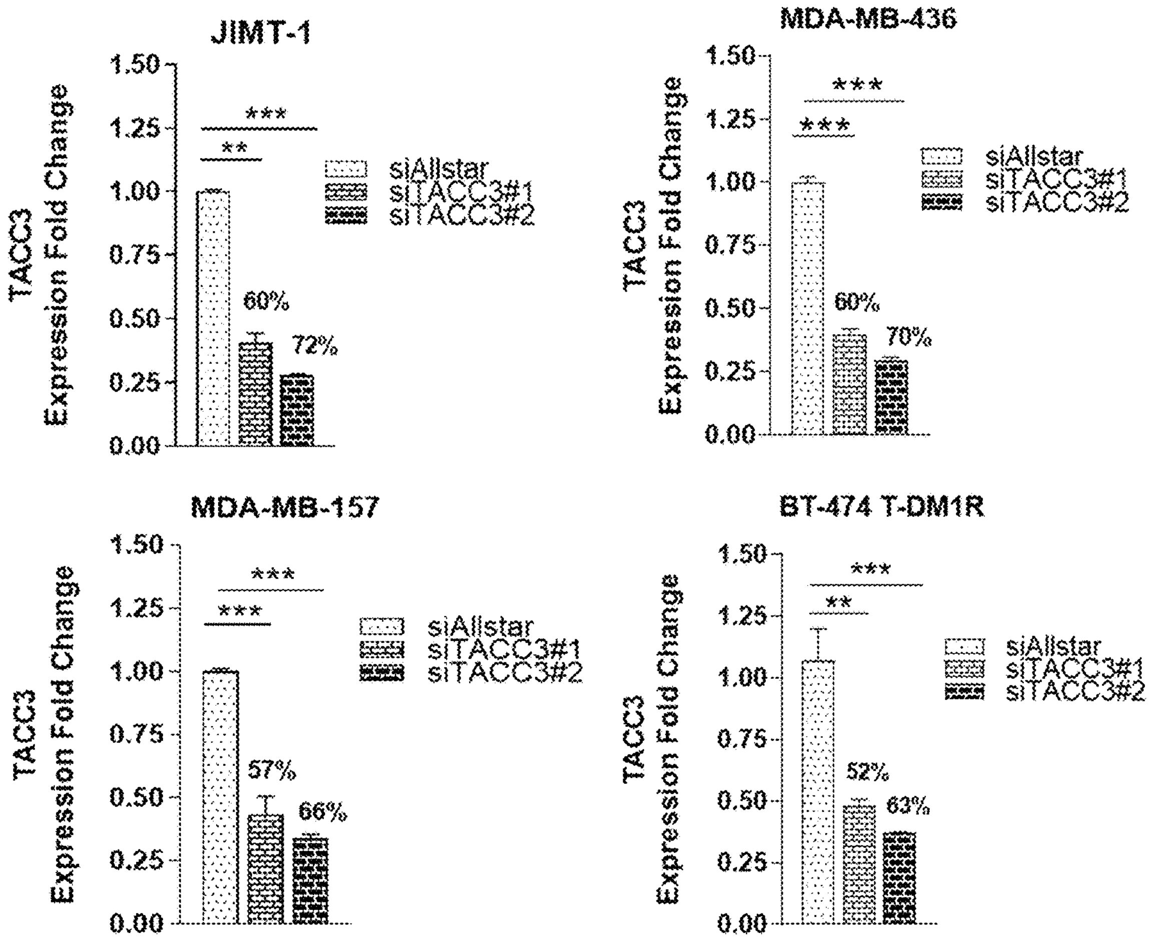
FIG. 3B depicts qRT-PCR studies showing the knockdown efficiency of TACC3-specific siRNAs in breast cancer cell lines. Cells were transfected with 20 nM of two different siRNAs against TACC3, and TACC3 mRNA level was examined after 48 h of transfection. Percentages on the graphs show the knockdown efficiency. *: $p<0.05$; : $p<0.01$; *: $p<0.001$.
Figure 3C:
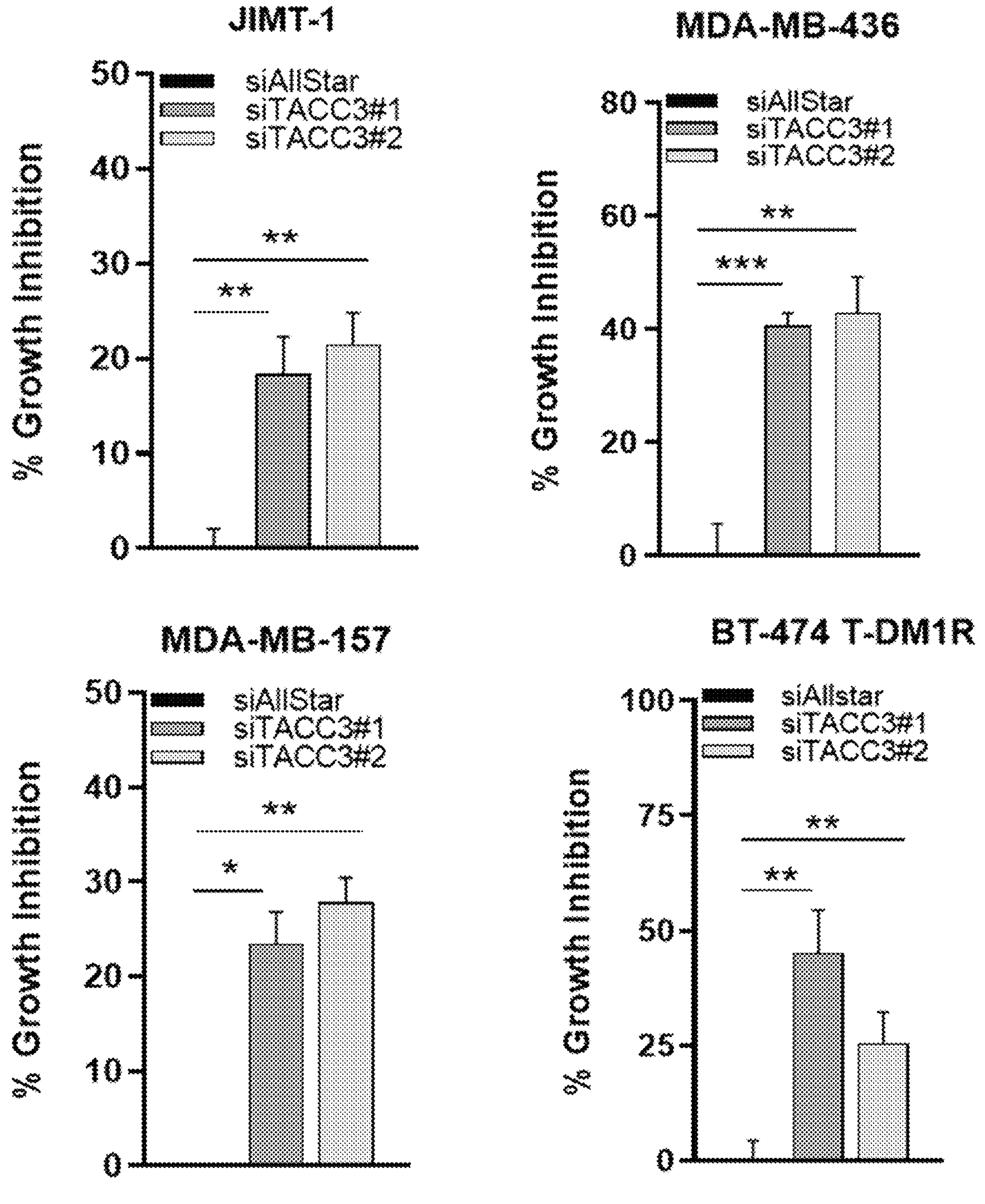
FIG. 3C are graphs showing the growth inhibition of breast cancer cells upon TACC3 knockdown with two different siRNAs. Cells were transfected with siRNAs targeting TACC3, and cell viability was measured after 72 h of transfection.
Figure 3D:
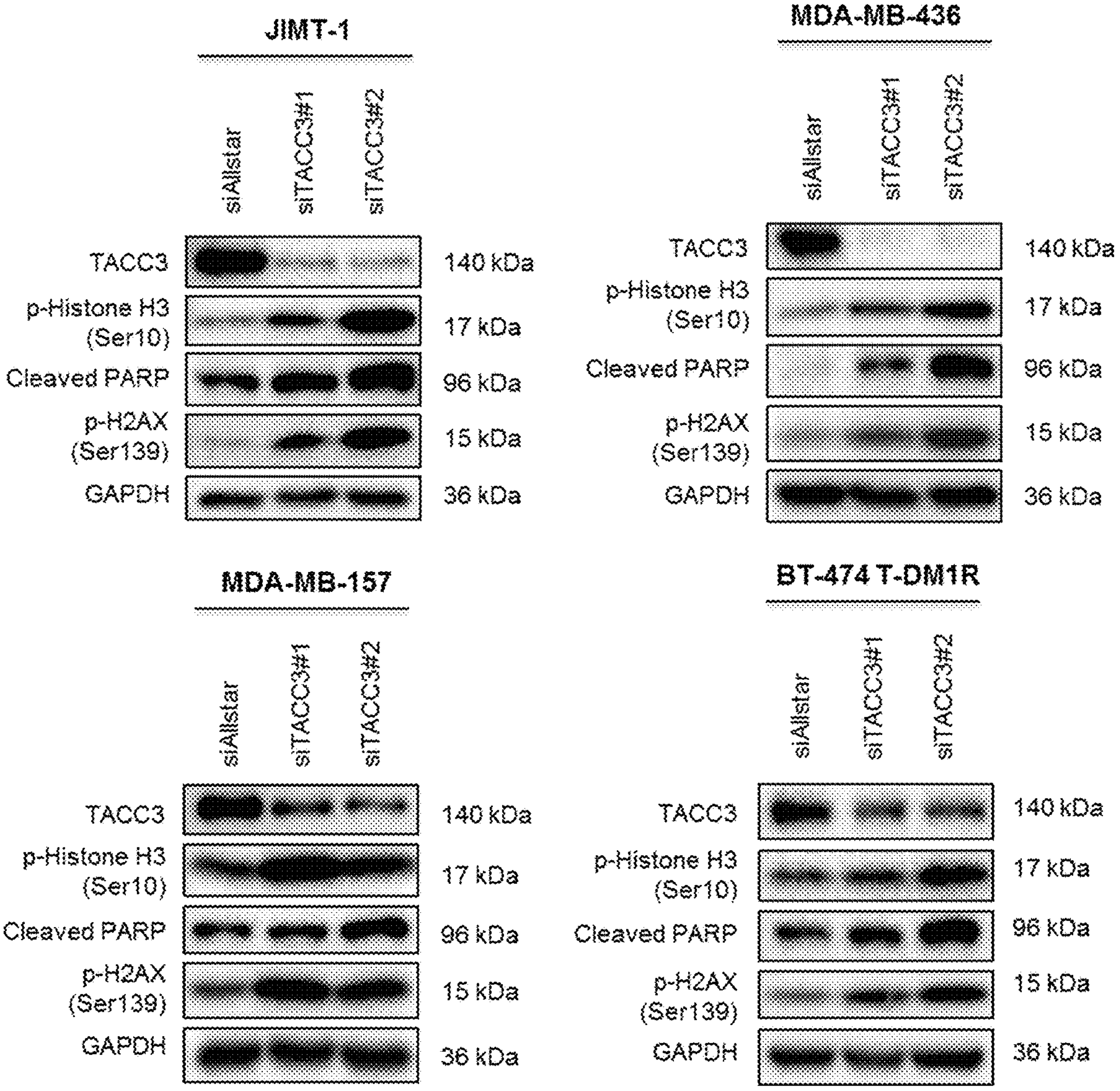
FIG. 3D shows western blot analysis of mitotic arrest, apoptosis and DNA damage markers in breast cancer cells upon TACC3 knockdown. GAPDH was used as a protein loading control.

Reduction in TACC3 levels in Hela cells has been shown to cause mitotic arrest (Schneider et al., 2007) and caspase-dependent apoptosis (Kimura et al., 2013). In the present disclosure, it was found that breast cancer patients who express high TACC3 levels had an enrichment of mitotic progression and DNA repair genes supporting TACC3's oncogenic role in breast cancer development (FIG. 3A). Next, the present inventors have investigated the effect of TACC3 depletion on cell viability of different breast cancer cell lines. Four different breast cancer cell line models with different molecular subtypes were utilized. JIMT-1, a HER2-positive breast cancer cell line, and BT-474 T-DM1R (T-DM1 resistant), a Luminal B subtype breast cancer cell line, were shown to have high TACC3 levels (Saatci et al., 2018). On the other hand, both MDA-MB-436 and MDA-MB-157 are triple negative breast cancer (TNBC) cell lines. In the present disclosure, firstly small interfering RNAs (siRNAs) were used to reduce the TACC3 levels in these cell lines. FIG. 3B shows that the overall TACC3 levels were reduced by approximately 60-70% after 48 h of siRNA treatment in all cell lines. Consistent with this, it was observed that TACC3 knockdown leads to significant growth inhibition of breast cancer cells (FIG. 3C). Then, the possible related mechanisms that TACC3 knockdown could cause were investigated. Suppression of TACC3 levels with siRNAs in all tested breast cancer cell lines activated mitotic arrest, apoptosis and DNA damage (FIG. 3D).

The present inventors performed in-house screening of a series of small molecules by testing their anti-proliferative effects in breast cancer cells in which TACC3 is aberrantly expressed (Ma et al., 2003; Song et al., 2018). Specifically, JIMT-1 cell line was chosen for screening the effect of compounds in cell viability due to its high TACC3 protein level compared to other tested breast cancer cell lines as well as its in vivo tumorigenicity (Saatci et al., 2018; Tanner et al., 2004) (will be discussed in FIGS. 7 and 8-9, respectively). The present inventors have revealed, by experiments using cultured cells that the compound 5 suppresses cell growth ($IC_{50}$ of 190 nM) and exhibits an antitumor effect. Thus, effective anticancer agents can be developed by using this compound as the active pharmaceutical ingredient (API) of an anticancer drug. Thus, in order to obtain novel compounds having anticancer activity against cancer cells expressing high levels of TACC3, compounds having the basic structure of Formula (I) were synthesized.

In one aspect, the present disclosure relates to compounds of Formula (I):

(I)

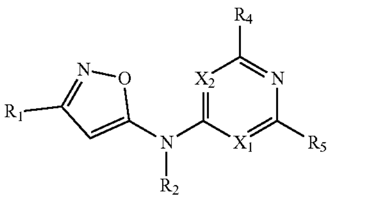

or a pharmaceutically acceptable salt thereof, wherein $X_1$ is N or $CR^6$;

$X_2$ is N or $CR_3$;

$R_1$ is aryl or heteroaryl;

$R_2$ is H or alkyl;

$R_3$, $R_4$ and $R_6$ are each independently H, alkyl, alkenyl, alkynyl, halo, hydroxyl, carboxyl, acyl, acetyl, ester, thioester, alkoxy, phosphoryl, amino, amide, cyano, nitro, azido, alkylthio, alkenyl, alkynyl, cycloalkyl, or sulfonamide; and $R_5$ is heterocyclyl, alkyl, or amino.

In certain embodiments, the compound is not

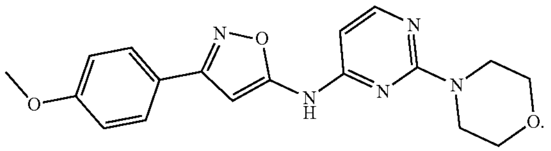 [SMILES: COc1ccc(-c2cc(Nc3ccnc(N4CCOCC4)n3)on2)cc1]

In certain embodiments, $R_1$ is aryl (e.g., phenyl). In other embodiments, $R_1$ is heteroaryl (e.g., benzodioxole, dihydrobenzofuran, benzofuran, or pyrimidinyl).

In certain embodiments, $R_1$ is substituted with one or more substituents selected from alkyl, alkenyl, alkynyl, halo, hydroxyl, carboxyl, acyl, acetyl, ester, thioester, alkoxy, phosphoryl, amino, amide, cyano, nitro, azido, alkylthio, alkenyl, alkynyl, cycloalkyl, alkylsulfonyl (e.g. methylsulfonyl) or sulfonamide. In certain embodiments, $R_1$ is substituted with alkyl (e.g., methyl, ethyl, isopropyl, fluoroethyl, or trifluoromethyl), alkyloxy (e.g., methoxy, trifluoromethyloxy, difluoromethyloxy, ethoxy, or propyloxy), alkylthio (e.g., methylthio), aralkyloxy (e.g., benzyloxy), hydroxyl, halo (e.g., fluoro or chloro), or amino (e.g., dimethylaminoalky). In certain preferred embodiments, $R_1$ is substituted with halo (e.g., fluoro). In certain embodiments, the halo (e.g., F) is para to the isoxazole. In other embodiments, the halo (e.g., F) is ortho to the isoxazole. In other embodiments, the halo (e.g., F) is meta to the isoxazole. In certain preferred embodiments, $R_1$ is substituted with two halo (e.g., F). In certain embodiments, one halo (e.g., F) is meta to the isoxazole and one halo (e.g., F) is ortho to the isoxazole. In other preferred embodiments, $R_1$ is substituted with alkyloxy (e.g., methoxy). In certain embodiments, the alkoxy (e.g., methoxy) is para to the isoxazole. In other embodiments, the alkoxy (e.g., methoxy) is ortho to the isoxazole. In certain embodiments, the alkoxy (e.g., methoxy) is meta to the isoxazole. In yet other preferred embodiments, $R_1$ is substituted with alkyl (e.g., methyl, ethyl, or trifluoromethyl). In yet other preferred embodiments, $R_1$ is substituted with halo (e.g., fluoro) and alkyloxy (e.g., methoxy). In further preferred embodiments, $R_1$ is substituted with a methoxy moiety and one or two fluoro moieties. In the most preferred embodiments, $R_1$ is substituted with a methoxy moiety and two fluoro moieties. In certain embodiments, the alkoxy (e.g., methoxy) is para to the isoxazole and the F is meta to the isoxazole. In yet other embodiments, the alkoxy (e.g., methoxy) is para to the isoxazole and the F is ortho to the isoxazole. In other embodiments, he halo (e.g., F) is para to the isoxazole and the alkoxy (e.g., methoxy) is meta to the isoxazole. In yet other embodiments, the alkoxy (e.g., methoxy) is para to the isoxazole; one halo (e.g., F) is meta to the isoxazole; and one halo (e.g., F) is ortho to the isoxazole.

In certain embodiments, $R_2$ is alkyl (e.g., methyl or ethyl). In certain embodiments, $R_2$ is substituted with amino (e.g., dimethylamino or diethylamino), or nitrile. In other embodiments, $R_2$ is H.

In certain embodiments, $X_1$ is N. In other embodiments, $X_1$ is $CR_6$. In certain embodiments, $R_6$ is H.

In certain embodiments, $X_2$ is N. In other embodiments, $X_2$ is $CR_3$. In certain embodiments, $R_3$ is H or halo (e.g., fluoro or chloro).

In certain embodiments, $R_3$ is H or halo (e.g., fluoro or chloro).

In certain embodiments, $R_4$ is alkyl (e.g., methyl).

In certain embodiments, $R_5$ is heterocyclyl (e.g., azetidinyl, morpholino, pyrrolidinyl, piperazinyl, piperidinyl, oxaazabicyclooctanyl, oxaazabicycloheptnyl, thiomorpholino, thiomorpholino dioxide, hexahydrofuropyrrolyl, or azabicyclohexanyl). In certain embodiments, $R_5$ is a 6-membered containing heterocyclyl and the backbone of the cycle contains one nitrogen. In certain embodiments, $R_5$ is a 6-membered containing heterocyclyl and the backbone of the cycle contains one nitrogen and one oxygen. In other embodiments, $R_5$ is a 7-membered containing heterocyclyl and the backbone of the cycle contains one nitrogen. In certain embodiments, $R_5$ is a 7-membered containing heterocyclyl and the backbone of the cycle contains one nitrogen and one oxygen. In other embodiments, $R_5$ is a 8-membered containing heterocyclyl and the backbone of the cycle contains one nitrogen. In certain embodiments, $R_5$ is a 8-membered containing heterocyclyl and the backbone of the cycle contains one nitrogen and one oxygen. In certain preferred embodiments, $R_5$ is a nitrogen containing heterocyclyl and the nitrogen is directly bonded to the aryl or heteroaryl ring bearing the $R_4$ substituent. In certain preferred embodiments, $R_5$ is 2,6-dimethylmopholine, 4-methylpiperidine, or 4-(trifluoromethyl)piperidine.

In certain embodiments, $R_5$ is substituted with alkyl, alkenyl, alkynyl, halo, hydroxyl, carboxyl, acyl, acetyl, ester, thioester, alkoxy, phosphoryl, amino, amide, cyano, nitro, azido, alkylthio, alkenyl, alkynyl, cycloalkyl, heterocyclyl, or sulfonamide. In certain embodiments, $R_5$ is substituted with ester (e.g., ethylester), carboxyl, alkyl (e.g., methyl or trifluoromethyl), hydroxyalkyl (e.g., hydroxyethyl), halo (e.g., fluoro), cycloalkyl (e.g., cyclopropyl or cyclobutyl), or heterocyclyl (e.g., oxetnyl or tetrahydrofuranyl). In certain preferred embodiments, $R_5$ is substituted with halo (e.g., fluoro). In certain preferred embodiments, $R_5$ is substituted with two alkyl moieties. In even further preferred embodiments, $R_5$ is substituted with two methyl moieties.

In other embodiments, $R_5$ is amino. In certain embodiments, $R_5$ is substituted with alkyl, alkenyl, alkynyl, halo, hydroxyl, carboxyl, acyl, acetyl, ester, thioester, alkoxy, phosphoryl, amino, amide, cyano, nitro, azido, alkylthio, alkenyl, alkynyl, cycloalkyl, sulfonamide, cycloalkyl, or heterocyclyl). In certain embodiments, $R_5$ is substituted with alkyl (e.g., difluoroethyl, or isobutyl, alkyloxyalkyl (such as methyloxyethyl), hydroxyalkyl (such as hydroxyethyl), cycloalkyl (e.g., cyclopropyl), or heterocyclyl (e.g., pyranyl).

In certain embodiments, the compound of formula I has a structure represented by formula II:

(II)

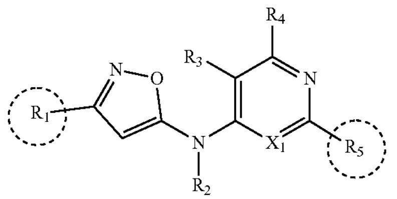

The anticancer agent of the present disclosure comprises a compound represented by the general formula (I) wherein;

$R_1$: Non-substituted phenyl or o-, m- or p-$CH_3$, $C_2H_5$, $CH(CH_3)_2$, $OCH_3$, $OC_2H_5$, $OC_3H_7$, $SCH_3$, $CF_2CH_3$, $CF_3$, $OCF_3$, $OCHF_2$, $N(CH_3)_2$, F, Cl, OH mono or disubstituted phenyl, pyridyl, benzyloxy or piperonyl group; $R_2$: H, $CH_3$; $R_3$: H, F, Cl; $R_4$: H, $CH_3$; $X_1$: CH, N; $R_5$: Morpholine, 2,6-dimethylmorpholine, thiomorpholine, thiomorpholine 1,1-dioxide, morpholin-4-amine, piperidine, tetrahydro-2H-pyran-4-amine, piperidin-1-amine, 4-fluoropiperidine, 4,4-difluoropiperidine, 4-methylpiperidine, 4-(trifluoromethyl)piperidine, piperazine, N-methyl piperazine, pyrrolidine, 2-(4-piperidinyl)ethanol, 2-(1-piperazinyl)ethanol, 4-piperidinecarboxylic acid, ethyl 4-piperidinecarboxylate, (1R,4R)-2-oxa-5-azabicyclo[2.2.1]heptane, (1S,4S)-2-oxa-5-azabicyclo[2.2.1]heptane, 3-oxa-8-azabicyclo[3.2.1]octane or 8-oxa-3-azabicyclo[3.2.1] octane group.

In certain embodiments, $R_1$ is phenyl. In other embodiments, $R_1$ is pyridyl. In yet other embodiments, $R_1$ is benzyloxy. In yet other embodiments, $R_1$ is piperonyl. In certain embodiments, $R_1$ is substituted with $CH_3$, $C_2H_5$, $CH(CH_3)_2$, $OCH_3$, $OC_2H_5$, $OC_3H_7$, $SCH_3$, $CF_2CH_3$, $CF_3$, $OCF_3$, $OCHF_2$, $N(CH_3)_2$, F, Cl, or OH. In certain preferred embodiments, $R_1$ is substituted with $CH_3$. In other preferred embodiments, $R_1$ is substituted with $OCH_3$. In certain embodiments, the $OCH_3$ is para to the isoxazole. In certain embodiments, the $OCH_3$ is ortho to the isoxazole. In certain embodiments, the $OCH_3$ is meta to the isoxazole. In yet other preferred embodiments, $R_1$ is substituted with F. In certain embodiments, $R_1$ is substituted with one F. In certain embodiments, the F is para to the isoxazole. In certain embodiments, the F is ortho to the isoxazole. In certain embodiments, the F is meta to the isoxazole. In certain embodiments, $R_1$ is substituted with two Fs. In certain embodiments, the first F is meta to the isoxazole and the second F is ortho to the isoxazole. In further preferred embodiments, $R_1$ is substituted with $OCH_3$ and F. In certain embodiments, the $OCH_3$ is para to the isoxazole and the F is meta to the isoxazole. In certain embodiments, the $OCH_3$ is para to the isoxazole and the F is ortho to the isoxazole. In certain embodiments, the F is para to the isoxazole and the $OCH_3$ is meta to the isoxazole. In further preferred embodiments, $R_1$ is substituted with $OCH_3$ and two F. In certain embodiments, the $OCH_3$ is para to the isoxazole and both Fs areas meta to the isoxazole. In certain embodiments, the $OCH_3$ is para to the isoxazole; one F is meta to the isoxazole; and one F is ortho to the isoxazole.

In certain embodiments, $R_2$ is H. In other embodiments, $R_2$ is $CH_3$.

In certain embodiments, $R_3$ is H. In other embodiments, $R_3$ is F. In yet other embodiments, $R_3$ is Cl.

In certain preferred embodiments, $R_5$ is morpholine. In other preferred embodiments, $R_5$ is piperidine. In yet other preferred embodiments, $R_5$ is 4-fluoropiperidine. In yet other preferred embodiments, $R_5$ is 4,4-difluoropiperidine. In yet other preferred embodiments, $R_5$ is 3-oxa-8-azabicyclo[3.2.1]octane. In yet other preferred embodiments, $R_5$ is 8-oxa-3-azabicyclo[3.2.1]octane. In yet other preferred embodiments, $R_5$ is 2,6-dimethylmorpholine. In yet other preferred embodiments, $R_5$ is 4-methylpiperidine. In yet other preferred embodiments, $R_5$ is 4-methylpiperidine.

In certain embodiments, $X_1$ is C. In other embodiments, $X_1$ is N.

Certain final components of the disclosure is shown below:

3-(3-methoxyphenyl)-N-(2-morpholinopyrimidin-4-yl) isoxazol-5-amine (Compound 6)

3-(2-methoxyphenyl)-N-(2-morpholinopyrimidin-4-yl) isoxazol-5-amine (Compound 7)

N-(2-morpholinopyrimidin-4-yl)-3-phenylisoxazol-5-amine (Compound 8)

3-(4-ethoxyphenyl)-N-(2-morpholinopyrimidin-4-yl)isoxazol-5-amine (Compound 9)

N-(2-morpholinopyrimidin-4-yl)-3-(4-propoxyphenyl) isoxazol-5-amine (Compound 10)

3-(4-fluorophenyl)-N-(2-morpholinopyrimidin-4-yl)isoxazol-5-amine (Compound 11)

3-(4-chlorophenyl)-N-(2-morpholinopyrimidin-4-yl)isoxazol-5-amine (Compound 12)

N-(2-morpholinopyrimidin-4-yl)-3-(p-tolyl)isoxazol-5-amine (Compound 13)

3-(4-ethylphenyl)-N-(2-morpholinopyrimidin-4-yl)isoxazol-5-amine (Compound 14)

3-(4-isopropylphenyl)-N-(2-morpholinopyrimidin-4-yl) isoxazol-5-amine (Compound 15)

N-(2-morpholinopyrimidin-4-yl)-3-(4-(trifluoromethyl)phenyl)isoxazol-5-amine (Compound 16)

3-(4-(1,1-difluoroethyl)phenyl)-N-(2-morpholinopyrimidin-4-yl)isoxazol-5-amine (Compound 17)

3-(4-(difluoromethoxy)phenyl)-N-(2-morpholinopyrimidin-4-yl)isoxazol-5-amine (Compound 18)

N-(2-morpholinopyrimidin-4-yl)-3-(4-(trifluoromethoxy) phenyl)isoxazol-5-amine (Compound 19)

3-(4-(methylthio)phenyl)-N-(2-morpholinopyrimidin-4-yl) isoxazol-5-amine (Compound 20)

3-(4-(dimethylamino)phenyl)-N-(2-morpholinopyrimidin-4-yl)isoxazol-5-amine (Compound 21)

3-(3-fluoro-4-methoxyphenyl)-N-(2-morpholinopyrimidin-4-yl)isoxazol-5-amine (Compound 22)

3-(3-chloro-4-methoxyphenyl)-N-(2-morpholinopyrimidin-4-yl)isoxazol-5-amine (Compound 23)

3-(3,4-dimethoxyphenyl)-N-(2-morpholinopyrimidin-4-yl) isoxazol-5-amine (Compound 24)

3-(2,3-difluoro-4-methoxyphenyl)-N-(2-morpholinopyrimidin-4-yl)isoxazol-5-amine (Compound 25) 3-(benzo[d] [1,3]dioxol-5-yl)-N-(2-morpholinopyrimidin-4-yl)isoxazol-5-amine (Compound 26)

3-(6-methoxypyridin-3-yl)-N-(2-morpholinopyrimidin-4-yl)isoxazol-5-amine (Compound 27)

4-(5-((2-morpholinopyrimidin-4-yl)amino)isoxazol-3-yl) phenol (Compound 30)

3-(4-(benzyloxy)phenyl)-N-(2-morpholinopyrimidin-4-yl)isoxazol-5-amine (Compound 32)

N-(2-((2R,6S)-2,6-dimethylmorpholino)pyrimidin-4-yl)-3-(4-methoxyphenyl)isoxazol-5-amine (Compound 33)

N-(2-(3-oxa-8-azabicyclo[3.2.1]octan-8-yl)pyrimidin-4-yl)-3-(4-methoxyphenyl)isoxazol-5-amine (Compound 34)

N-(2-(8-oxa-3-azabicyclo[3.2.1]octan-3-yl)pyrimidin-4-yl)-3-(4-methoxyphenyl)isoxazol-5-amine (Compound 35)

N-(2-((1S,4S)-2-oxa-5-azabicyclo[2.2.1]heptan-5-yl)pyrimidin-4-yl)-3-(4-methoxyphenyl)isoxazol-5-amine (Compound 36)

N-(2-((1R,4R)-2-oxa-5-azabicyclo[2.2.1]heptan-5-yl)pyrimidin-4-yl)-3-(4-methoxyphenyl)isoxazol-5-amine (Compound 37)

N-(2-(4-fluoropiperidin-1-yl)pyrimidin-4-yl)-3-(4-methoxyphenyl)isoxazol-5-amine (Compound 38)

N-(2-(4,4-difluoropiperidin-1-yl)pyrimidin-4-yl)-3-(4-methoxyphenyl)isoxazol-5-amine (Compound 39)

3-(4-methoxyphenyl)-N-(2-thiomorpholinopyrimidin-4-yl)isoxazol-5-amine (Compound 40)

4-(4-((3-(4-methoxyphenyl)isoxazol-5-yl)amino)pyrimidin-2-yl)thiomorpholine 1,1-dioxide (Compound 41)

3-(4-methoxyphenyl)-N-(2-(piperidin-1-yl)pyrimidin-4-yl)isoxazol-5-amine (Compound 42)

3-(4-methoxyphenyl)-N-(2-(4-methylpiperidin-1-yl)pyrimidin-4-yl)isoxazol-5-amine (Compound 43)

3-(4-methoxyphenyl)-N-(2-(4-(trifluoromethyl)piperidin-1-yl)pyrimidin-4-yl)isoxazol-5-amine (Compound 44)

3-(4-methoxyphenyl)-N-(2-(pyrrolidin-1-yl)pyrimidin-4-yl)isoxazol-5-amine (Compound 45)

2-(1-(4-((3-(4-methoxyphenyl)isoxazol-5-yl)amino)pyrimidin-2-yl)piperidin-4-yl)ethan-1-ol (Compound 46)

2-(4-(4-((3-(4-methoxyphenyl)isoxazol-5-yl)amino)pyrimidin-2-yl)piperazin-1-yl)ethan-1-ol (Compound 47)

3-(4-methoxyphenyl)-N-(2-(4-methylpiperazin-1-yl)pyrimidin-4-yl)isoxazol-5-amine (Compound 48)

3-(4-methoxyphenyl)-N-(2-(piperazin-1-yl)pyrimidin-4-yl)isoxazol-5-amine (Compound 49) Ethyl 1-(4-((3-(4-methoxyphenyl)isoxazol-5-yl)amino)pyrimidin-2-yl)piperidine-4-carboxylate (Compound 50)

1-(4-((3-(4-methoxyphenyl)isoxazol-5-yl)amino)pyrimidin-2-yl)piperidine-4-carboxylic acid (Compound 51)

$N^4$-(3-(4-methoxyphenyl)isoxazol-5-yl)-$N^2$-morpholinopyrimidine-2,4-diamine (Compound 52)

$N^4$-(3-(4-methoxyphenyl)isoxazol-5-yl)-$N^2$-(piperidin-1-yl)pyrimidine-2,4-diamine (Compound 53)

$N^4$-(3-(4-methoxyphenyl)isoxazol-5-yl)-$N^2$-(tetrahydro-2H-pyran-4-yl)pyrimidine-2,4-diamine (Compound 54)

N-(5-chloro-2-(4-fluoropiperidin-1-yl)pyrimidin-4-yl)-3-(4-methoxyphenyl)isoxazol-5-amine (Compound 59)

N-(5-fluoro-2-(4-fluoropiperidin-1-yl)pyrimidin-4-yl)-3-(4-methoxyphenyl)isoxazol-5-amine (Compound 60)

N-(2-(4-fluoropiperidin-1-yl)-6-methylpyrimidin-4-yl)-3-(4-methoxyphenyl)isoxazol-5-amine (Compound 61)

3-(4-methoxyphenyl)-N-(2-morpholinopyridin-4-yl)isoxazol-5-amine (Compound 62)

3-(4-methoxyphenyl)-N-methyl-N-(2-morpholinopyrimidin-4-yl)isoxazol-5-amine (Compound 63)

3-(4-(dimethylamino)phenyl)-N-(2-(4-fluoropiperidin-1-yl)pyrimidin-4-yl)isoxazol-5-amine (Compound 64)

3-(3-fluoro-4-methoxyphenyl)-N-(2-(4-fluoropiperidin-1-yl)pyrimidin-4-yl)isoxazol-5-amine (Compound 65)

N-(2-(3-oxa-8-azabicyclo[3.2.1]octan-8-yl)pyrimidin-4-yl)-3-(3-fluoro-4-methoxyphenyl)isoxazol-5-amine (Compound 66)

3-(3-fluoro-4-methoxyphenyl)-N-(2-(pyrrolidin-1-yl)pyrimidin-4-yl)isoxazol-5-amine (Compound 67)

3-(2,3-dihydrobenzofuran-5-yl)-N-(2-morpholinopyrimidin-4-yl)isoxazol-5-amine (Compound 69)

3-(2,2-difluorobenzo[d][1,3]dioxol-5-yl)-N-(2-morpholinopyrimidin-4-yl)isoxazol-5-amine (Compound 70)

$N^2$-cyclopropyl-$N^4$-(3-(4-methoxyphenyl)isoxazol-5-yl)pyrimidine-2,4-diamine (Compound 71)

$N^2$-isobutyl-$N^4$-(3-(4-methoxyphenyl)isoxazol-5-yl)pyrimidine-2,4-diamine (Compound 72)

$N^2$-(2-methoxyethyl)-$N^4$-(3-(4-methoxyphenyl)isoxazol-5-yl)pyrimidine-2,4-diamine (Compound 73)

$N^1$,$N^1$-diethyl-$N^2$-(3-(4-methoxyphenyl)isoxazol-5-yl)-$N^2$-(2-morpholinopyrimidin-4-yl)ethane-1,2-diamine (Compound 74) $N^1$-(3-(4-methoxyphenyl)isoxazol-5-yl)-$N^2$,$N^2$-dimethyl-N1-(2-morpholinopyrimidin-4-yl)ethane-1,2-diamine (Compound 75) 2-((3-(4-methoxyphenyl)isoxazol-5-yl)(2-morpholinopyrimidin-4-yl)amino)acetonitrile (Compound 76)

3-(5-methoxypyridin-2-yl)-N-(2-morpholinopyrimidin-4-yl)isoxazol-5-amine (Compound 77)

3-(4-methoxyphenyl)-N-(2-morpholinopyridin-4-yl)isoxazol-5-amine (Compound 78)

3-(3-fluoro-4-methoxyphenyl)-N-(2-morpholinopyridin-4-yl)isoxazol-5-amine (Compound 79)

3-(4-methoxyphenyl)-N-(4-morpholino-1,3,5-triazin-2-yl)isoxazol-5-amine (Compound 80)

$N^2$-(2,2-difluoroethyl)-$N^4$-(3-(4-methoxyphenyl)isoxazol-5-yl)pyrimidine-2,4-diamine (Compound 81) 2-((4-((3-(4-methoxyphenyl)isoxazol-5-yl)amino)pyrimidin-2-yl)amino)ethan-1-ol (Compound 82)

3-(2-fluoro-4-methoxyphenyl)-N-(2-morpholinopyrimidin-4-yl)isoxazol-5-amine (Compound 83)

3-(2,3-difluoro-4-methoxyphenyl)-N-(2-morpholinopyrimidin-4-yl)isoxazol-5-amine (Compound 84)

3-(3,5-difluoro-4-methoxyphenyl)-N-(2-morpholinopyrimidin-4-yl)isoxazol-5-amine (Compound 85)

N-(2-morpholinopyrimidin-4-yl)-3-(3,4,5-trimethoxyphenyl)isoxazol-5-amine (Compound 86) 3-(benzofuran-5-yl)-N-(2-morpholinopyrimidin-4-yl)isoxazol-5-amine (Compound 87)

3-(2,5-difluoro-4-methoxyphenyl)-N-(2-morpholinopyrimidin-4-yl)isoxazol-5-amine (Compound 88)

3-(2,5-difluoro-4-methoxyphenyl)-N-(2-((2R,6S)-2,6-dimethylmorpholino)pyrimidin-4-yl)isoxazol-5-amine (Compound 89)

$N^4$-(3-(4-methoxyphenyl)isoxazol-5-yl)-$N^2$-methylpyrimidine-2,4-diamine (Compound 90)

3-(3-fluoro-4-methoxyphenyl)-N-(2-(4-(trifluoromethyl)piperidin-1-yl)pyrimidin-4-yl)isoxazol-5-amine (Compound 91)

3-(3-fluoro-4-methoxyphenyl)-N-(2-(4-methylpiperidin-1-yl)pyrimidin-4-yl)isoxazol-5-amine (Compound 92)

N-(2-((2R,6S)-2,6-dimethylmorpholino)pyrimidin-4-yl)-3-(3-fluoro-4-methoxyphenyl)isoxazol-5-amine (Compound 93)

3-(2-fluoro-4-methoxyphenyl)-N-(2-(4-(trifluoromethyl)piperidin-1-yl)pyrimidin-4-yl)isoxazol-5-amine (Compound 94)

3-(2-fluoro-4-methoxyphenyl)-N-(2-(4-methylpiperidin-1-yl)pyrimidin-4-yl)isoxazol-5-amine (Compound 95)

N-(2-((2R,6S)-2,6-dimethylmorpholino)pyrimidin-4-yl)-3-(2-fluoro-4-methoxyphenyl)isoxazol-5-amine (Compound 96)

3-(2-fluoro-4-methoxyphenyl)-N-(2-(2,2,6,6-tetramethylmorpholino)pyrimidin-4-yl)isoxazol-5-amine (Compound 97)

N-(2-(3,3-dimethylmorpholino)pyrimidin-4-yl)-3-(2-fluoro-4-methoxyphenyl)isoxazol-5-amine (Compound 98)

N-(2-(2,2-dimethylmorpholino)pyrimidin-4-yl)-3-(2-fluoro-4-methoxyphenyl)isoxazol-5-amine (Compound 99)

N-(2-(3,5-dimethylmorpholino)pyrimidin-4-yl)-3-(2-fluoro-4-methoxyphenyl)isoxazol-5-amine (Compound 100)

3-(2-fluoro-4-methoxyphenyl)-N-(2-(2-methylmorpholino)pyrimidin-4-yl)isoxazol-5-amine (Compound 101)

3-(2-fluoro-4-methoxyphenyl)-N-(2-(3-methylmorpholino)pyrimidin-4-yl)isoxazol-5-amine (Compound 102)

3-(2-fluoro-4-methoxyphenyl)-N-(2-(2-(trifluoromethyl)morpholino)pyrimidin-4-yl)isoxazol-5-amine (Compound 103)

3-(2-fluoro-4-methoxyphenyl)-N-(2-(tetrahydro-1H-furo[3,4-c]pyrrol-5(3H)-yl)pyrimidin-4-yl)isoxazol-5-amine (Compound 104)

N-(2-(3-azabicyclo[3.1.0]hexan-3-yl)pyrimidin-4-yl)-3-(2-fluoro-4-methoxyphenyl)isoxazol-5-amine (Compound 105)

N-(2-(7-azaspiro[3.5]nonan-7-yl)pyrimidin-4-yl)-3-(2-fluoro-4-methoxyphenyl)isoxazol-5-amine (Compound 106)

N-(2-(4,4-dimethylpiperidin-1-yl)pyrimidin-4-yl)-3-(2-fluoro-4-methoxyphenyl)isoxazol-5-amine (Compound 107)

N-(2-(2-oxa-6-azaspiro[3.3]heptan-6-yl)pyrimidin-4-yl)-3-(2-fluoro-4-methoxyphenyl)isoxazol-5-amine (Compound 108)

N-(2-(1-oxa-7-azaspiro[3.5]nonan-7-yl)pyrimidin-4-yl)-3-(2-fluoro-4-methoxyphenyl)isoxazol-5-amine (Compound 109)

N-(2-(6-azaspiro[2.5]octan-6-yl)pyrimidin-4-yl)-3-(2-fluoro-4-methoxyphenyl)isoxazol-5-amine (Compound 110)

3-(2-fluoro-4-methoxyphenyl)-N-(2-(3-methyl-8-azabicyclo[3.2.1]octan-8-yl)pyrimidin-4-yl)isoxazol-5-amine (Compound 111)

N-(2-(2,2-difluoromorpholino)pyrimidin-4-yl)-3-(2-fluoro-4-methoxyphenyl)isoxazol-5-amine (Compound 112)

N-(2-(2-oxa-5-azabicyclo[2.2.2]octan-5-yl)pyrimidin-4-yl)-3-(2-fluoro-4-methoxyphenyl)isoxazol-5-amine (Compound 113)

3-(2-fluoro-4-methoxyphenyl)-N-(2-(3-(trifluoromethyl)morpholino)pyrimidin-4-yl)isoxazol-5-amine (Compound 114)

N-(2-(6-oxa-3-azabicyclo[3.1.1]heptan-3-yl)pyrimidin-4-yl)-3-(2-fluoro-4-methoxyphenyl)isoxazol-5-amine (Compound 115)

N-(2-(2-oxa-5-azabicyclo[4.1.0]heptan-5-yl)pyrimidin-4-yl)-3-(2-fluoro-4-methoxyphenyl)isoxazol-5-amine (Compound 116)

N-(2-(4-oxa-7-azaspiro[2.5]octan-7-yl)pyrimidin-4-yl)-3-(2-fluoro-4-methoxyphenyl)isoxazol-5-amine (Compound 117)

N-(2-(7-oxa-4-azaspiro[2.5]octan-4-yl)pyrimidin-4-yl)-3-(2-fluoro-4-methoxyphenyl)isoxazol-5-amine (Compound 118)

N-(2-(2-oxa-8-azaspiro[4.5]decan-8-yl)pyrimidin-4-yl)-3-(2-fluoro-4-methoxyphenyl)isoxazol-5-amine (Compound 119)

N-(2-(2-oxa-6-azaspiro[3.4]octan-6-yl)pyrimidin-4-yl)-3-(2-fluoro-4-methoxyphenyl)isoxazol-5-amine (Compound 120)

N-(2-(2-oxa-7-azaspiro[3.5]nonan-7-yl)pyrimidin-4-yl)-3-(2-fluoro-4-methoxyphenyl)isoxazol-5-amine (Compound 121)

N-(2-(2-oxa-7-azaspiro[4.4]nonan-7-yl)pyrimidin-4-yl)-3-(2-fluoro-4-methoxyphenyl)isoxazol-5-amine (Compound 122)

3-(2-fluoro-4-methoxyphenyl)-N-(2-(2,2,6,6-tetrafluoromorpholino)pyrimidin-4-yl)isoxazol-5-amine (Compound 123)

N-(2-(6-azabicyclo[3.1.1]heptan-6-yl)pyrimidin-4-yl)-3-(2-fluoro-4-methoxyphenyl)isoxazol-5-amine (Compound 124)

3-(2-fluoro-4-methoxyphenyl)-N-(2-(3-methyl-6-azabicyclo[3.1.1]heptan-6-yl)pyrimidin-4-yl)isoxazol-5-amine (Compound 125)

N-(2-(3,5-dimethylpiperidin-1-yl)pyrimidin-4-yl)-3-(2-fluoro-4-methoxyphenyl)isoxazol-5-amine (Compound 126)

3-(2-fluoro-4-methoxyphenyl)-N-(2-(4-isopropylpiperidin-1-yl)pyrimidin-4-yl)isoxazol-5-amine (Compound 127)

N-(2-(4-(difluoromethyl)piperidin-1-yl)pyrimidin-4-yl)-3-(2-fluoro-4-methoxyphenyl)isoxazol-5-amine (Compound 128)

N-(2-(6-azaspiro[3.5]nonan-6-yl)pyrimidin-4-yl)-3-(2-fluoro-4-methoxyphenyl)isoxazol-5-amine (Compound 129)

N-(2-(2-azaspiro[3.5]nonan-2-yl)pyrimidin-4-yl)-3-(2-fluoro-4-methoxyphenyl)isoxazol-5-amine (Compound 130)

3-(2-chloro-4-methoxyphenyl)-N-(2-morpholinopyrimidin-4-yl)isoxazol-5-amine (Compound 131) Each original intermediate of the disclosure are shown below:

N-(2-chloropyrimidin-4-yl)-3-(4-methoxyphenyl)isoxazol-5-amine (Compound 4a)

N-(2-chloropyrimidin-4-yl)-3-(3-methoxyphenyl)isoxazol-5-amine (Compound 4b)

N-(2-chloropyrimidin-4-yl)-3-(2-methoxyphenyl)isoxazol-5-amine (Compound 4c)

N-(2-chloropyrimidin-4-yl)-3-phenylisoxazol-5-amine (Compound 4d)

N-(2-chloropyrimidin-4-yl)-3-(4-ethoxyphenyl)isoxazol-5-amine (Compound 4e)

N-(2-chloropyrimidin-4-yl)-3-(4-propoxyphenyl)isoxazol-5-amine (Compound 4f)

N-(2-chloropyrimidin-4-yl)-3-(4-fluorophenyl)isoxazol-5-amine (Compound 4g)

3-(4-chlorophenyl)-N-(2-chloropyrimidin-4-yl)isoxazol-5-amine (Compound 4h)

N-(2-chloropyrimidin-4-yl)-3-(p-tolyl)isoxazol-5-amine (Compound 4i)

N-(2-chloropyrimidin-4-yl)-3-(4-ethylphenyl)isoxazol-5-amine (Compound 4j)

N-(2-chloropyrimidin-4-yl)-3-(4-isopropylphenyl)isoxazol-5-amine (Compound 4k)

N-(2-chloropyrimidin-4-yl)-3-(4-(trifluoromethyl)phenyl)isoxazol-5-amine (Compound 41)

N-(2-chloropyrimidin-4-yl)-3-(4-(1,1-difluoroethyl)phenyl)isoxazol-5-amine (Compound 4m)

N-(2-chloropyrimidin-4-yl)-3-(4-(difluoromethoxy)phenyl)isoxazol-5-amine (Compound 4n)

N-(2-chloropyrimidin-4-yl)-3-(4-(trifluoromethoxy)phenyl)isoxazol-5-amine (Compound 4o)

N-(2-chloropyrimidin-4-yl)-3-(4-(methylthio)phenyl)isoxazol-5-amine (Compound 4p)

N-(2-chloropyrimidin-4-yl)-3-(4-(dimethylamino)phenyl)isoxazol-5-amine (Compound 4r)

N-(2-chloropyrimidin-4-yl)-3-(3-fluoro-4-methoxyphenyl) isoxazol-5-amine (Compound 4s)

3-(3-chloro-4-methoxyphenyl)-N-(2-chloropyrimidin-4-yl) isoxazol-5-amine (Compound 4t)

N-(2-chloropyrimidin-4-yl)-3-(3,4-dimethoxyphenyl)isoxazol-5-amine (Compound 4u)

N-(2-chloropyrimidin-4-yl)-3-(2,3-difluoro-4-methoxyphenyl)isoxazol-5-amine (Compound 4v) 3-(benzo[d][1,3]dioxol-5-yl)-N-(2-chloropyrimidin-4-yl)isoxazol-5-amine (Compound 4y)

N-(2-chloropyrimidin-4-yl)-3-(6-methoxypyridin-3-yl) isoxazol-5-amine (Compound 4z)

3-(4-methoxyphenyl)-N-(2-(methylthio)pyrimidin-4-yl) isoxazol-5-amine (Compound 28)

4-(5-((2-chloropyrimidin-4-yl)amino)isoxazol-3-yl)phenol (Compound 29)

3-(4-(benzyloxy)phenyl)-N-(2-chloropyrimidin-4-yl)isoxazol-5-amine (Compound 31)

N-(2,5-dichloropyrimidin-4-yl)-3-(4-methoxyphenyl)isoxazol-5-amine (Compound 55)

N-(2-chloro-5-fluoropyrimidin-4-yl)-3-(4-methoxyphenyl) isoxazol-5-amine (Compound 56)

N-(2-chloro-6-methylpyrimidin-4-yl)-3-(4-methoxyphenyl) isoxazol-5-amine (Compound 57)

N-(2-chloropyridin-4-yl)-3-(4-methoxyphenyl)isoxazol-5-amine (Compound 58)

N-(2-chloropyrimidin-4-yl)-3-(2-fluoro-4-methoxyphenyl) isoxazol-5-amine (Compound 132)

N-(2-chloropyrimidin-4-yl)-3-(2,5-difluoro-4-methoxyphenyl)isoxazol-5-amine (Compound 133)

The anticancer agent of the present disclosure comprises a compound of general Formula (I) represented by the following chemical structures of certain final compounds of the disclosure:

6

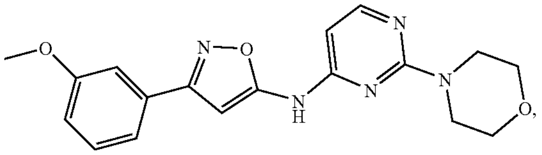

7

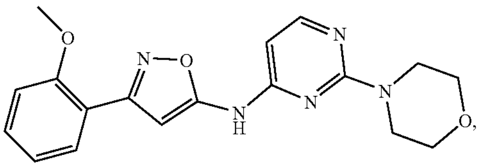

8

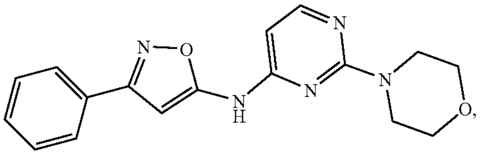

9

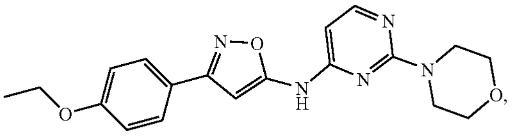

-continued

10

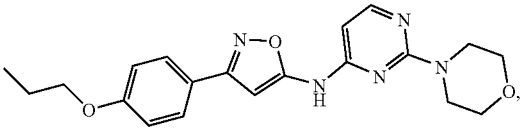

11

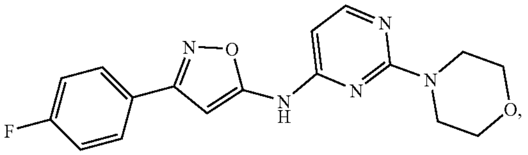

12

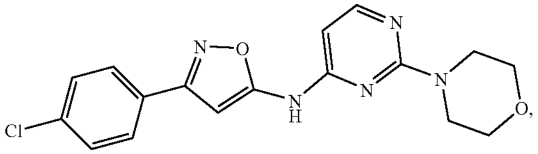

13

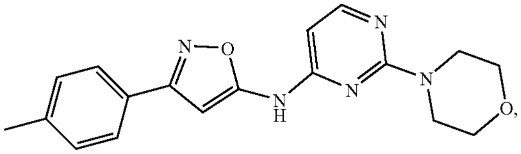

14

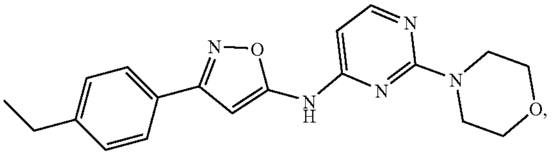

15

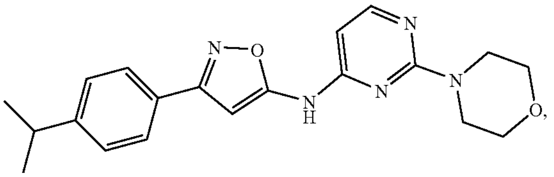

16

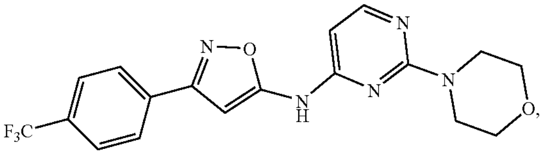

17

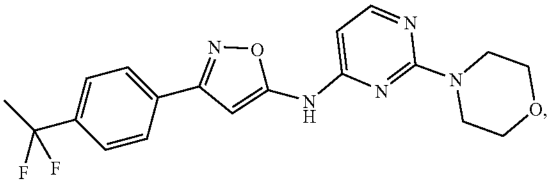

-continued
18
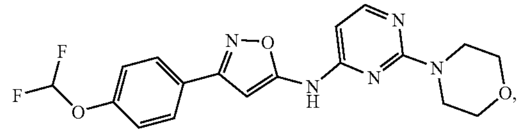
19
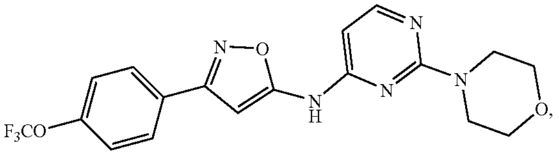
20
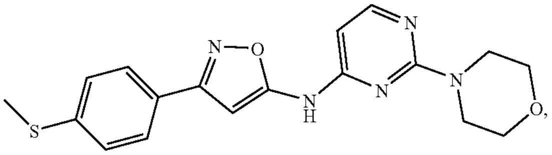
21
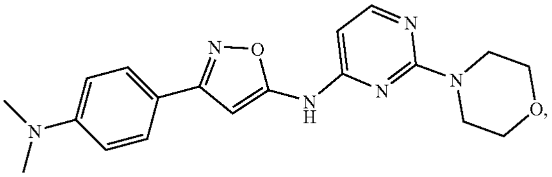
22
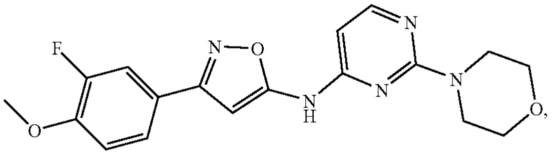
23
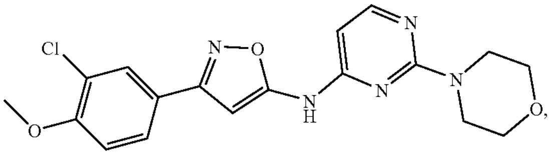
24
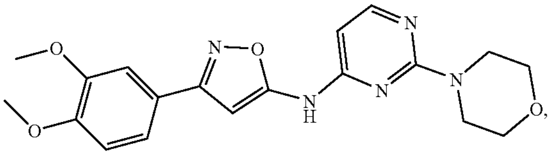
25
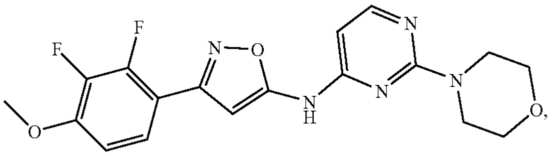
-continued
26
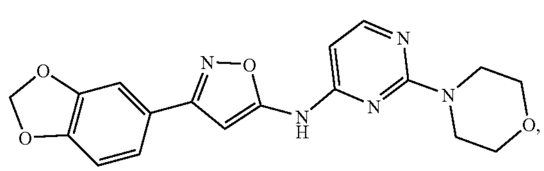
27
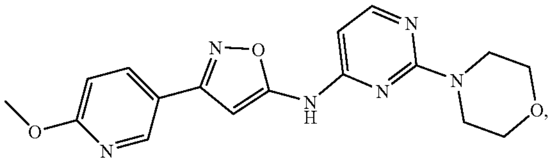
30
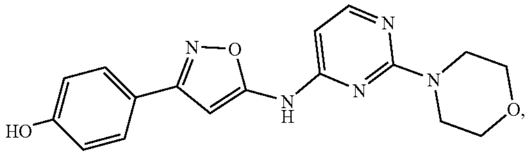
32
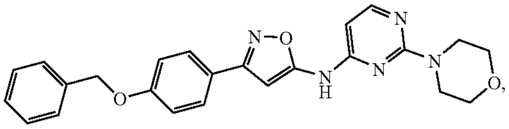
33
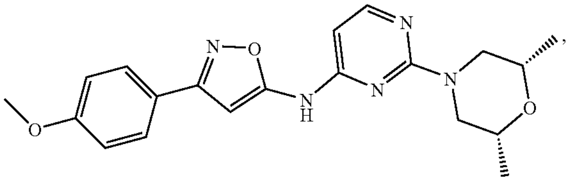
34
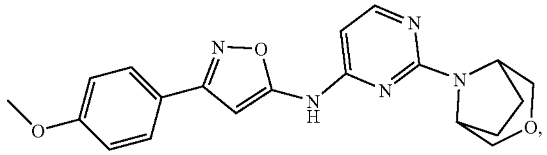
35
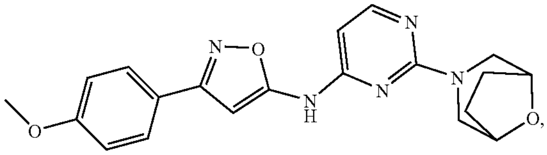
36
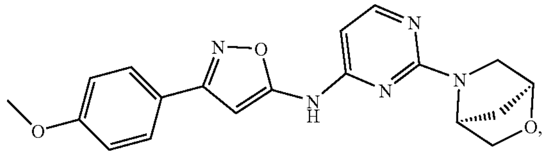

-continued
37
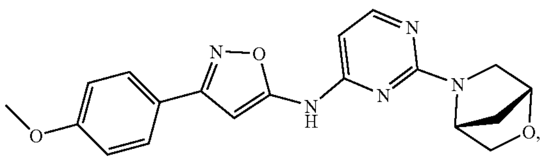
38
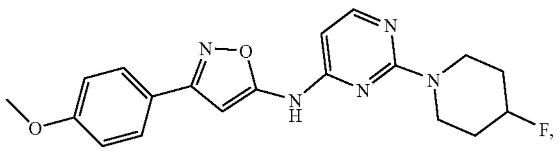
39
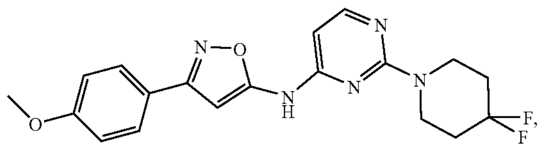
40
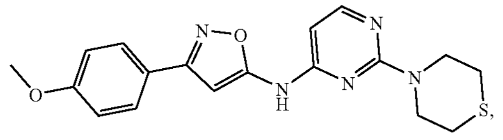
41
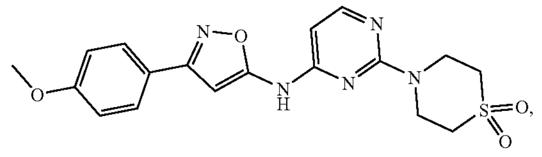
42
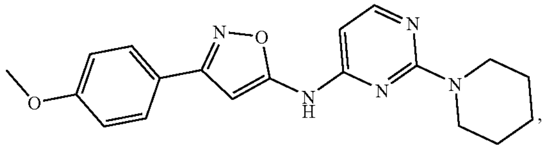
43
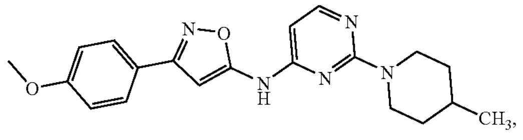
44
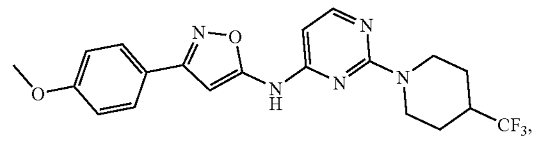
45
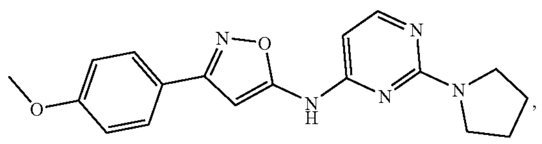
-continued
46
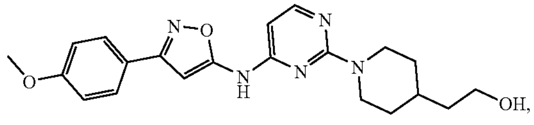
47
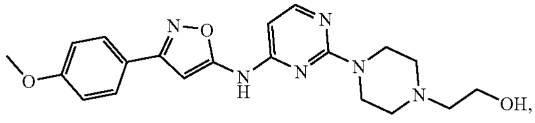
48
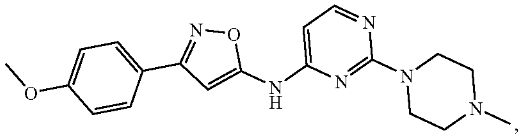
49
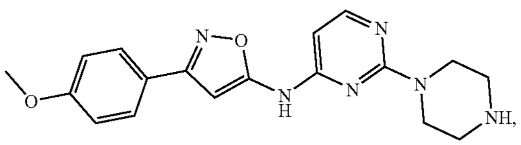
50
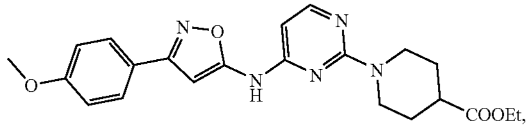
51
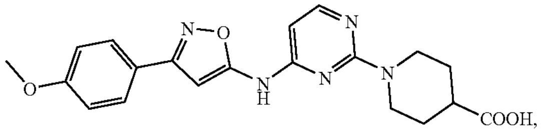
52
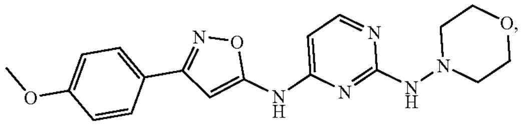
53
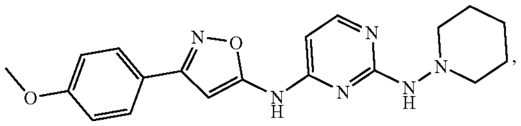
54
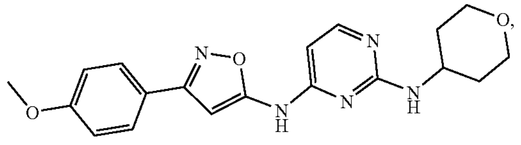
59
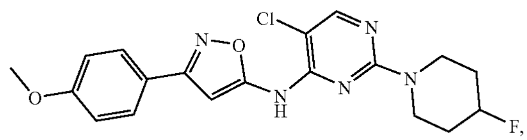

-continued
60
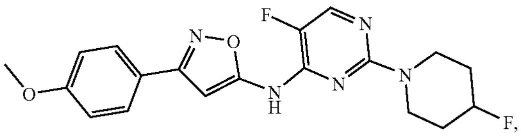,
61
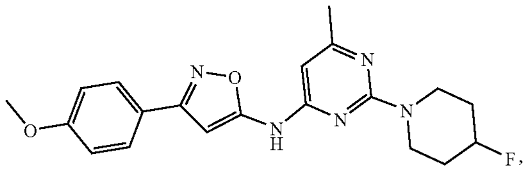,
62
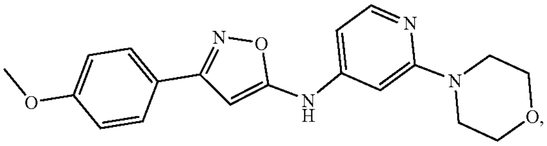,
63
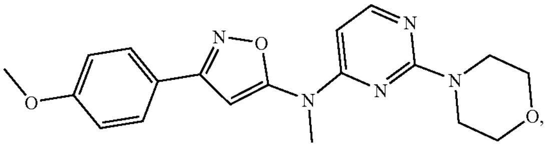,
64
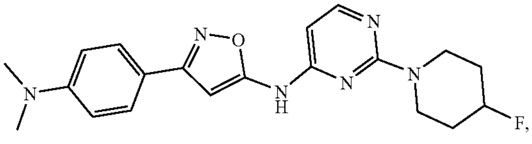,
65
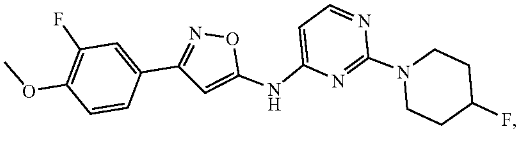,
66
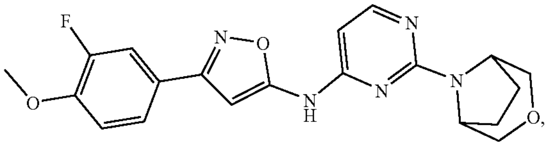,
67
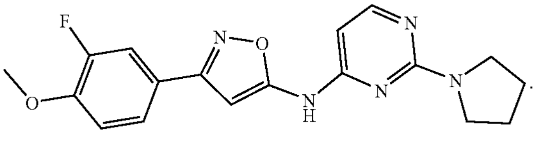.
In certain embodiments, the compound is selected from
68
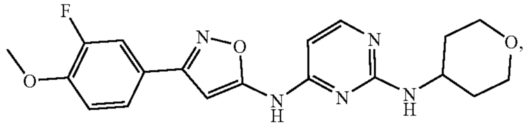,
69
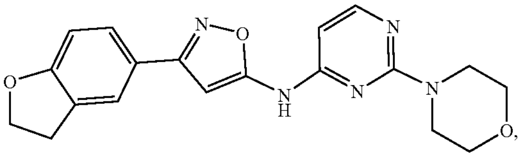,
70
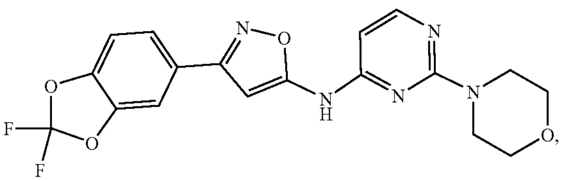,
71
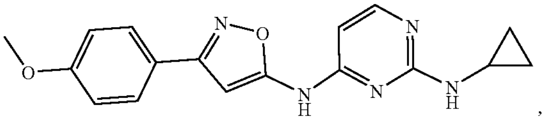,
72
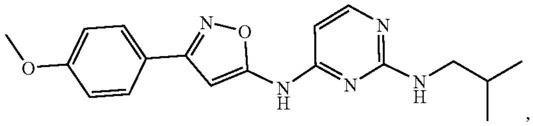,
73
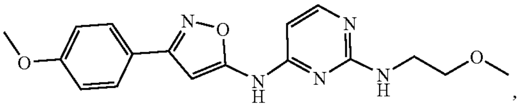,
74
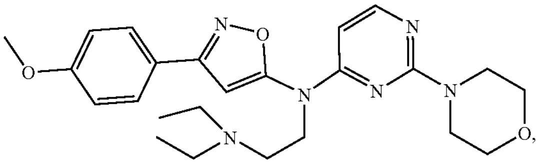,
75
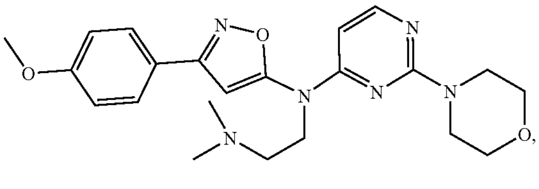, -continued
76
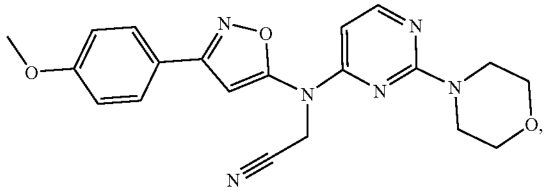
77
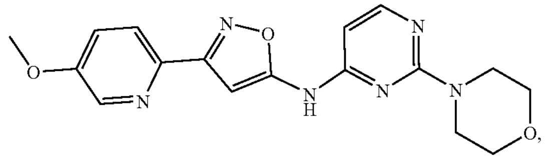
78
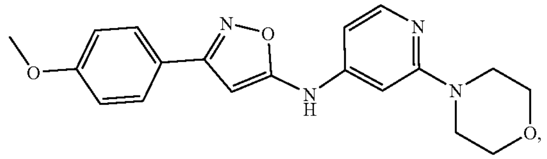
79
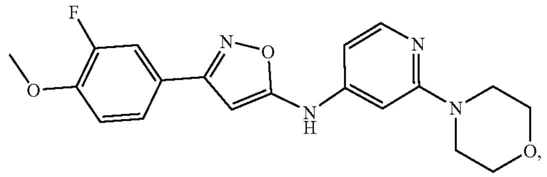
80
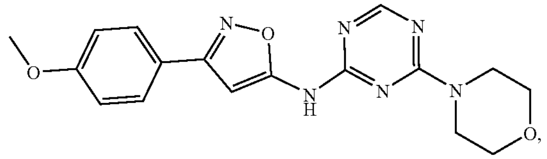
81
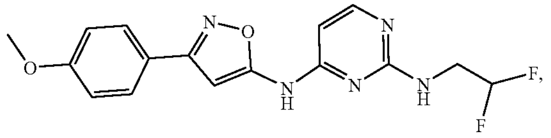
82
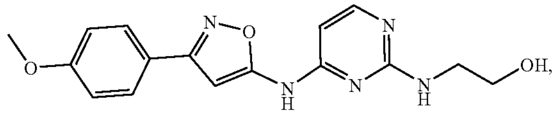
83
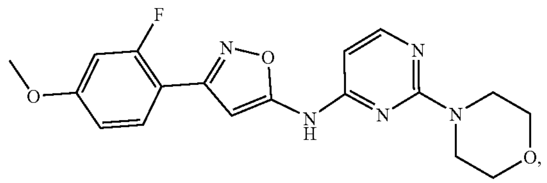
-continued
84
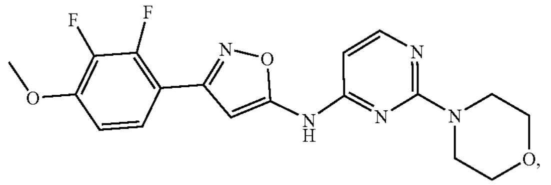
85
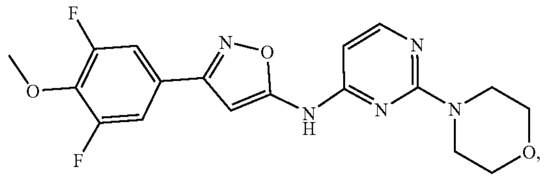
86
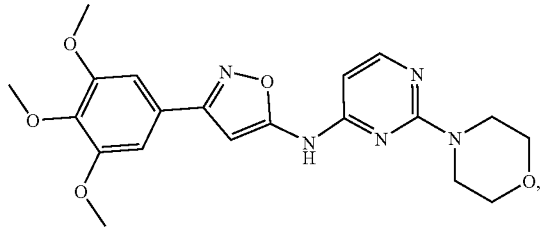
87
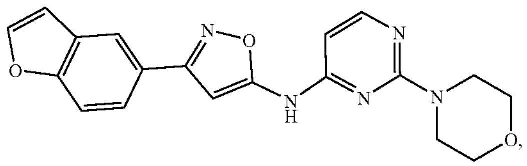
88
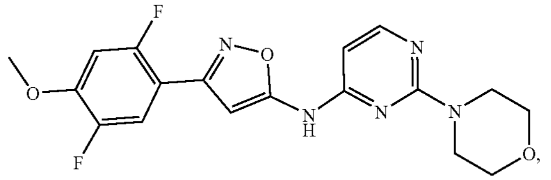
89
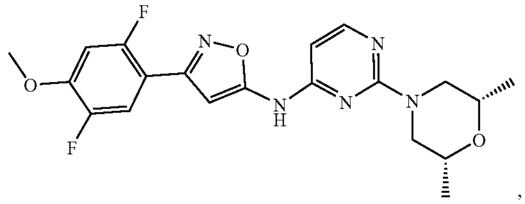
,
90
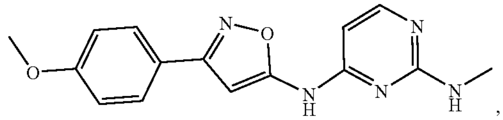
,
91
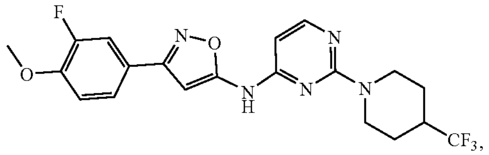

-continued
92
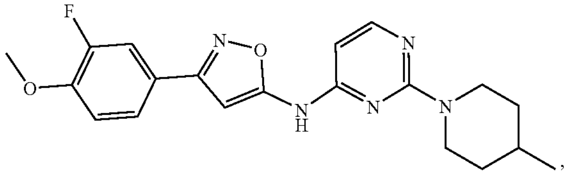
93
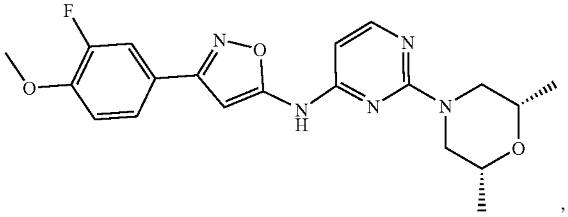
94
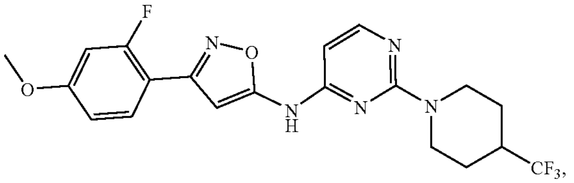
95
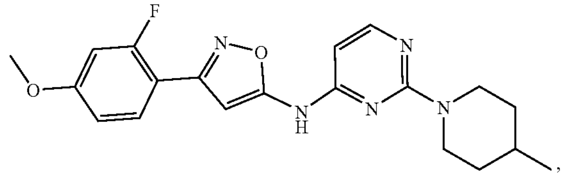
96
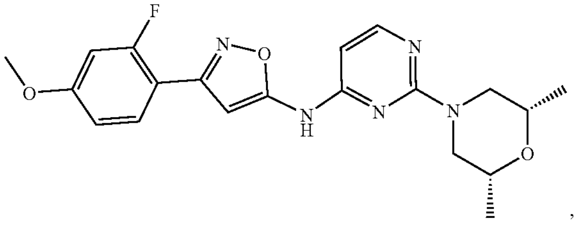
97
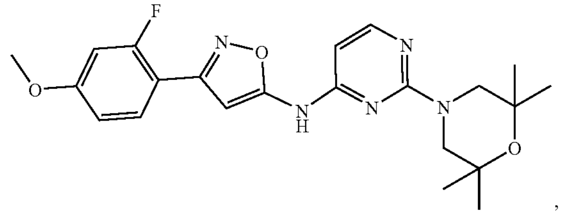
98
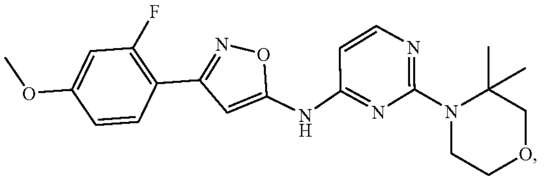
-continued
99
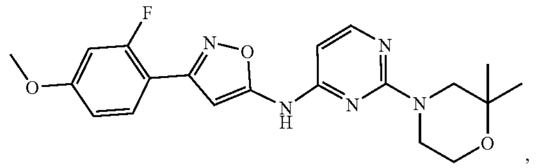
100
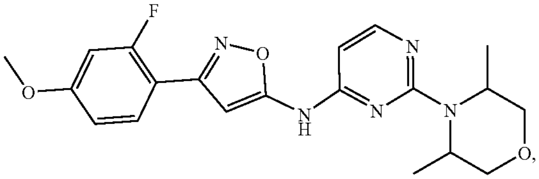
101
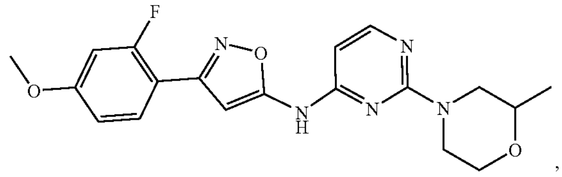
102
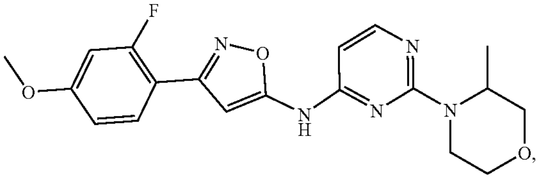
103
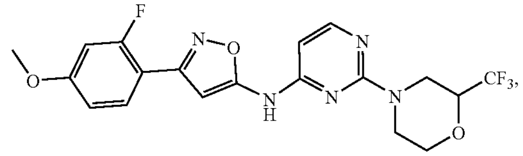
104
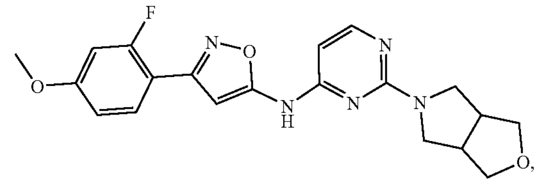
105
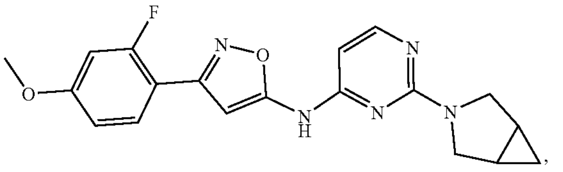
106
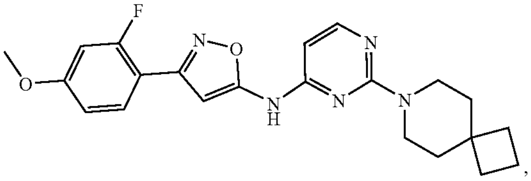

-continued
107
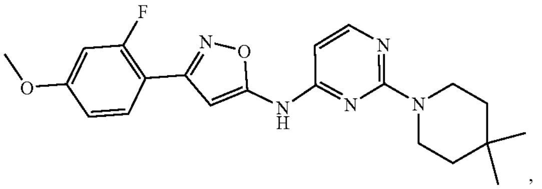
108
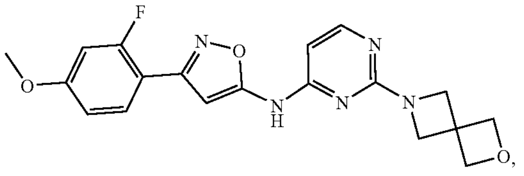
109
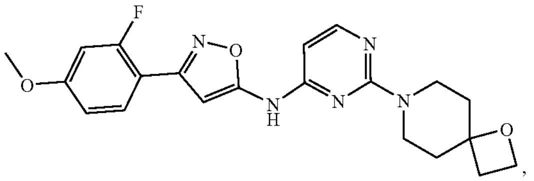
110
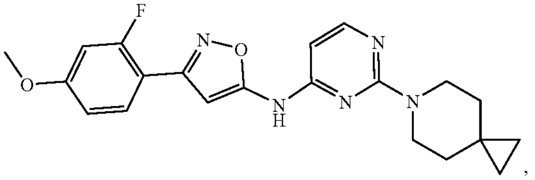
111
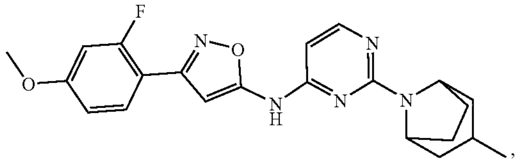
112
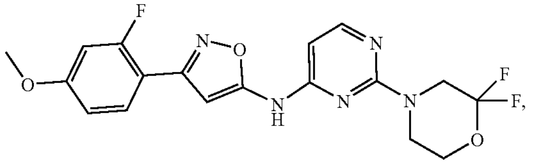
113
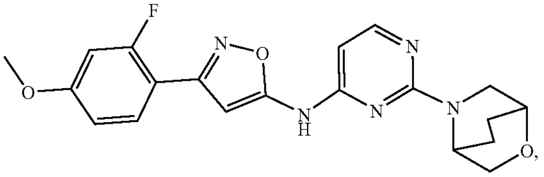
-continued
114
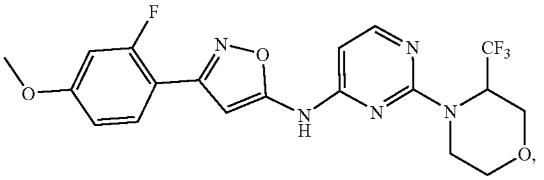
115
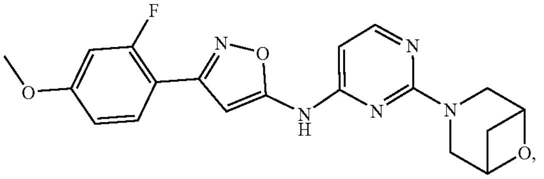
116
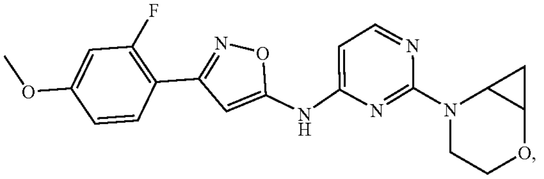
117
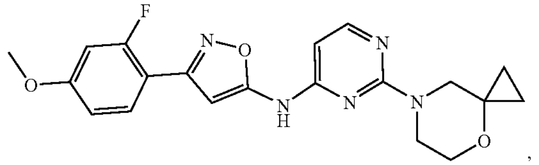
118
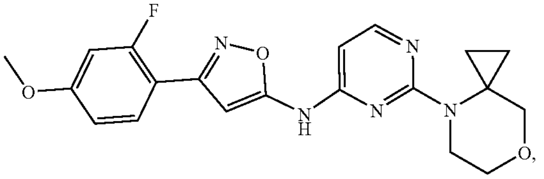
119
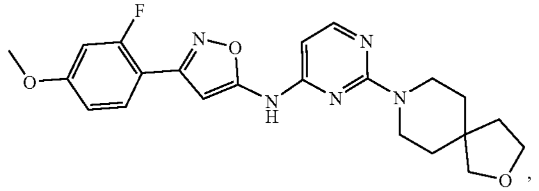
120
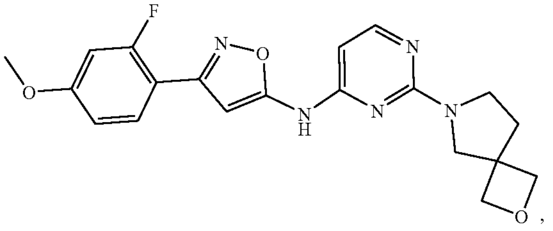

-continued

121

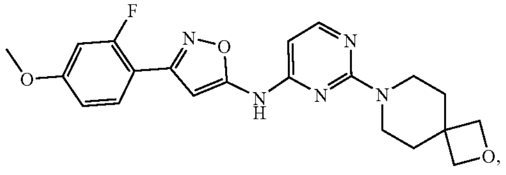

122

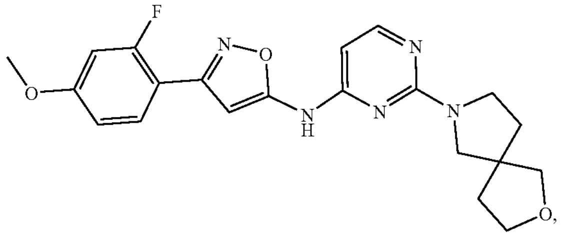

123

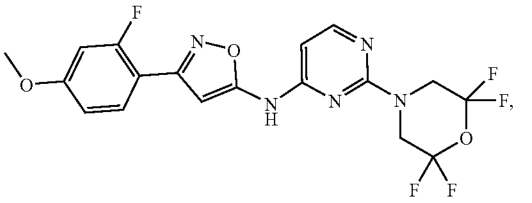

124

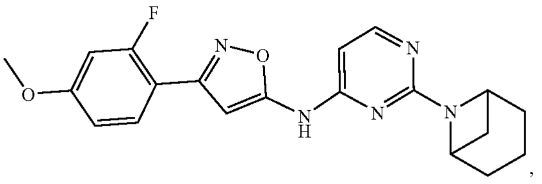

125

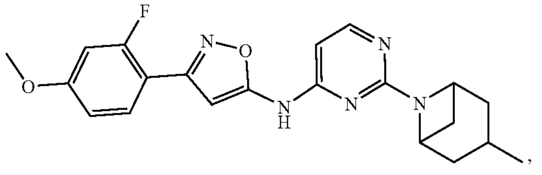

126

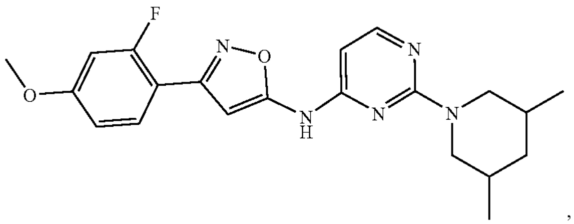

127

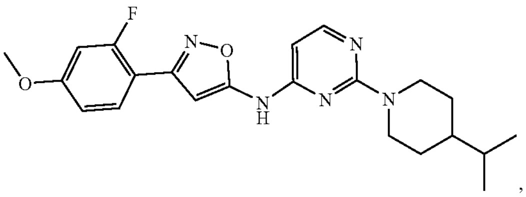

-continued

128

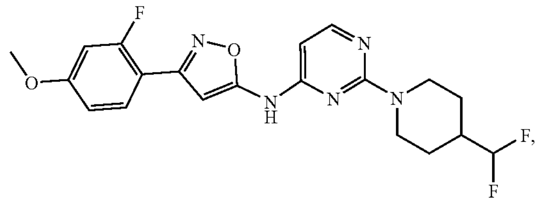

129

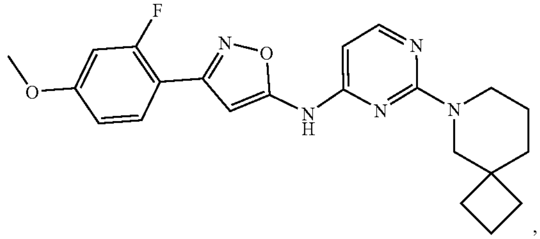

130

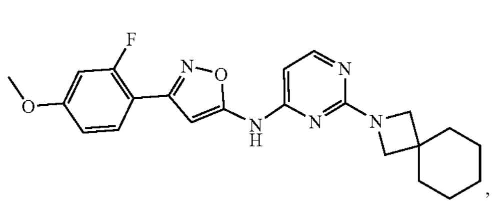

and

131

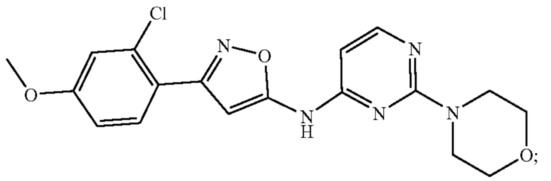

for a pharmaceutically acceptable salt thereof.

The compounds shown above are novel compounds, which have been synthesized by the present inventors. Hereinafter, synthesis methods for these novel compounds will be described. Representative compounds of the present disclosure in accordance with the general synthetic methods described below and are illustrated more particularly in the schemes that follow. Since the schemes are illustrations, the disclosure should not be construed as being limited by the chemical reactions and conditions expressed. The preparation of the various starting materials used in the schemes is well within the skill of persons versed in the art. The substituents for compounds of Formula (I) or a form thereof, represented in the schemes below, are as previously defined herein.

In another aspect, the present disclosure provides pharmaceutical compositions comprising a compound disclosed herein and a pharmaceutically acceptable excipient.

In yet another aspect, the present disclosure provides methods of treating a TACC3 mediated disease or disorder in a subject comprising administering a compound disclosed herein or a pharmaceutically acceptable salt thereof to the subject. In certain embodiments, the TACC3 mediated disease or disorder is cancer. In certain embodiments, the cancer is breast cancer, colon cancer, melanoma cancer, lung cancer, central nervous system cancer, ovarian cancer, leukemia cancer, renal cancer or prostate cancer. In certain embodiments, the cancer is a cancer selected from the NCI-60 panel.

In yet another aspect, the present disclosure provides methods of treating cancer in a subject comprising administering a compound disclosed herein or a pharmaceutically acceptable salt thereof to the subject. In certain embodiments, the cancer is breast cancer, colon cancer, melanoma cancer, lung cancer, central nervous system cancer, ovarian cancer, leukemia cancer, renal cancer or prostate cancer. In certain embodiments, the cancer is a cancer selected from the NCI-60 panel.

In yet another aspect, the present disclosure provides methods of making a compound of the disclosure, wherein the method is represented by Scheme I:

Scheme I

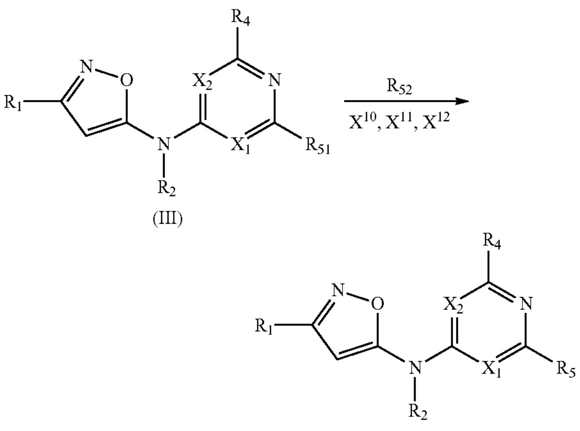

(III)

(I)

or a pharmaceutically acceptable salt thereof, wherein $X_1$ is N or $CR_6$;
$X_2$ is N or $CR_3$;
$R_1$ is aryl or heteroaryl;
$R_2$ is H or alkyl;
$R_3$, $R_4$ and $R_6$ are each independently H, alkyl, alkenyl, alkynyl, halo, hydroxyl, carboxyl, acyl, acetyl, ester, thioester, alkoxy, phosphoryl, amino, amide, cyano, nitro, azido, alkylthio, alkenyl, alkynyl, cycloalkyl, or sulfonamide;
$R_5$ is heterocyclyl, alkyl, or amino;
$R_{51}$ halo;
$R_{52}$ is heterocyclyl or alkyl;
$X^{10}$ is a base
$X^{11}$ is a noble metal catalyst; and
$X^{12}$ is phosphine ligand.

In certain embodiments, the base is a carbonate, an oxide, a tertiary amine, a secondary amine, or a hydride. In certain embodiments, the oxide is an alkoxide (e.g., tert-butoxide). In certain embodiments, the tertiary amine is a tertiary alkylamine (e.g., diisopropylethylamine). In certain embodiments, the hydride is a metal hydride (e.g., sodium hydride). In certain embodiments, the carbonate is a metal carbonate (e.g., cesium carbonate).

In certain embodiments, the noble metal catalyst is a palladium catalyst (e.g., palladium II acetate).

In certain embodiments, the phosphine catalyst is an arylphosphine (e.g., triphenylphosphine). In certain embodiments, the phosphine catalyst is Xantphos.

In certain embodiments, the method further comprises a solvent. In certain embodiments, the solvent is tertiary butanol, dimethyl acetamide, or dioxane.

In certain embodiments, the method further comprises heating.

In certain embodiments, the method is performed under an inert atmosphere.

Pharmaceutical Compositions

The compositions and methods of the present disclosure may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the disclosure and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the disclosure. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the disclosure, with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this disclosure, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present disclosure, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the disclosure may be used alone or conjointly administered with another type of therapeutic agent.

The present disclosure includes the use of pharmaceutically acceptable salts of compounds of the disclosure in the compositions and methods of the present disclosure. In certain embodiments, contemplated salts of the disclosure include, but are not limited to, alkyl, dialkyl, trialkyl or tetra-alkyl ammonium salts. In certain embodiments, contemplated salts of the disclosure include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the disclosure include, but are not limited to, Na, Ca, K, Mg, Zn or other metal salts. In certain embodiments, contemplated salts of the disclosure include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS.

The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present disclosure can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, $-OCO-CH_2-O$-alkyl, $-OP(O)(O\text{-alkyl})_2$ or —$CH_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

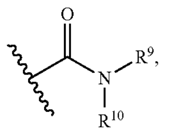

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

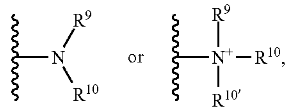

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

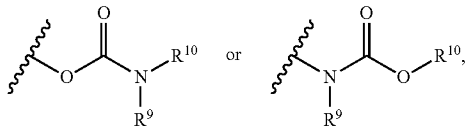

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group —$OCO_2$—.

The term "carboxy", as used herein, refers to a group represented by the formula —$CO_2H$.

The term "ester", as used herein, refers to a group —C(O)$OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —$OSO_3H$, or a pharmaceutically acceptable salt thereof.

The term "sulfonamide" is art-recognized and refers to the group represented by the general formulae

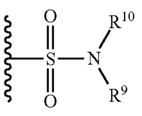 or 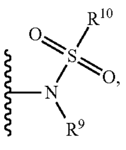, wherein $R^9$ and $R^{10}$ independently represents hydrogen or hydrocarbyl.

The term "sulfoxide" is art-recognized and refers to the group-S(O)—.

The term "sulfonate" is art-recognized and refers to the group $SO_3H$, or a pharmaceutically acceptable salt thereof.

The term "sulfone" is art-recognized and refers to the group —$S(O)_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group $-C(O)SR^9$ or $-SC(O)R^9$ wherein $R^9$ represents a hydrocarbyl.

The term "thioether", as used herein, is equivalent to an ether, wherein the oxygen is replaced with a sulfur.

The term "urea" is art-recognized and may be represented by the general formula

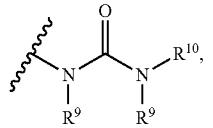

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "Log S" or "log S" as used herein is used in the art to quantify the aqueous solubility of a compound. The aqueous solubility of a compound significantly affects its absorption and distribution characteristics. A low solubility often goes along with a poor absorption. Log S value is a unit stripped logarithm (base 10) of the solubility measured in mol/liter.

EXAMPLES

The disclosure now being generally described, it will be more readily understood by reference to the following examples which are included merely for purposes of illustration of certain aspects and embodiments of the present disclosure, and are not intended to limit the disclosure.

Example 1: Exemplary Synthesis of Compounds of the Disclosure

Derivatives with R1 modifications when R2, R3 and R4 are H and R5 is morpholine in Formula (I)

The synthetic methodology for compounds 5-27 is shown in Scheme 1, comprising the following process steps:

i) The appropriate acid derivative was esterified by refluxing in EtOH (ethanol) in the presence of $SOCl_2$ (thionyl chloride) to produce compounds 1a-z, ii) The solution of compounds 1a-z in toluene was refluxed with acetonitrile in the presence of NaH (sodium hydride; 60% dispersion in mineral oil) to obtain the β-keto nitrile derivatives 2a-z, iii) Compounds 2a-z were reacted with $H_2N{\cdot}OH$ HCl (hydroxylamine hydrochloride) in aqueous NaOH (sodium hydroxide) solution at 100° C. to obtain isoxazol-5-amine analogues 3a-z, iv) Compounds 3a-z was reacted with 2,4-dichloropyrimidine or 4-chloro-2-(methylthio)pyrimidine (only for compound 28) in t-BuOH (tertiary butanol) in the presence of t-BuOK (potassium tertiary butoxide) at room temperature to obtain compounds 4a-z and compound 28, v) Compounds 4a-z in n-BuOH (butanol) were refluxed with morpholine to produce compounds 5-27.

Scheme 1. Synthesis of compound 5-28. Reagent conditions: (A) $SOCl_2$, EtOH, reflux, 3 h; (B) NaH, MeCN, toluene, reflux, 2 h; (C) $H_2N{\bullet}OH$ HCl, NaOH, $H_2O$, reflux, 4 h; (D) t-BuOK, 2,4-dichloropyrimidine, t-BuOH, rt, 24 h; (E) t-BuOK, 4-chloro-2-(methylthio)pyrimidine, t-BuOH, rt, 24 h; (F) Morpholine, n-BuOH, reflux, 5 h.

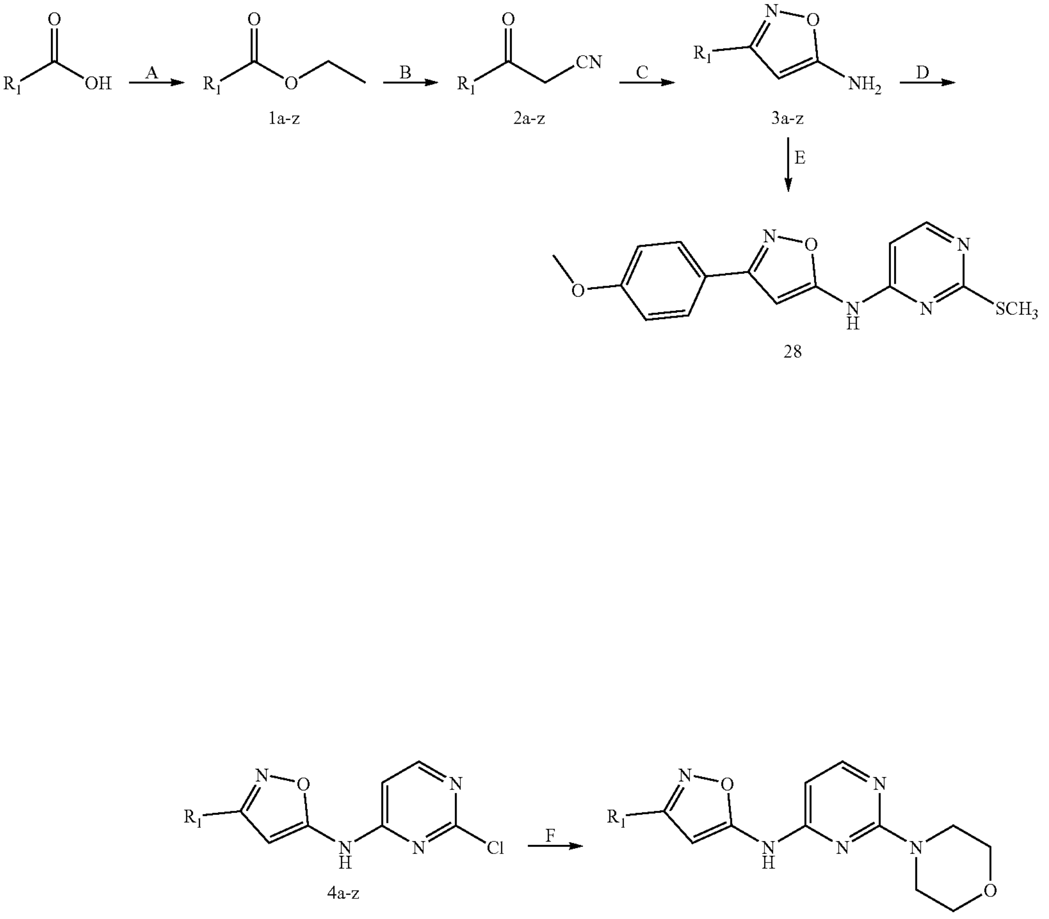

1a-z 2a-z 3a-z

28

4a-z 5-27

-continued $R_1$; a: 4-methoxyphenyl
b: 3-methoxyphenyl
c: 2-methoxyphenyl
d: Phenyl
e: 4-ethoxyphenl
f: 4-propoxyphenyl
g: 4-fluorophenyl
h: 4-chlorophenyl
i: 4-methylphenyl
j: 4-ethylphenyl
k: 4-isopropylphenyl
l: 4-trifluoromethylphenyl
m: 4-difluoroethylphenyl
n: 4-difluoroethoxyphenyl
o: 4-trifluoromethoxyphenyl
p: 4-thiomethylphenyl
r: 4-N,N-dimethylaminophenyl
s: 4-methoxy-3-fluorophenyl
t: 4-methoxy-3-chlorophenyl
u: 3,4-dimethoxyphenyl
v: 2,3-difluoro-4-methoxyphenyl
y: Piperonyl
z: 4-methoxypyridyl $R_1$; a: 4-methoxyphenyl
b: 3-methoxyphenyl
c: 2-methoxyphenyl
d: Phenyl
e: 4-ethoxyphenl
f: 4-propoxyphenyl
g: 4-fluorophenyl
h: 4-chlorophenyl
i: 4-methylphenyl
j: 4-ethylphenyl
k: 4-isopropylphenyl
l: 4-trifluoromethylphenyl
m: 4-difluoroethylphenyl
n: 4-difluoroethoxyphenyl
o: 4-trifluoromethoxyphenyl
p: 4-thiomethylphenyl
r: 4-N,N-dimethylaminophenyl
s: 4-methoxy-3-fluorophenyl
t: 4-methoxy-3-chlorophenyl
u: 3,4-dimethoxyphenyl
v: 2,3-difluoro-4-methoxyphenyl
y: Piperonyl
z: 4-methoxypyridyl The synthetic methodology for compound 30 is shown in Scheme 2, comprising the following process steps:

i) Demethylation of compound 4a in DCM (dichloromethane) in the presence of $BBr_3$ (boron tribromide) at 0° C. was conducted to obtain compound 29, ii) Compound 29 in n-BuOH was refluxed with morpholine to obtain compound 30.

The synthetic methodology for compound 32 is shown in Scheme 2, comprising the following process steps:

i) The reaction of compound 29 in dry THF (tetrahydrofuran) with benzyl alcohol in the presence of DIAD (diisopropyl azodicarboxylate) and $PPh_3$ (triphenylphosphine) at 0° C. produced compound 31, ii) Compound 31 in n-BuOH was refluxed with morpholine to obtain compound 32.

Scheme 2. Synthesis of compounds 30 and 32. Reagent and conditions: (A) $BBr_3$, DCM, 0 °C, 24 h; (B) Benzyl alcohol, DIAD, $PPh_3$, THF, 0 °C, 24 h; (C) Morpholine, n-BuOH, reflux, 5 h.

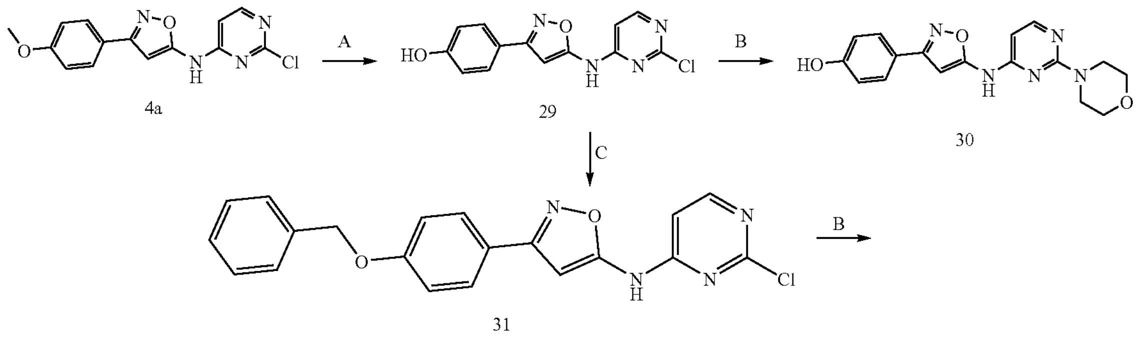

4a

29

30

31

-continued

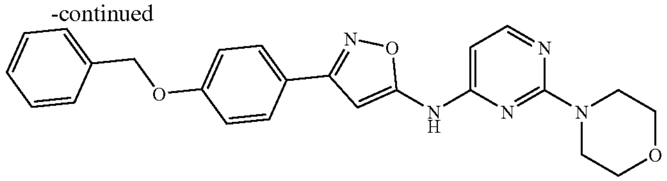

32

Derivatives with R5 modifications when R1 is 4-methoxyphenyl, R2, R3 and R4 are H in Formula (I)

For the synthesis of derivatives with $R_5$ modifications, synthetic procedures outlined in Scheme 3 were utilized. Hence, compound 4a or compound 28 were used as starting intermediates and then treated with various amines but not limited to such as morpholine, thiomorpholine, piperazine, piperidine and pyrrolidine as secondary amine derivatives or aminomorpholine, aminopiperidine and aminopyran derivatives as primary amine to afford the final compounds with Method A, B or C (33-54). If the amine derivatives were in the form of the HCl salt, Method B was used (for Compounds 34-39). If the amine derivatives were primary amine, Method C was used (for Compounds 52-54).

The synthetic methodology for compounds 33-54 is shown in Scheme 3, comprising the following process steps:

i) Compound 4a and the appropriate amine derivative, which is not in HCl (hydrogen chloride) salt form, was refluxed in BuOH to obtain compounds 33, 40-51 (Method A).

For compound 49, the N-Boc protected piperazine was used and then the protecting group was hydrolyzed with TFA (Trifluoroacetic acid) in DCM to obtain final compound 49. Also, compound 50 was hydrolyzed in THF:$H_2O$ in the presence of LiOH·$H_2O$ (lithium hydroxide monohydrate) under reflux to obtain compound 51.

ii) If the amine derivatives are in salt form, appropriate HCl salt of the amine was dissolved in BuOH in the presence of DIPEA (N,N-diisopropyl ethylamine) to obtain the free amine, which was iii) then reacted with Compound 4a under reflux to obtain final compounds 34-39 (Method B).

iv) If the amine derivatives are primary amines, compound 28 was used as a starting material, which was first treated with m-CPBA (meta-chloroperoxybenzoic acid) in DCM and then the sulfone intermediate obtained was reacted with the corresponding amine derivative to obtain final compounds 52-54 (Method C).

Scheme 3. Synthesis of compounds 33-54. Reagent and conditions: (A) Appropriate amine derivative, n-BuOH, reflux, 5 h; (B) Appropriate amine derivative, DIPEA, n-BuOH, reflux, 5 h; (C) i) m-CPBA, DCM, 0 °C, 2 h; ii) Appropriate amine derivative, n-BuOH, reflux, 5 h.

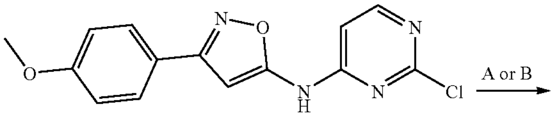

4a

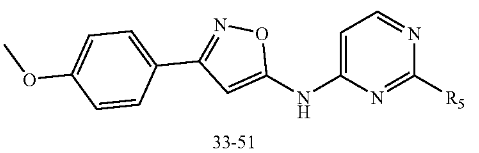

33-51

-continued

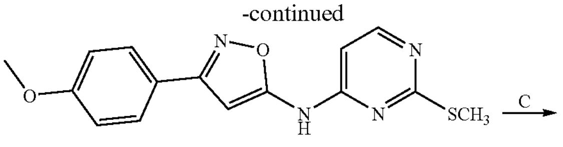

28

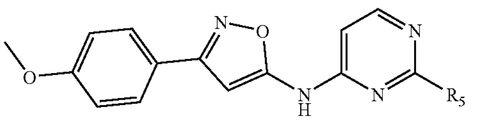

52-54

$R_5$; 33:

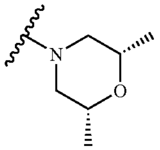

34:

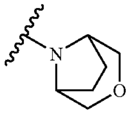

35:

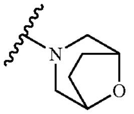

36:

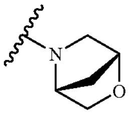

37:

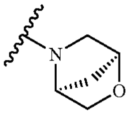

38:

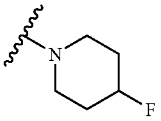

39:

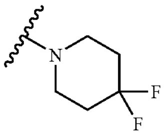

40:

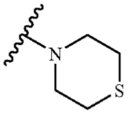

41:

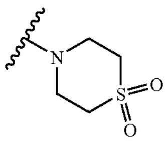

-continued

42: 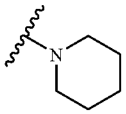

43: 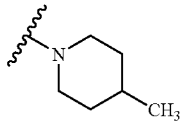

44: 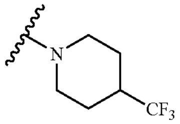

45: 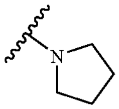

46: 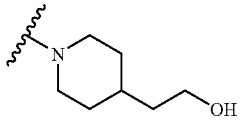

47: 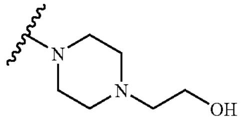

48: 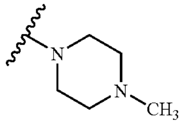

49: 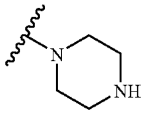

50: 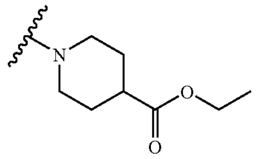

51: 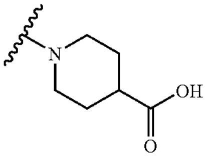

52: 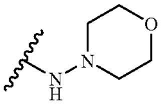

53: 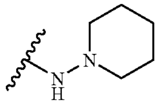

54: 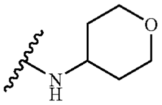

Derivatives with Pyrimidine Ring (X, R3, R4 Substitutions) Modification when R1 is 4-phenylmethoxy, R2 is H, and R5 is morpholine or 4-fluoropiperidine in Formula (I)

For derivatives with pyrimidine ring modifications, synthetic procedure outlined in Scheme 4 was utilized. Compound 3a was used as the starting material, which underwent a nucleophilic aromatic substitution reaction with various pyrimidine derivatives such as 2,4,5-trichloropyrimidine, 2,4-dichloro-5-fluoropyrimidine, 2,4-dichloro-6-methylpyrimidine or 2,4-dichloropyridine to obtain the final compounds 59-62.

The synthetic methodology for compounds 59-62 is shown in Scheme 4, comprising the following process steps:

i) Compound 3a was reacted with an appropriate pyrimidine derivative in t-BuOH in the presence of t-BuOK at room temperature to obtain compounds 55-57 (Method A). Compound 3a was reacted with 2,4-dichloropyridine in DMA (N,N-Dimethylacetamide) in the presence of NaH at room temperature to obtain compound 58 (Method B).

ii) Compounds 55-57 were reacted with 4-fluoropiperidine HCl in n-BuOH in the presence of DIPEA to produce compounds 59-61 (Method C).

iii) Compound 58 was treated with morpholine in dioxane in the presence of Xantphos (4,5-bis(diphenylphosphino)-9,9-dimethylxanthene), $Cs_2CO_3$ (cesium carbonate) and $Pd(OAc)_2$ (Palladium (II) acetate) at 100° C. for 30 minutes in microwave to obtain compound 62 (Method D).

Scheme 4. Synthesis of compound 59-62. Reagent and conditions: (A) Appropriate pyrimidine derivative, t-BuOK, t-BuOH, rt, 24 h; (B) 2,4-dichloropyridine, NaH, DMA, rt, 24 h; (C) 4-fluoropiperidine HCl, DIPEA, n-BuOH, reflux, 5 h; (D) Morpholine, $Cs_2CO_3$, Xantphos, $Pd(AOc)_2$, Dioxane, 100 °C, 30 min, microwave.

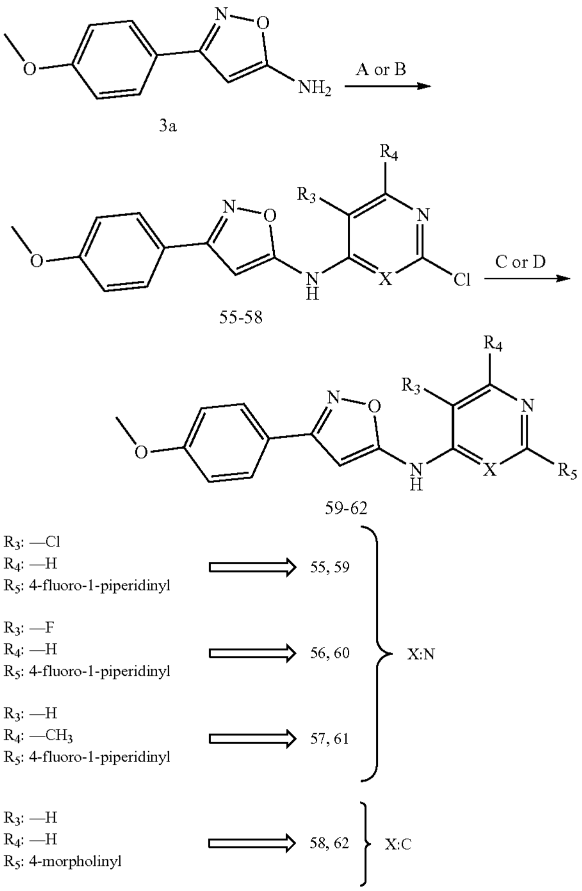

"N" Bridge Methylation (R2 Substitution) when R1 is 4-methoxyphenyl, R3 and R4 are H, and R5 is morpholine)

For the synthesis of compound 63, synthetic procedure outlined in Scheme 5 was utilized. Compound 5 was used as the starting material, which was alkylated to obtain the N-methylated derivative 63.

The synthetic methodology of compound 63 is shown in Scheme 5, comprising the following process step:

i) Compound 5 was dissolved in DMF (N,N-dimethyl formamide) and reacted with $CH_3I$ (methyl iodide) in the presence of $Cs_2CO_3$ at room temperature to obtain the compound 63.

Scheme 5. Synthesis of compound 63. Reagent and conditions: (A) $CH_3I$, $Cs_2CO_3$, DMF, rt, 2 h.

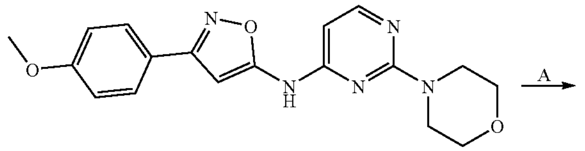

5

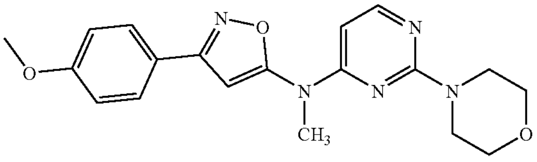

63

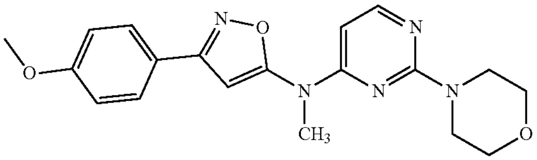

63

Synthesis of Compounds with Different Combinations of R1 and R5 in Formula (I) when R2, R3 and R4 are H According to the results obtained from the cytotoxicity studies, the $R_1$ and $R_2$ of some compounds with potent activity were combined in a new molecule and new compounds were obtained. For the synthesis of hybrid compounds, synthetic procedure outlined in Scheme 6 was utilized.

The synthetic method of compounds 64-67 is shown in Scheme 6, comprising the following process step:

i) Compound 4r or 4s and appropriate amine derivatives in BuOH were refluxed to obtain final compounds; if the amine derivatives are in salt form, appropriate HCl salt of the amine was dissolved in BuOH in the presence of DIPEA (N,N-diisopropyl ethylamine) to obtain the free amine, which was reacted with Compound 4r or 4s under reflux to obtain final compounds 64-66 (Method A).

ii) If the amine derivatives are not in the form of HCl salt, Compound 4s was treated with the amine derivative in n-BuOH to obtain final compound 67 (Method B).

Scheme 6. Synthesis of compounds 64-67. Reagent and conditions: (A) Appropriate amine derivative, DIPEA, n-BuOH, reflux, 5 h; (B) Appropriate amine derivative, n-BuOH, reflux, 5 h.

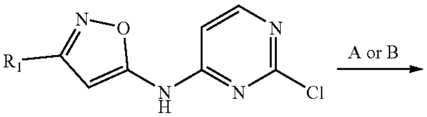

4r, 4s

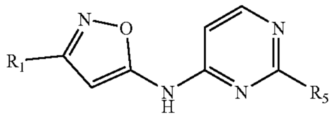

64-67

64 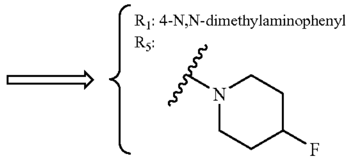

65 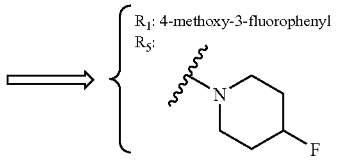

66 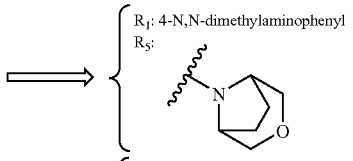

67 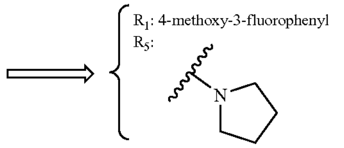

The embodiments of present disclosure include the chemical structures of the original intermediate compounds, which are reacted with amine derivatives described herein, but not limited to, for the synthesis of compounds of the general Formula (I), and can be selected from the compounds listed in Table 1.

TABLE 1

| Intermediate Compound No. | | Chemical Formula | Mass |
|---|---|---|---|
| 4a | 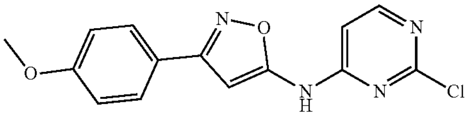 [SMILES: COc1ccc(-c2cc(Nc3ccnc(Cl)n3)on2)cc1] | $C_{15}H_{12}ClN_3O_2$ | 302.06 |

TABLE 1-continued
| | Intermediate Compound No. | Chemical Formula | Mass |
|---|---|---|---|
| 4b | 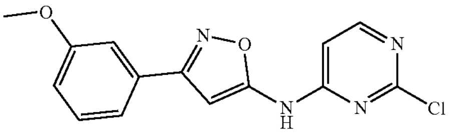 [SMILES: COc1cccc(-c2cc(Nc3ccnc(Cl)n3)on2)c1] | $C_{15}H_{12}ClN_3O_2$ | 302.06 |
| 4c | 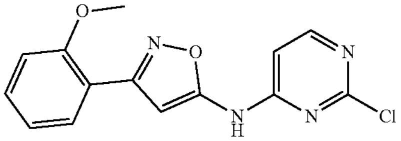 [SMILES: COc1ccccc1-c1cc(Nc2ccnc(Cl)n2)on1] | $C_{15}H_{12}ClN_3O_2$ | 302.06 |
| 4d | 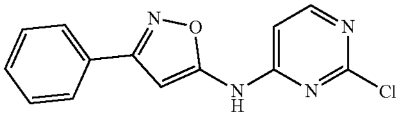 [SMILES: Clc1nccc(Nc2cc(-c3ccccc3)no2)n1] | $C_{13}H_9ClN_4O$ | 272.05 |
| 4e | 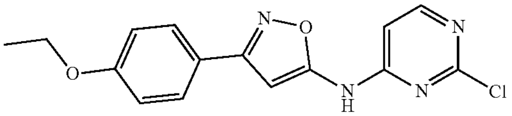 [SMILES: CCOc1ccc(-c2cc(Nc3ccnc(Cl)n3)on2)cc1] | $C_{16}H_{14}ClN_3O_2$ | 316.07 |
| 4f | 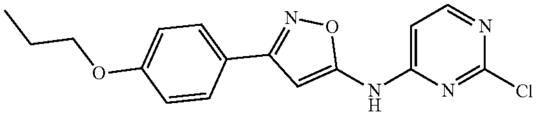 [SMILES: CCCOc1ccc(-c2cc(Nc3ccnc(Cl)n3)on2)cc1] | $C_{17}H_{16}ClN_3O_2$ | 330.09 |
| 4g | 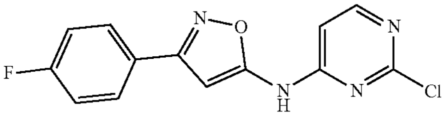 [SMILES: Fc1ccc(-c2cc(Nc3ccnc(Cl)n3)on2)cc1] | $C_{14}H_9ClFN_3O$ | 290.04 |
| 4h | 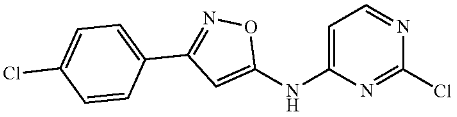 [SMILES: Clc1ccc(-c2cc(Nc3ccnc(Cl)n3)on2)cc1] | $C_{14}H_9Cl_2N_3O$ | 306.01 |
| 4i | 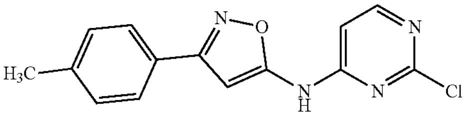 [SMILES: Cc1ccc(-c2cc(Nc3ccnc(Cl)n3)on2)cc1] | $C_{15}H_{12}ClN_3O$ | 286.06 |
| 4j | 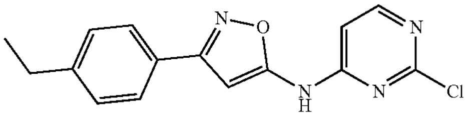 [SMILES: CCc1ccc(-c2cc(Nc3ccnc(Cl)n3)on2)cc1] | $C_{16}H_{14}ClN_3O$ | 300.08 |
| 4k | 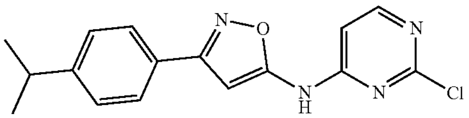 [SMILES: CC(C)c1ccc(-c2cc(Nc3ccnc(Cl)n3)on2)cc1] | $C_{17}H_{16}ClN_3O$ | 314.09 |
| 4l | 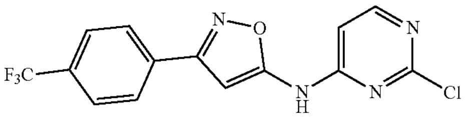 [SMILES: FC(F)(F)c1ccc(-c2cc(Nc3ccnc(Cl)n3)on2)cc1] | $C_{14}H_8ClF_3N_4O$ | 340.03 |
| 4m | 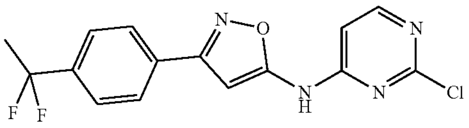 [SMILES: CC(F)(F)c1ccc(-c2cc(Nc3ccnc(Cl)n3)on2)cc1] | $C_{15}H_{11}ClF_2N_4O$ | 336.06 |

TABLE 1-continued
| Intermediate Compound No. | | Chemical Formula | Mass |
|---|---|---|---|
| 4n | 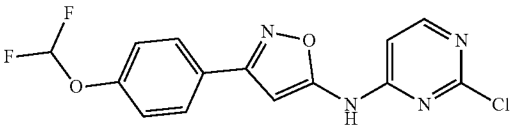 [SMILES: FC(F)Oc1ccc(-c2cc(Nc3ccnc(Cl)n3)on2)cc1] | $C_{14}H_9ClF_2N_4O_2$ | 338.04 |
| 4o | 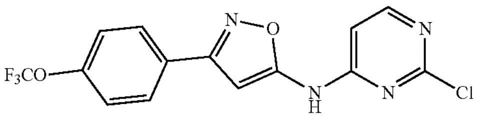 [SMILES: FC(F)(F)Oc1ccc(-c2cc(Nc3ccnc(Cl)n3)on2)cc1] | $C_{14}H_8ClF_3N_4O_2$ | 356.03 |
| 4p | 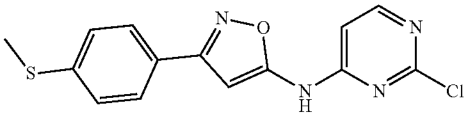 | $C_{14}H_{11}ClN_4OS$ | 318.03 |
| 4r | 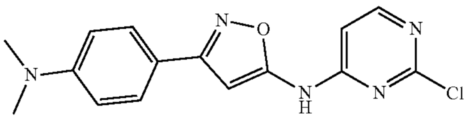 [SMILES: CN(C)c1ccc(-c2cc(Nc3ccnc(Cl)n3)on2)cc1] | $C_{15}H_{14}ClN_5O$ | 315.09 |
| 4s | 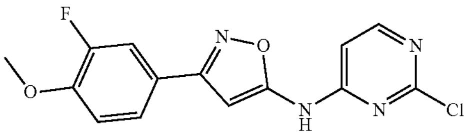 | $C_{14}H_{10}ClFN_4O_2$ | 320.05 |
| 4t | 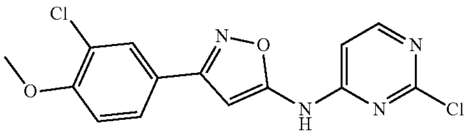 [SMILES: COc1ccc(-c2cc(Nc3ccnc(Cl)n3)on2)cc1F] | $C_{14}H_{10}C_{12}N_4O_2$ | 336.02 |
| 4u | 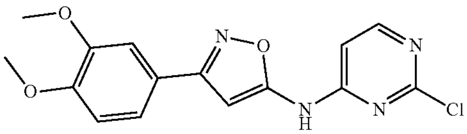 [SMILES: COc1ccc(-c2cc(Nc3ccnc(Cl)n3)on2)cc1OC] | $C_{15}H_{13}ClN_4O_3$ | 332.07 |
| 4v | 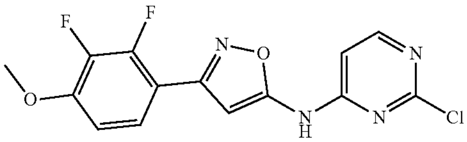 [SMILES: COc1ccc(-c2cc(Nc3ccnc(Cl)n3)on2)c(F)c1F] | $C_{14}H_9ClF_2N_4O_2$ | 338.04 |
| 4y | 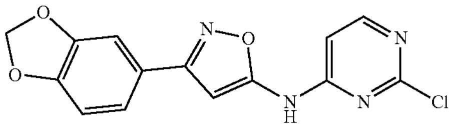 [SMILES: Clc1nccc(Nc2cc(-c3ccc4c(c3)OCO4)no2)n1] | $C_{14}H_9ClN_4O_3$ | 316.04 |
| 4z | 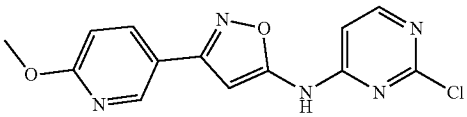 [SMILES: COc1ccc(-c2cc(Nc3ccnc(Cl)n3)on2)cn1] | $C_{13}H_{10}ClN_5O_2$ | 303.05 |
| 28 | 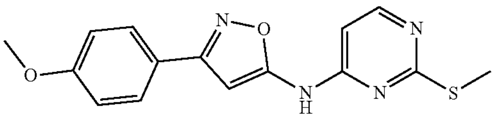 | $C_{15}H_{14}N_4O_2S$ | 314.08 |

TABLE 1-continued

| | Intermediate Compound No. | Chemical Formula | Mass |
|---|---|---|---|
| 29 | 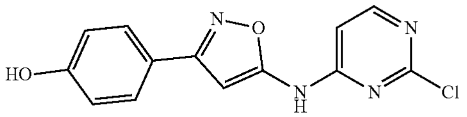 [SMILES: Oc1ccc(-c2cc(Nc3ccnc(Cl)n3)on2)cc1] | $C_{13}H_9ClN_4O_2$ | 288.04 |
| 31 | 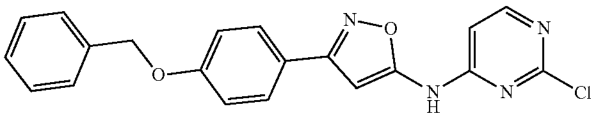 [SMILES: Clc1nccc(Nc2cc(-c3ccc(OCc4ccccc4)cc3)no2)n1] | $C_{20}H_{15}ClN_4O_2$ | 378.09 |
| 55 | 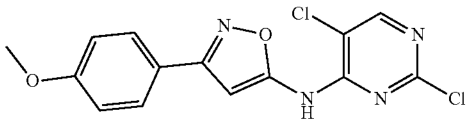 [SMILES: COc1ccc(-c2cc(Nc3nc(Cl)ncc3F)on2)cc1] | $C_{14}H_{10}C_{12}N_4O_2$ | 336.02 |
| 56 | 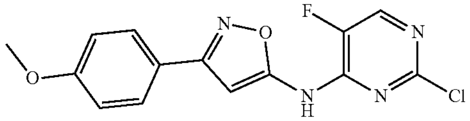 | $C_{14}H_{10}ClFN_4O_2$ | 320.05 |
| 57 | 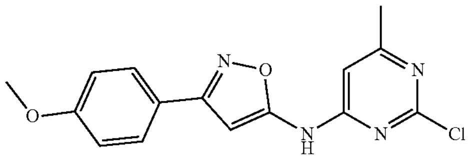 [SMILES: COc1ccc(-c2cc(Nc3cc(C)nc(Cl)n3)on2)cc1] | $C_{15}H_{13}ClN_4O_2$ | 316.07 |
| 58 | 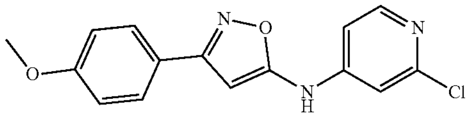 [SMILES: COc1ccc(-c2cc(Nc3ccnc(Cl)c3)on2)cc1] | $C_{15}H_{12}ClN_3O_2$ | 301.06 |
| 132 | 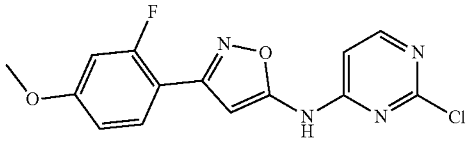 [SMILES: COc1ccc(-c2cc(Nc3ccnc(Cl)n3)on2)c(F)c1] | $C_{14}H_{10}ClFN_4O_2$ | 320.05 |
| 133 | 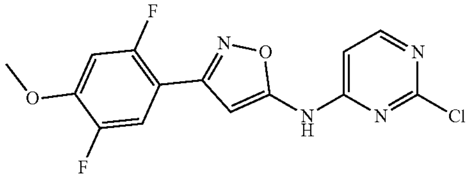 [SMILES: COc1cc(F)c(-c2cc(Nc3ccnc(Cl)n3)on2)cc1F] | $C_{14}H_9ClF_2N_4O_2$ | 338.04 |

The embodiment of the present disclosure includes compounds with characteristic $^1H$ NMR/$^{13}C$ NMR properties listed in Table 2.

TABLE 2

| Compd No | $^1H$ NMR/$^{13}C$ NMR |
|---|---|
| 5 | $^1H$ NMR (400 MHz, DMSO-d6): δ 3.68-3.70 (8H, m), 3.80 (3H, s), 6.24 (1H, d, J = 5.6 Hz), 6.54 (1H, s), 7.04 (2H, d, J = 9.0 Hz), 7.74 (2H, d, J = 9.0 Hz), 8.11 (1H, d, J = 5.6 Hz), 10.98 (1H, s). $^{13}C$ NMR (100 MHz, DMSO-d6): δ 44.10, 55.24, 65.99, 84.03, 97.00, 114.43, 121.43, 127.87, 157.38, 157.45, 160.61, 161.37, 162.13, 162.61. |

TABLE 2-continued

| Compd No | $^1$H NMR/$^{13}$C NMR |
|---|---|
| 6 | $^1$H NMR (400 MHz, DMSO-d6): δ 3.70-3.72 (8H, m), 3.83 (3H, s), 6.27 (1H, d, J = 5.6 Hz), 6.61 (1H, s), 7.06-7.45 (4H, m), 8.13 (1H, d, J = 5.6 Hz), 10.98 (1H, s). $^{13}$C NMR (100 MHz, DMSO-d6): δ 44.08, 55.12, 65.98, 84.51, 97.00, 111.27, 116.03, 118.77, 130.23, 130.34, 157.36, 157.52, 159.55, 161.35, 162.46, 162.86. |
| 7 | $^1$H NMR (400 MHz, DMSO-d6): δ 3.71-3.72 (8H, m), 3.85 (3H, s), 6.24 (1H, d, J = 5.6 Hz), 6.78 (1H, s), 7.05 (1H, td, J = 7.6 Hz, J = 1.6 Hz ), 7.18 (1H, d, J = 7.6 Hz), 7.47 (1H, td, J = 7.6 Hz, J = 1.6 Hz), 7.79 (1H, dd, J = 7.6 Hz, J = 1.6 Hz), 8.11 (1H, d, J = 5.6 Hz), 11.02 (1H, s). $^{13}$C NMR (100 MHz, DMSO-d6): δ 44.00, 55.50, 65.91, 87.93, 97.12, 112.27, 117.55, 120.68, 128.34, 131.41, 156.99, 157.28, 157.32, 160.17, 161.31, 161.92. |
| 8 | $^1$H NMR (400 MHz, DMSO-d6): δ 3.68-3.72 (8H, m), 6.26 (1H, d, J = 5.8 Hz), 6.60 (1H, s), 7.48-7.52 (3H, m), 7.80-7.82 (2H, m), 8.12 (1H, d, J = 5.8 Hz), 11.00 (1H, s). $^{13}$C NMR (100 MHz, DMSO-d6): δ 44.06, 65.91, 84.19, 96.93, 126.33, 128.96, 129.03, 129.97, 157.34, 157.43, 161.31, 162.47, 162.84. |
| 9 | $^1$H NMR (400 MHz, DMSO-d6): δ 1.34 (3H, t, J = 6.8 Hz), 3.70-3.71 (8H, m), 4.07 (2H, q, J = 6.8 Hz), 6.26 (1H, d, J = 5.6 Hz), 6.64 (1H, s), 7.02 (2H, d, J = 8.4 Hz), 7.73 (2H, d, J = 8.4 Hz), 8.12 (1H, d, J = 5.6 Hz), 10.99 (1H, s). $^{13}$C NMR (100 MHz, DMSO-d6): δ 14.54, 44.09, 63.18, 65.99, 83.99, 96.99, 114.83, 121.28, 127.86, 157.38, 157.44, 159.88, 161.36, 162.14, 162.58. |
| 10 | $^1$H NMR (400 MHz, DMSO-d6): δ 0.98 (3H, t, J = 7.0 Hz), 1.72-1.77 (2H, m), 3.70-3.71 (8H, m), 3.99 (2H, t, J = 7.0 Hz), 6.26 (1H, d, J = 5.6 Hz), 6.53 (1H, s), 7.04 (2H, d, J = 8.6 Hz), 7.72 (2H, d, J = 8.6 Hz), 8.12 (1H, d, J = 5.6 Hz), 10.93 (1H, s). $^{13}$C NMR (100 MHz, DMSO-d6): δ 10.23, 21.88, 44.08, 65.93, 69.06, 84.01, 96.93, 114.87, 121.28, 127.80, 157.39, 160.02, 161.33, 162.10, 162.57. |
| 11 | $^1$H NMR (400 Hz, DMSO-d6): δ 3.69-3.71 (8H, m), 6.26 (1H, d, J = 5.4 Hz), 6.59 (1H, s), 7.34 (2H, t, J = 8.7 Hz), 7.87 (2H, dd, J = 8.7 Hz, J = 5.4 Hz ), 8.13 (1H, d, J = 5.4 Hz), 11.03 (1H, s). $^{13}$C NMR (100 MHz, DMSO-d6): δ 44.09, 65.98, 84.22, 96.98, 116.02 (d, $^2J_{C-F}$ = 21.8 Hz), 125.60 (d, $^4J_{C-F}$ = 3.2 Hz), 128.71 (d, $^3J_{C-F}$ = 9 Hz), 157.34, 157.49, 161.35, 161.63, 162.97, 163.07 (d, $^1J_{C-F}$ = 245.6 Hz) |
| 12 | $^1$H NMR (400 MHz, DMSO-d6): δ 3.69-3.70 (8H, m), 6.27 (1H, d, J = 5.6 Hz), 6.61 (1H, s), 7.56 (2H, d, J = 8.2 Hz), 7.83 (2H, d, J = 8.2 Hz), 8.13 (1H, d, J = 5.6 Hz), 11.03 (1H, s). $^{13}$C NMR (100 MHz, DMSO-d6): δ 44.07, 65.94, 84.22, 96.94, 127.88, 128.15, 129.06, 134.67, 157.31, 157.49, 161.32, 161.54, 163.07. |
| 13 | $^1$H NMR (400 MHz, DMSO-d6): δ 2.36 (3H, s), 3.70-3.71 (8H, m), 6.26 (1H, d, J = 5.6 Hz), 6.56 (1H, s), 7.31 (2H, d, J = 7.8 Hz), 7.69 (2H, d, J = 7.8 Hz), 8.12 (1H, d, J = 5.6 Hz), 10.97 (1H, s). $^{13}$C NMR (100 MHz, DMSO-d6): δ 20.94, 44.10, 65.99, 84.18, 97.00, 126.28, 126.32, 129.60, 139.74, 157.38, 157.48, 161.36, 162.46, 162.74. |
| 14 | $^1$H NMR (400 MHz, DMSO-d6): δ 1.18 (3H, t, J = 7.6 Hz), 2.63 (2H, q, J = 7.6 Hz), 3.68-3.69 (8H, m), 6.24 (1H, d, J = 5.6 Hz), 6.56 (1H, s), 7.32 (2H, d, J = 8.4 Hz), 7.70 (2H, d, J = 8.4 Hz), 8.10 (1H, d, J = 5.6 Hz), 11.00 (1H, s). $^{13}$C NMR (100 MHz, DMSO-d6): δ 15.28, 27.93, 44.02, 65.91, 84.12, 96.93, 126.34, 126.46, 128.35, 145.87, 157.30, 157.40, 161.29, 162.39, 162.65. |
| 15 | $^1$H NMR (400 MHz, DMSO-d6): δ 1.24 (6H, d, J = 6.8 Hz), 2.95 (1H, h, J = 6.8 Hz), 3.70-3.73 (8H, m), 6.27 (1H, d, J = 5.2 Hz), 6.59 (1H, s), 7.39 (2H, d, J = 8.2 Hz), 7.74 (2H, d, J = 8.2 Hz), 8.13 (1H, d, J = 5.2 Hz), 11.04 (1H, s). $^{13}$C NMR (100 MHz, DMSO-d6): δ23.58, 33.25, 44.04, 65.92, 84.14, 96.96, 126.39, 126.62, 126.92, 150.44, 157.31, 157.41, 161.31, 162.40, 162.66. |
| 16 | $^1$H NMR (400 MHz, DMSO-d6): δ 3.70-3.71 (8H, m), 6.27 (1H, d, J = 5.2 Hz), 6.84 (1H, s), 7.86 (2H, d, J = 8.4 Hz), 8.03 (2H, d, J = 8.4 Hz), 8.13 (1H, d, J = 5.2 Hz), 11.07 (1H, s). |
| 17 | $^1$H NMR (400 MHz, DMSO-d6): δ 2.00 (3H, t, $J_{C-F}$ = 19 Hz), 3.70-3.71 (8H, m), 6.27 (1H, d, J = 5 .6 Hz), 6.66 (1H, s), 7.70 (2H, d, J = 8.6 Hz), 7.93 (2H, d, J = 8.6 Hz), 8.14 (1H, d, J = 5.6 Hz), 11.10 (1H, s). $^{13}$C NMR (100 MHz, DMSO-d6): δ 25.16 (t, $^2J_{C-F}$ = 28.6 Hz), 44.30, 66.19, 84.58, 97.23, 122.30 (t, $^1J_{C-F}$ = 236.6 Hz), 125.61 (t, $^2J_{C-F}$ = 26.7 Hz), 126.95, 130.86, 138.94, 157.53, 157.76, 161.56, 162.06, 163.32. |
| 18 | $^1$H NMR (400 MHz, DMSO-d6): δ 3.69-3.70 (8H, m), 6.25 (1H, d, J = 5.6 Hz), 7.30 (2H, d, J = 8.6 Hz), 7.33 (1H, t, $J_{C-F}$ = 74 Hz), 7.87 (2H, d, J = 8.6 Hz), 8.12 (1H, d, J = 5.6 Hz), 11.05 (1H, s). $^{13}$C NMR (100 MHz, DMSO-d6): δ 44.07, 65.96, 84.17, 96.98, 116.114 (t, $^1J_{C-F}$ = 256.5 Hz), 118.98, 125.92, 128.26, 152.11 (t, $^4J_{C-F}$ = 3.5 Hz), 157.30, 157.47, 161.33, 161.63, 162.93. |
| 19 | $^1$H NMR (400 MHz, DMSO-d6): δ 3.71 (8H, m), 6.27 (1H, d, J = 4.6 Hz), 6.64 (1H, s), 7.51 (2H, d, J = 7.6 Hz), 7.96 (2H, d, J = 7.6 Hz), 8.14 (1H, d, J = 4.6 Hz), 11.10 (1H, s). $^{13}$C NMR (100 MHz, DMSO-d6): δ 44.08, 65.96, 84.26, 96.99, 121.48, 128.27, 128.51, 149.36, 157.28, 157.51, 161.33, 161.40, 163.12. |
| 20 | $^1$H NMR (400 MHz, DMSO-d6): δ 2.50 (3H, s), 3.68-3.69 (8H, m), 6.23 (1H, d, J = 5.4 Hz), 6.56 (1H, s), 7.35 (2H, d, J = 8.0 Hz, 7.72 (2H, d, J = 8.0 Hz), 8.10 (1H, d, J = 5.4 Hz), 11.00 (1H, s). $^{13}$C NMR (100 MHz, DMSO-d6): δ 14.19, 44.04, 65.93, 84.03, 96.95, 125.22, 125.82, 126.74, 140.81, 157.29, 157.43, 161.29, 162.01, 162.74. |
| 21 | $^1$H NMR (400 MHz, DMSO-d6): δ 2.97 (6H, s), 3.70-3.71 (8H, m), 6.25 (1H, d, J = 5.4 Hz), 6.50 (1H, s), 6.79 (2H, d, J = 8.4 Hz), 7.62 (2H, d, J = 8.4 Hz), 8.12 (1H, d, J = 5.4 Hz), 10.93 (1H, s). $^{13}$C NMR (100 MHz, DMSO-d6): δ 40.23, 44.57, 66.44, 84.21, 97.46, 112.44, 116.60, 127.72, 151.77, 157.85, 157.88, 161.83, 162.64, 162.95. |

TABLE 2-continued

| Compd No | $^1$H NMR/$^{13}$C NMR |
|---|---|
| 22 | $^1$H NMR (400 MHz, DMSO-d6): δ 3.67-3.68 (8H, m), 3.87 (3H, s), 6.23 (1H, d, J = 5.4 Hz), 6.55 (1H, s), 7.24-7.28 (1H, m), 7.57-7.63 (2H, m), 8.10 (1H, d, J = 5.4 Hz), 11.00 (1H, s). $^{13}$C NMR (100 MHz, DMSO-d6): δ 44.04, 56.02, 65.96, 84.10, 96.93, 113.64 (d, $^2J_{C-F}$ = 19.2 Hz), 114.11, 121.76 (d, $^3J_{C-F}$ = 7.1 Hz), 123.26 (d, $^4J_{C-F}$ = 3.2 Hz), 148.51 (d, $^3J_{C-F}$ = 10.2 Hz), 151.40 (d, $^1J_{C-F}$ = 243.0 Hz), 157.31, 157.44, 161.31, 161.37 (d, $^2J_{C-F}$ = 19.0 Hz), 162.82. |
| 23 | $^1$H NMR (400 MHz, DMSO-d6): δ 3.67-3.68 (8H, m), 3.90 (3H, s), 6.24 (1H, d, J = 6.0 Hz), 6.58 (1H, s), 7.26 (1H, d, J = 8.6 Hz), 7.75 (1H, dd, J = 8.6 Hz, J = 2.0 Hz), 7.83 (1H, d, J = 2.0 Hz), 8.11 (1H, d, J = 6.0 Hz), 11.01 (1H, s). $^{13}$C NMR (100 MHz, DMSO-d6): δ 44.10, 56.32, 66.01, 84.18, 96.96, 113.21, 121.63, 122.34, 126.86, 127.47, 155.81, 157.38, 157.57, 161.24, 161.37, 162.91. |
| 24 | $^1$H NMR (400 MHz, DMSO-d6): δ 3.70-3.71 (8H, m), 3.81 (3H, s), 3.83 (3H, s), 6.25 (1H, d, J = 5.2 Hz), 6.61 (1H, s), 7.06 (1H, d, J = 8.4 Hz), 7.33-7.37 (2H, m), 8.12 (1H, d, J = 5.2 Hz), 11.00 (1H, s). $^{13}$C NMR (100 MHz, DMSO-d6): δ 44.08, 55.36, 55.53, 65.98, 84.32, 96.99, 109.22, 111.87, 119.37, 121.49, 148.90, 150.29, 157.36, 157.47, 161.36, 162.31, 162.57. |
| 25 | $^1$H NMR (400 MHz, DMSO-d6): δ 3.65-3.73 (8H, m), 3.85 (3H, s), 6.24 (1H, d, J = 5.4 Hz), 6.57 (1H, s), 7.08-7.52 (2H, m), 8.10 (1H, d, J = 5.4 Hz), 11.00 (1H, s). |
| 26 | $^1$H NMR (400 MHz, DMSO-d6): δ 3.67-3.68 (8H, m), 6.08 (2H, s), 6.23 (1H, d, J = 5.4 Hz), 6.51 (1H, s), 7.00-7.02 (1H, m), 7.29-7.32 (2H, m), 8.10 (1H, d, J = 5.4 Hz), 10.96 (1H, s). $^{13}$C NMR (100 MHz, DMSO-d6): δ 44.08, 66.00, 84.22, 96.97, 101.49, 106.30, 108.75, 120.92, 122.93, 147.83, 148.75, 157.38, 157.47, 161.36, 162.18, 162.67. |
| 27 | $^1$H NMR (400 MHz, DMSO-d6): δ 3.64-3.73 (8H, m), 3.73 (3H, s), 6.25 (1H, d, J = 5.6 Hz), 6.55 (1H, s), 6.73-8.03 (3H, m), 8.10 (1H, d, J = 5.4 Hz), 10.95 (1H, s). $^{13}$C NMR (100 MHz, DMSO-d6): δ 48.70, 54.13, 66.29, 96.96, 100.58, 110.60, 121.10, 134.60, 140.98, 149.50, 157.89, 158.90, 162.00, 163.21, 166.80. |
| 30 | $^1$H NMR (400 MHz, DMSO-d6): δ 3.67-3.68 (8H, m), 6.22 (1H, d, J = 5.2 Hz), 6.48 (1H, s), 6.85 (2H, d, J = 8.6 Hz), 7.61 (2H, d, J = 8.6 Hz), 8.09 (1H, d, J = 5.2 Hz), 9.86 (1H, s), 10.93 (1H, s). $^{13}$C NMR (100 MHz, DMSO-d6): δ 44.05, 65.94, 83.85, 96.93, 115.71, 119.78, 127.87, 157.35, 157.38, 159.03, 161.31, 162.31, 162.39. |
| 32 | $^1$H NMR (400 MHz, DMSO-d6): δ 3.60-3.65 (8H, m), 5.26 (2H, s), 6.46 (1H, d, J = 5.8 Hz), 6.74 (1H, s), 6.86 (2H, d, J = 8.8 Hz), 7.20-7.32 (5H, m), 7.66 (2H, d, J = 8.8 Hz), 8.15 (1H, d, J = 5.8 Hz), 10.00 (1H, s). $^{13}$C NMR (100 MHz, DMSO-d6): δ 43.94, 50.38, 65.87, 89.76, 96.45, 115.75, 119.38, 126.84, 127.16, 127.94, 128.48, 137.31, 158.36, 159.28, 159.46, 160.88, 162.75, 165.05. |
| 33 | $^1$H NMR (400 MHz, DMSO-d6): δ 1.16 (3H, s), 1.18 (3H, s), 2.54-2.60 (2H, m), 3.57-3.61 (2H, m), 3.82 (3H, s), 4.46-4.49 (2H, m), 6.24 (1H, d, J = 5.2 Hz), 6.58 (1H, s), 7.05 (2H, d, J = 8.8 Hz), 7.72 (2H, d, J = 8.8 Hz), 8.11 (1H, d, J = 5.2 Hz), 10.96 (1H, s). $^{13}$C NMR (100 MHz, DMSO-d6): δ 18.66, 49.14, 55.22, 70.82, 84.19, 96.71, 114.36, 121.42, 127.55, 157.27, 157.43, 160.60, 160.89, 161.95, 162.55. |
| 34 | $^1$H NMR (400 MHz, DMSO-d6): δ 1.92-2.00 (4H, m), 3.60 (2H, d, J = 10.6 Hz), 3.67 (2H, d, J = 10.6 Hz), 3.82 (3H, s), 4.59 (2H, m), 6.26 (1H, d, J = 5.6 Hz), 6.51 (1H, s), 7.06 (2H, d, J = 9.0 Hz), 7.73 (2H, d, J = 9.0 Hz), 8.12 (1H, d, J = 5.6 Hz), 10.97 (1H, s). $^{13}$C NMR (100 MHz, DMSO-d6): δ 26.62, 55.05, 55.24, 70.31, 83.88, 97.14, 114.47, 121.43, 127.83, 157.60, 157.80, 160.05, 160.61, 162.11, 162.63. |
| 35 | $^1$H NMR (400 MHz, DMSO-d6): δ 1.67-1.83 (4H, m), 3.12 (2H, d, J = 12.0 Hz), 3.82 (3H, s), 4.15 (2H, d, J = 12.8 Hz), 4.44 (2H, m), 6.23 (1H, d, J = 5.6 Hz), 6.55 (1H, s), 7.06 (2H, d, J = 9.0 Hz), 7.74 (2H, d, J = 9.0 Hz), 8.08 (1H, d, J = 5.6 Hz), 10.97 (1H, s). $^{13}$C NMR (100 MHz, DMSO-d6): δ 27.49, 49.59, 55.19, 72.78, 83.91, 96.81, 114.39, 121.37, 127.80, 157.12, 157.27, 160.54, 162.05, 162.16, 162.57. |
| 36 | $^1$H NMR (400 MHz, DMSO-d6): δ 1.87-1.98 (2H, m), 3.50-3.70 (4H, m), 3.81 (3H, s), 4.69-4.93 (2H, m), 6.21 (1H, d, J = 5.6 Hz), 6.57 (1H, s), 7.05 (2H, d, J = 8.8 Hz), 7.74 (2H, d, J = 8.8 Hz), 8.06 (1H, d, J = 5.6 Hz), 10.99 (1H, s). |
| 37 | $^1$H NMR (400 MHz, DMSO-d6): δ 1.89-1.93 (2H, m), 3.49-3.72 (4H, m), 3.82 (3H, s), 4.69-4.94 (2H, m), 6.22 (1H, d, J = 4.6 Hz), 6.64 (1H, s), 7.06 (2H, d, J = 8.4 Hz), 7.75 (2H, d, J = 8.4 Hz), 8.07 (1H, d, J = 4.6 Hz), 10.94 (1H, s). |
| 38 | $^1$H NMR (400 MHz, DMSO-d6): δ 1.74-1.98 (4H, m), 3.73-3.95 (7H, m), 4.87-4.99 (1H, m), 6.22 (1H, d, J = 5.4 Hz), 6.55 (1H, s), 7.07 (2H, d, J = 8.8 Hz), 7.73 (2H, d, J = 8.8 Hz), 8.11 (1H, d, J = 5.4 Hz), 10.98 (1H, s). $^{13}$C NMR (100 MHz, DMSO-d6): δ 30.68 (d, $^2J_{C-F}$ = 19.1 Hz), 55.25, 83.86, 88.85 (d, $^1J_{C-F}$ = 168.4 Hz), 96.58, 114.50, 121.43, 127.77, 157.46, 157.64, 160.63, 161.01, 162.09, 162.71. |
| 39 | $^1$H NMR (400 MHz, DMSO-d6): δ 1.98-2.10 (4H, m), 3.83 (3H, s), 3.92-3.94 (4H, m), 6.29 (1H, d, J = 5.6 Hz), 6.55 (1H, s), 7.07 (2H, d, J = 8.8 Hz), 7.76 (2H, d, J = 8.8 Hz), 8.14 (1H, d, J = 5.6 Hz), 11.04 (1H, s). $^{13}$C NMR (100 MHz, DMSO-d6): δ 33.05 (t, $^2J_{C-F}$ = 22.5 Hz), 40.67, 55.24, 83.98, 97.14, 114.47, 121.39, 123.17 (t, $^1J_{C-F}$ = 239.6 Hz), 127.86, 157.55, 157.66, 160.63, 160.73, 162.13, 162.60. |
| 40 | $^1$H NMR (400 MHz, DMSO-d6): δ 2.62-2.65 (4H, m), 3.80 (3H, s), 4.06-4.08 (4H, m), 6.21 (1H, d, J = 5.6 Hz), 6.49 (1H, s), 7.04 (2H, d, J = 8.8 Hz), 7.71 (2H, d, J = 8.8 Hz), 8.10 (1H, d, J = 5.6 Hz), 10.99 (1H, s). $^{13}$C NMR (100 MHz, DMSO-d6): δ 25.85, 46.34, 55.24, 83.85, 96.61, 114.49, 121.39, 127.80, 157.46, 157.63, 160.62, 160.67, 162.09, 162.66. |

TABLE 2-continued

| Compd No | $^1$H NMR/$^{13}$C NMR |
|---|---|
| 41 | $^1$H NMR (400 MHz, DMSO-d6): δ 3.19-3.21 (4H, m), 3.80 (3H, s), 4.22 (4H, m), 6.32 (1H, d, J = 5.32 Hz), 6.47 (1H, s), 7.04 (2H, d, J = 9.0 Hz), 7.75 (2H, d, J = 9.0 Hz), 8.15 (1H, d, J = 5.6 Hz), 8.15 (1H, d, J = 5.6 Hz), 11.08 (1H, s). $^{13}$C NMR (100 MHz, DMSO-d6): δ 42.46, 50.54, 55.24, 84.04, 97.80, 114.45, 121.30, 127.95, 157.65, 157.68, 160.19, 160.63, 162.15, 162.47. |
| 42 | $^1$H NMR (400 MHz, DMSO-d6): δ 1.54-1.64 (6H, m), 3.75-3.77 (4H, m), 3.81 (3H, s), 6.17 (1H, d, J = 5.8 Hz), 6.55 (1H, s), 7.07 (2H, d, J = 8.8 Hz), 7.71 (2H, d, J = 8.8 Hz), 8.08 (1H, d, J = 5.8 Hz), 10.92 (1H, s). $^{13}$C NMR (100 MHz, DMSO-d6): δ 24.33, 25.18, 44.57, 55.24, 83.72, 95.97, 114.49, 121.47, 127.68, 157.33, 157.56, 160.61, 161.08, 162.03, 162.81. |
| 43 | $^1$H NMR (400 MHz, DMSO-d6): δ 0.90 (3H, d, J = 6.0 Hz), 1.05-1.07 (2H, m), 1.62-1.69 (3H, m), 2.87-2.93 (2H, m), 3.80 (3H, s), 4.58-4.61 (2H, m), 6.16 (1H, d, J = 5.4 Hz), 6.52 (1H, s), 7.05 (2H, d, J = 9.0 Hz), 7.69 (2H, d, J = 9.0 Hz), 8.06 (2H, d, J = 5.4 Hz), 10.86 (1H, s). $^{13}$C NMR (100 MHz, DMSO-d6): δ 21.66, 30.57, 33.36, 43.85, 55.18, 83.70, 95.96, 114.44, 121.45, 127.60, 157.60, 157.30, 157.48, 160.57, 161.05, 161.97, 162.75. |
| 44 | $^1$H NMR (400 MHz, DMSO-d6): δ 1.34-1.44 (2H, m), 1.89-1.92 (2H, m), 2.61-2.64 (1H, m), 3.79 (3H, s), 4.72-4.75 (2H, m), 6.21 (1H, d, J = 5.4 Hz), 6.52 (1H, s), 7.05 (2H, d, J = 8.8 Hz), 7.72 (2H, d, J = 8.8 Hz), 8.09 (1H, d, J = 5.4 Hz), 10.97 (1H, s). $^{13}$C NMR (100 MHz, DMSO-d6): δ 23.72, 42.30, 55.19, 83.83, 96.65, 114.42, 121.38, 127.63 (q, $^1J_{C-F}$ = 275.8 Hz), 127.74, 157.38, 157.54, 160.58, 160.96, 162.05, 162.60. |
| 45 | $^1$H NMR (400 MHz, DMSO-d6): δ 1.88-1.98 (4H, m), 3.41-3.61 (4H, m), 3.80 (3H, s), 6.12 (1H, d, J = 5.8 Hz), 6.12 (1H, d, J = 5.8 Hz), 6.68 (1H, s), 7.04 (2H, d, J = 9.0 Hz), 7.70 (2H, d, J = 9.0 Hz), 8.03 (1H, d, J = 5.8 Hz), 10.90 (1H, s). $^{13}$C NMR (100 MHz, DMSO-d6): δ 24.98, 46.18, 55.18, 83.87, 95.57, 114.40, 121.52, 127.67, 156.94, 157.32, 159.75, 160.51, 162.01, 162.73. |
| 46 | $^1$H NMR (400 MHz, DMSO-d6): δ 1.07-1.16 (2H, m), 1.35-1.40 (2H, m), 1.67-1.75 (3H, m), 2.87-2.93 (2H, m), 3.46 (2H, q, J = 8.6 Hz), 3.81 (3H, s), 4.36 (1H, t, J = 8.6 Hz), 4.61-4.64 (2H, m), 6.16 (1H, d, J = 5.6 Hz), 6.54 (1H, s), 7.07 (2H, d, J = 8.8 Hz), 7.71 (2H, d, J = 8.8 Hz), 8.07 (1H, d, J = 5.6 Hz), 10.92 (1H, s). $^{13}$C NMR (100 MHz, DMSO-d6): δ 31.60, 32.36, 39.14, 43.92, 52.20, 58.12, 83.67, 95.97, 114.46, 121.41, 127.64, 157.26, 157.50, 160.57, 161.03, 161.97, 162.73. |
| 47 | $^1$H NMR (400 MHz, DMSO-d6): δ 2.44 (2H, t, J = 5.8 Hz), 2.50-2.52 (4H, m), 3.55 (2H, q, J = 5.8 Hz), 3.82 (3H, s), 6.22 (1H, d, J = 5.6 Hz), 6.56 (1H, s), 7.08 (2H, d, J = 9.2 Hz), 7.75 (2H, d, J = 9.2 Hz), 8.10 (1H, d, J = 5.6 Hz), 10.97 (1H, s). $^{13}$C NMR (100 MHz, DMSO-d6): δ 43.62, 48.52, 52.95, 55.20, 58.48, 60.26, 83.85, 96.52, 114.43, 121.39, 127.75, 157.28, 157.43, 160.56, 161.18, 162.04, 162.69. |
| 48 | $^1$H NMR (400 MHz, DMSO-d6): δ 2.21 (3H, s), 2.38 (4H, bs), 3.74 (4H, bs), 3.81 (3H, s), 6.21 (1H, d, J = 5.4 Hz), 6.54 (1H, s), 7.06 (2H, d, J = 8.6 Hz), 7.73 (2H, d, J = 8.6 Hz), 8.09 (1H, d, J = 5.4 Hz), 10.95 (1H, s). $^{13}$C NMR (100 MHz, DMSO-d6): δ 43.54, 45.81, 54.39, 55.24, 83.91, 96.59, 114.45, 121.44, 127.79, 157.33, 157.49, 160.59, 161.25, 162.08, 162.68. |
| 49 | $^1$H NMR (400 MHz, DMSO-d6): δ 2.69 (4H, bs), 3.60 (4H, bs), 3.78 (3H, s), 5.32 (1H, s), 7.00 (2H, d, J = 8.8 Hz), 7.29 (1H, d, J = 5.6 Hz), 7.54 (2H, d, J = 8.8 Hz), 8.08 (1H, d, J = 5.6 Hz), 9.62 (1H, s). $^{13}$C NMR (100 MHz, DMSO-d6): δ 44.32, 45.35, 55.24, 84.41, 98.08, 113.87, 127.56, 128.79, 157.96, 158.76, 169.47, 160.74, 160.95, 169.06. |
| 50 | $^1$H NMR (400 MHz, DMSO-d6): δ 1.16 (3H, t, J = 7.2 Hz), 1.47-1.56 (2H, m), 1.89-1.92 (2H, m), 2.60-2.66 (1H, m), 3.05-3.10 (2H, m), 3.80 (3H, s), 4.05 (2H, q, J = 7.2 Hz), 4.49-4.52 (2H, m), 6.19 (1H, d, J = 5.4 Hz), 6.52 (1H, s), 7.05 (2H, d, J = 8.8 Hz), 7.71 (2H, d, J = 8.8 Hz), 8.08 (2H, d, J = 5.4 Hz), 10.95 (1H, s). $^{13}$C NMR (100 MHz, DMSO-d6): δ 14.01, 27.37, 40.38, 42.95, 55.19, 59.84, 83.75, 96.40, 114.43, 121.38, 127.69, 157.32, 157.52, 160.57, 161.04, 162.01, 162.65, 174.04. |
| 51 | $^1$H NMR (400 MHz, DMSO-d6): δ 1.50-1.58 (2H, m), 1.90-1.93 (2H, m), 2.58 (1H, m), 3.10-3.15 (2H, m), 3.80 (3H, s), 4.48-4.52 (2H, m), 6.21 (1H, d, J = 5.4 Hz), 6.55 (1H, s), 7.08 (2H, d, J = 8.4 Hz), 7.73 (2H, d, J = 8.4 Hz), 8.10 (1H, d, J = 5.4 Hz), 10.92 (1H, s). $^{13}$C NMR (100 MHz, DMSO-d6): δ 27.53, 40.53, 43.12, 55.20, 83.73, 96.31, 114.46, 121.39, 127.66, 157.31, 157.52, 160.58, 161.05, 162.00, 162.69, 175.90. |
| 52 | $^1$H NMR (400 MHz, DMSO-d6): δ 2.98-3.10 (4H, m), 3.65-3.68 (4H, m), 3.81 (3H, s), 5.68 (1H, d, J = 5.4 Hz), 6.77 (1H, s), 7.03 (2H, d, J = 8.4 Hz), 7.55 (2H, d, J = 8.4 Hz), 7.80 (1H, d, J = 5.4 Hz), 10.92 (1H, s). $^{13}$C NMR (100 MHz, DMSO-d6): δ 55.80, 58.42, 64.95, 100.08, 100.50, 114.45, 121.00, 128.50, 157.80, 158.52, 160.60, 160.65, 162.50, 165.10. |
| 53 | $^1$H NMR (400 MHz, DMSO-d6): δ 1.53-1.59 (6H, m), 2.95-2.98 (4H, m), 3.80 (3H, s), 5.70 (1H, d, J = 5.6 Hz), 6.57 (1H, s), 7.03 (2H, d, J = 8.8 Hz), 7.56 (2H, d, J = 8.8 Hz), 7.80 (1H, d, J = 5.6 Hz), 10.95 (1H, s). $^{13}$C NMR (100 MHz, DMSO-d6): δ 24.23, 25.60, 55.82, 59.75, 99.98, 101.50, 114.48, 121.21, 128.47, 157.88, 158.23, 160.61, 160.60, 162.34, 165.12. |
| 54 | $^1$H NMR (400 MHz, DMSO-d6): δ 1.67-1.92 (4H, m), 2.73-2.74 (1H, m), 3.57-3.67 (4H, m), 3.80 (3H, s), 5.68 (1H, d, J = 5.4 Hz), 6.52 (1H, s), 7.05 (2H, d, J = 8.8 Hz), 7.54 (2H, d, J = 8.8 Hz), 7.88 (1H, d, J = 5.4 Hz), 10.55 (1H, s). $^1$H NMR (400 MHz, DMSO-d6): δ 36.28, 55.10, 55.82, 65.70, 100.98, 101.47, 114.36, 121.30, 128.45, 157.88, 158.24, 160.59, 160.65, 162.33, 165.09. |

TABLE 2-continued

| Compd No | $^1H$ NMR/$^{13}C$ NMR |
|---|---|
| 59 | $^1H$ NMR (400 MHz, DMSO-d6): δ 1.69-1.74 (2H, m), 1.86-1.96 (2H, m), 3.68-3.73 (2H, m), 3.80 (3H, s), 3.84-3.89 (2H, m), 4.83-4.97 (1H, m), 6.64 (1H, s), 7.05 (2H, d, J = 8.6 Hz), 7.71 (2H, d, J = 8.6 Hz), 8.18 (1H, s), 10.50 (1H, s). $^{13}C$ NMR (100 MHz, DMSO-d6): δ 30.47 (d, $^2J_{C-F}$ = 19.1 Hz), 40.34 (d, $^3J_{C-F}$ = 6.1 Hz), 55.20, 86.75, 88.52 (d, $^1J_{C-F}$ = 168.4 Hz), 102.52, 114.47, 121.22, 127.68, 153.10, 156.01, 159.02, 160.62, 161.91, 162.22. |
| 60 | $^1H$ NMR (400 MHz, DMSO-d6): δ 1.68-1.74 (2H, m), 1.86-1.97 (2H, m), 3.64-3.70 (2H, m), 3.79 (3H, s), 3.84-3.89 (2H, m), 4.82-4.96 (1H, m), 6.60 (1H, s), 7.05 (2H, d, J = 8.6 Hz), 7.71 (2H, d, J = 8.6 Hz), 8.17 (1H, d, J = 3.2 Hz), 11.18 (1H, s). $^{13}C$ NMR (100 MHz, DMSO-d6): δ 30.47 (d, $^2J_{C-F}$ = 19.0 Hz), 40.69 (d, $^3J_{C-F}$ = 6.8 Hz), 55.19, 85.34, 88.66 (d, $^1J_{C-F}$ = 168.4 Hz), 114.46, 121.23, 127.70, 139.39 (d, $^1J_{C-F}$ = 245.3 Hz), 142.68 (d, $^2J_{C-F}$ = 19.1 Hz), 146.26 (d, $^3J_{C-F}$ = 11.4 Hz), 157.18, 160.62, 161.96, 162.01. |
| 61 | $^1H$ NMR (400 MHz, DMSO-d6): δ 1.68-1.73 (2H, m), 1.86-1.97 (2H, m), 2.19 (3H, s), 3.69-3.75 (2H, m), 3.80 (3H, s), 3.91-3.96 (2H, m), 4.83-4.96 (1H, m), 6.07 (1H, s), 6.50 (1H, s), 7.04 (2H, d, J = 9.0 Hz), 7.71 (2H, d, J = 9.0 Hz), 10.85 (1H, s). $^{13}C$ NMR (100 MHz, DMSO-d6): δ 23.92, 30.68 (d, $^2J_{C-F}$ = 18.3 Hz), 40.00 (d, $^3J_{C-F}$ = 6.1 Hz), 55.18, 83.57, 88.86 (d, $^1J_{C-F}$ = 168.4 Hz), 94.96, 114.41, 121.44, 127.69, 157.77, 160.55, 160.87, 162.1, 162.90, 166.76. |
| 62 | $^1H$ NMR (400 MHz, DMSO-d6): δ 3.69-3.70 (8H, m), 3.81 (3H, s), 5.84 (1H, s), 5.91 (1H, d, J = 5.6 Hz) 6.77 (1H, s), 7.04 (2H, d, J = 9.0 Hz), 7.55 (2H, d, J = 9.0 Hz), 7.65 (1H, d, J = 5.6 Hz), 10.98 (1H, s). $^{13}C$ NMR (100 MHz, DMSO-d6): 48.70, 55.80, 66.32, 95.13, 100.00, 100.51, 114.80, 120.54, 128.50, 149.06, 155.13, 157.65, 158.90, 160.66, 162.00. |
| 63 | $^1H$ NMR (400 MHz, DMSO-d6): δ 3.47 (3H, s), 3.64-3.67 (8H, m), 3.80 (3H, s), 6.51 (1H, d, J = 6.0 Hz), 6.71 (1H, s), 7.04 (2H, d, J = 8.8 Hz), 7.77 (2H, d, J = 8.8 Hz), 8.17 (1H, d, J = 6.0 Hz). $^{13}C$ NMR (100 MHz, DMSO-d6): δ 34.63, 43.91, 55.22, 65.89, 88.32, 96.26, 114.38, 121.10, 127.80, 158.18, 159.50, 160.68, 160.84, 162.37, 165.38. |
| 64 | $^1H$ NMR (400 MHz, DMSO-d6): δ 1.72-1.77 (2H, m), 1.90-2.01 (2H, m), 2.97 (6H, s), 3.73-3.79 (2H, m), 3.94-3.99 (2H, m), 4.87-5.01 (1H, m), 6.23 (1H, d, J = 5.4 Hz), 6.51 (1H, s), 6.81 (2H, d, J = 9.0 Hz), 7.61 (2H, d, J = 9.0 Hz), 8.11 (1H, d, J = 5.4 Hz), 10.93 (1H, s). $^{13}C$ NMR (100 MHz, DMSO-d6): δ 30.71 (d, $^2J_{C-F}$ = 19.0 Hz), 39.70, 40.01, 83.53, 88.79 (d, $^1J_{C-F}$ = 168.0 Hz), 96.50, 111.96, 116.07, 127.10, 151.25, 157.42, 157.49, 160.95, 162.21, 162.37. |
| 65 | $^1H$ NMR (400 MHz, DMSO-d6): δ 1.71-1.75 (2H, m), 1.88-1.99 (2H, m), 3.71-3.77 (2H, m), 3.90 (3H, s), 3.93-3.97 (2H, m), 4.85-5.00 (1H, m), 6.23 (1H, d, J = 5.4 Hz), 6.57 (1H, s), 7.29-7.33 (1H, m), 7.58-7.64 (2H, m), 8.11 (1H, d, J = 5.4 Hz), 11.01 (1H, s). $^{13}C$ NMR (100 MHz, DMSO-d6): δ 30.47 (d, $^2J_{C-F}$ = 19.1 Hz), 40.07, 56.09, 84.00, 88.84 (d, $^1J_{C-F}$ = 168.4 Hz), 96.53, 113.58 (d, $^2J_{C-F}$ = 19.8 Hz), 114.23, 121.80 (d, $^3J_{C-F}$ = 7.6 Hz), 123.23 (d, $^4J_{C-F}$ = 3.9 Hz), 148.58 (d, $^3J_{C-F}$ = 9.9 Hz), 151.47 (d, $^1J_{C-F}$ = 243.1 Hz), 157.43, 157.68, 161.00, 161.36, 162.97. |
| 66 | $^1H$ NMR (400 MHz, DMSO-d6): δ 1.99 (4H, m), 3.59-3.68 (4H, m), 3.91 (3H, s), 4.60 (2H, m), 6.27 (1H, d, J = 5.6 Hz), 6.55 (1H, s), 7.29-7.33 (1H, m), 7.59-7.66 (2H, m), 8.13 (1H, d, J = 5.6 Hz), 11.05 (1H, s). $^{13}C$ NMR (100 MHz, DMSO-d6): δ 26.62, 55.04, 56.09, 70.33, 84.03, 97.10, 113.63 (d, $^2J_{C-F}$ = 19.8 Hz), 114.22, 121.80 (d, $^3J_{C-F}$ = 6.9 Hz), 123.31, 148.57 (d, $^3J_{C-F}$ = 10.7 Hz), 151.45 (d, $^1J_{C-F}$ = 243.1 Hz), 157.57, 157.84, 160.05, 161.39, 162.89. |
| 67 | $^1H$ NMR (400 MHz, DMSO-d6): δ 1.92-1.96 (4H, m), 3.48-3.55 (4H, m), 3.88 (3H, s), 6.12 (1H, d, J = 5.8 Hz), 6.68 (1H, s), 7.25-7.29 (1H, m), 7.54-7.59 (2H, m), 8.03 (1H, d, J = 5.8 Hz), 10.93 (1H, s). $^{13}C$ NMR (100 MHz, DMSO-d6): δ 25.50, 46.68, 56.54, 84.52, 96.07, 113.99 (d, $^2J_{C-F}$ = 19.0 Hz), 114.68 (d, $^4J_{C-F}$ = 2.0 Hz), 122.43 (d, $^3J_{C-F}$ = 7.0 Hz), 123.65 (d, $^4J_{C-F}$ = 3.0 Hz), 148.99 (d, $^3J_{C-F}$ = 11.0 Hz), 151.94 (d, $^1J_{C-F}$ = 243.0 Hz), 157.43, 157.88, 160.26, 161.81 (d, $^4J_{C-F}$ = 2.0 Hz), 163.53. |

Example 2: Exemplary Biological Results

The ability of the compounds of the present disclosure to treat TACC3-mediated cancers, or associated symptoms or complications thereof, was determined using the following procedures. The compounds of the present disclosure were tested for their activity against cell death induction using a JIMT-1 cell line, which was a cell line having high level of TACC3. The concentration of each compound that was required for half-maximal inhibition of cell proliferation was calculated by a GraphPad Prism (GraphPad Software). Table 3 below demonstrates compounds in order of the strength of inhibitory effect on cell growth. The compounds 5, 9, 13, 14, 20-24, 26, 33, 34, 37-40, 42-45, 59, 60 and 63-67 of the present disclosure were determined to have remarkable inhibitory effects on cell growth.

TABLE 3

$IC_{50}$ values of the compounds of the present disclosure against JIMT-1 cells.

| Compound Code | $IC_{50}$ (μM) |
|---|---|
| Compound 5 | 0.120 |
| Compound 6 | 3.440 |
| Compound 7 | 8.270 |
| Compound 8 | >10 |
| Compound 9 | 0.810 |
| Compound 10 | >10 |
| Compound 11 | >10 |
| Compound 12 | >10 |
| Compound 13 | 0.640 |
| Compound 14 | 0.259 |
| Compound 15 | 3.610 |

TABLE 3-continued

IC$_{50}$ values of the compounds of the present disclosure against JIMT-1 cells.

| Compound Code | IC$_{50}$ (μM) |
|---|---|
| Compound 16 | >10 |
| Compound 17 | >10 |
| Compound 18 | 4.230 |
| Compound 19 | >10 |
| Compound 20 | 0.030 |
| Compound 21 | 0.120 |
| Compound 22 | 0.013 |
| Compound 23 | 0.480 |
| Compound 24 | 0.730 |
| Compound 26 | 0.870 |
| Compound 27 | 7.30 |
| Compound 30 | >10 |
| Compound 32 | >10 |
| Compound 33 | 0.230 |
| Compound 34 | 0.160 |
| Compound 35 | 3.090 |
| Compound 36 | 2.020 |
| Compound 37 | 0.480 |
| Compound 38 | 0.130 |
| Compound 39 | 0.370 |
| Compound 40 | 0.113 |
| Compound 41 | >10 |
| Compound 42 | 0.116 |
| Compound 43 | 0.204 |
| Compound 44 | 0.056 |
| Compound 45 | 0.105 |
| Compound 46 | 3.970 |
| Compound 47 | >10 |
| Compound 48 | 1.560 |
| Compound 49 | >10 |
| Compound 50 | >10 |
| Compound 51 | >10 |
| Compound 59 | 0.800 |
| Compound 60 | 0.540 |
| Compound 61 | 1.000 |
| Compound 63 | 0.160 |
| Compound 64 | 0.157 |
| Compound 65 | 0.145 |
| Compound 66 | 0.053 |
| Compound 67 | 0.049 |

Since these compounds of the present disclosure exhibited a cell growth inhibitory effect, they can be expected to inhibit the growth of tumors when they used as anticancer agents in pharmaceutical compositions. Thus, the present inventors selected compound 5 for further detailed analysis of its activity on cell growth, particularly its effect on TACC3 and cell division, and also its in vivo inhibitory effect on tumor growth in related animal models.

Figure 4A:
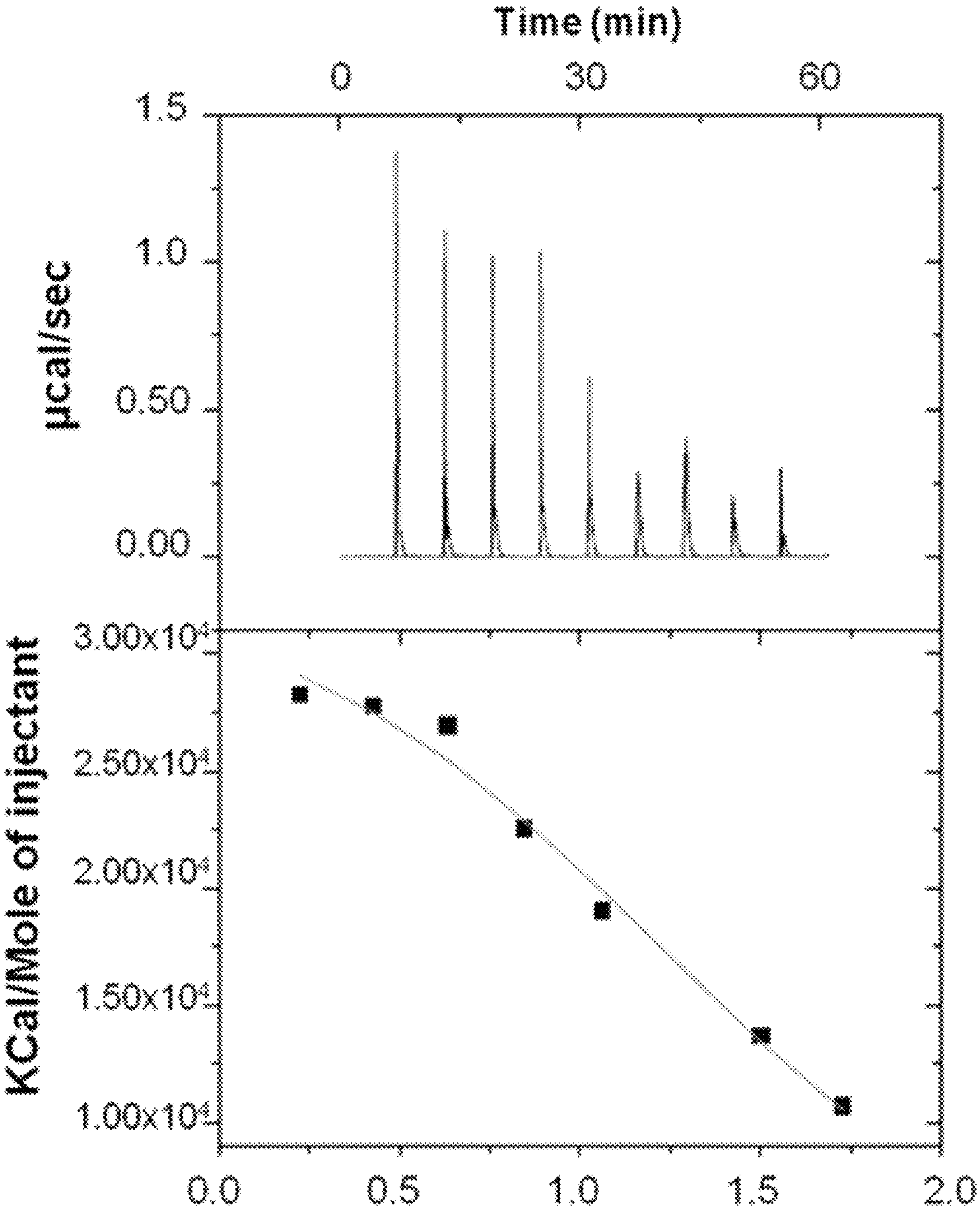
FIG. 4A is a graph showing the determination of the association constant for the TACC3 and compound 5 interaction using isothermal titration calorimetry (ITC). Upper trace shows raw data while lower trace shows integrated data from a titration of TACC3 into compound 5. Model fitting of a single interaction model was applied using the Origin 7 software provided along with the ITC200 instrument.
Figure 4B:
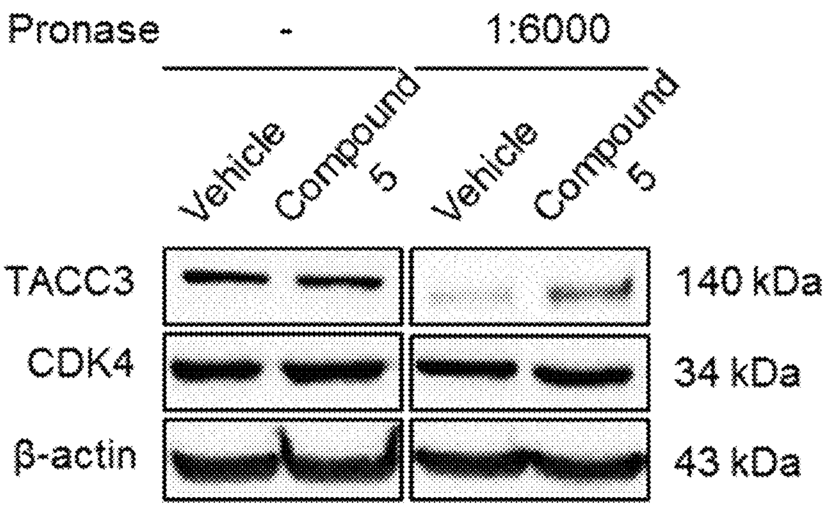
FIG. 4B shows western blot results of DARTS assay using JIMT-1 cell protein extracts to confirm the interaction between compound 5 and TACC3. CDK4 was used as a non-target protein whose level unchanged between treatment groups. 10 M of drugs were used. SPL-B was used as positive control for binding.
Figure 4C:
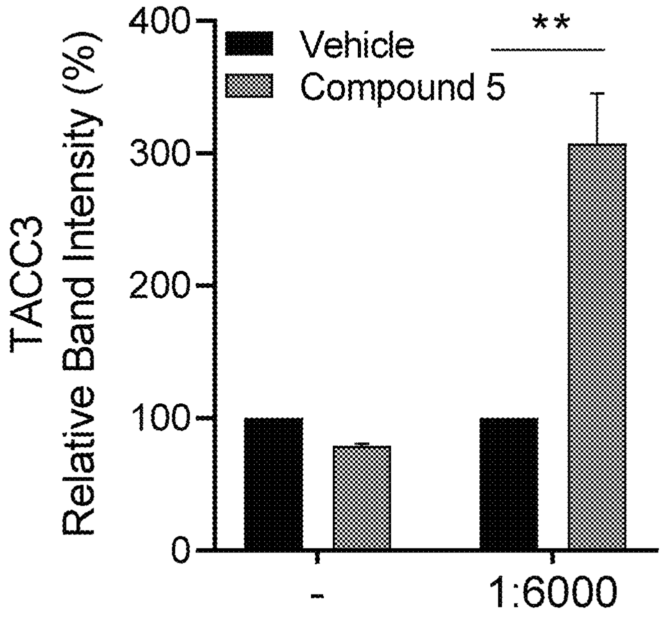
FIG. 4C is a graph showing the quantification of the TACC3 relative band intensity between the treatment groups normalized to β-actin and are representative of at two independent experiments. Data is presented as means±SD. **p<0.01
Figure 6A:
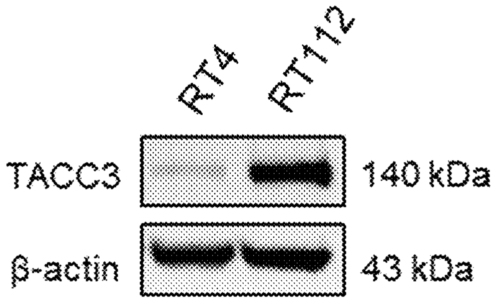
FIG. 6A shows western blot analysis of TACC3 protein levels in RT112 and RT4 cells. 3-actin was used as loading control.
Figure 6B:
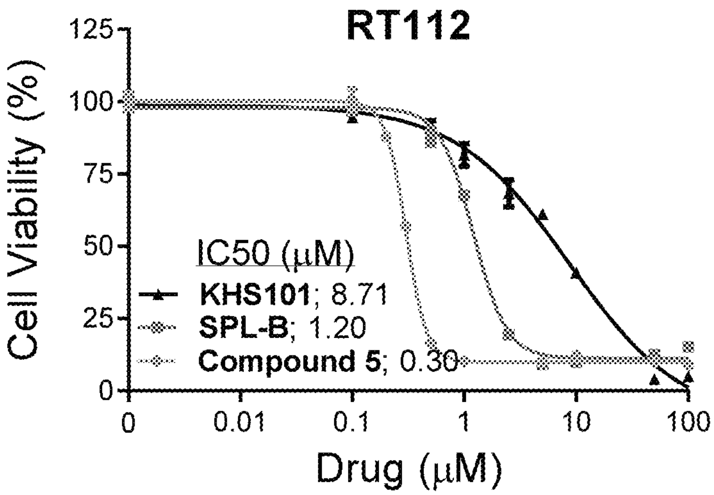
FIG. 6B are graphs showing the pharmacological inhibition of TACC3 with three different inhibitors and their effect on cell viability of FGFR3-TACC3 fusion expressing cell lines, RT112 and RT4. Cell viability was tested upon 3 days of drug incubation and measured by SRB assay.
Figure 6B:
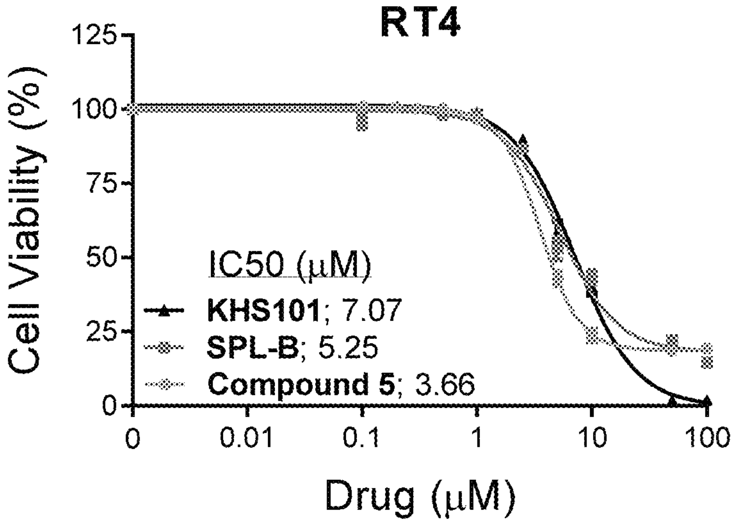
Figure 6C:
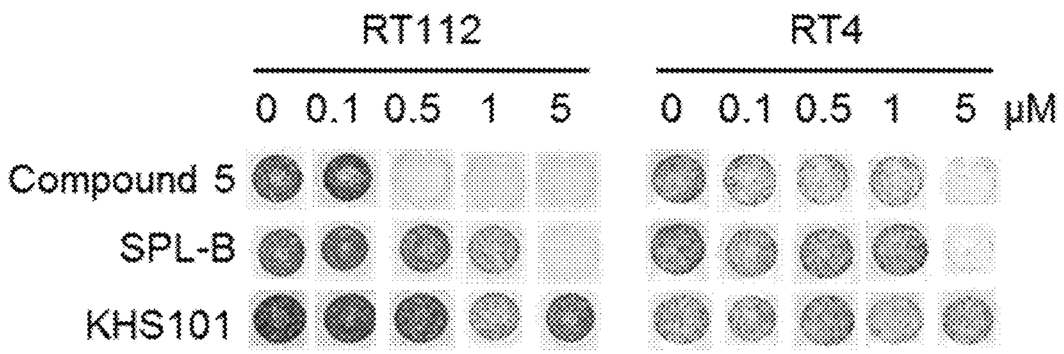
FIG. 6C are images showing SRB stained representative wells after treatment with three inhibitors.

Studies were performed to determine whether compound 5 binds to TACC3. A titration of TACC3 into compound 5 was carried out and monitored by recording the calorimetric and heat changes. As shown in FIG. 4A, thermodynamics parameters of compound 5 binding to TACC3 at 25° C. ($K_d$: 1.5 nM; ΔH: 4.929E7 cal/mol; ΔS: 1.65E5 cal/mol/deg, N: 0.704) demonstrate the interaction between these two molecules. Binding of compound 5 to TACC3 was lastly confirmed with drug affinity responsive target stability (DARTS method). DARTS is a label free-strategy to identify potential direct protein targets for small molecules and is based on stabilization and protection from proteolysis of the target protein upon binding to small molecules. As shown in FIG. 6C, TACC3 protein was stabilized upon incubation with compound 5 in the presence of the pronase (FIG. 4C).

Figure 5A:
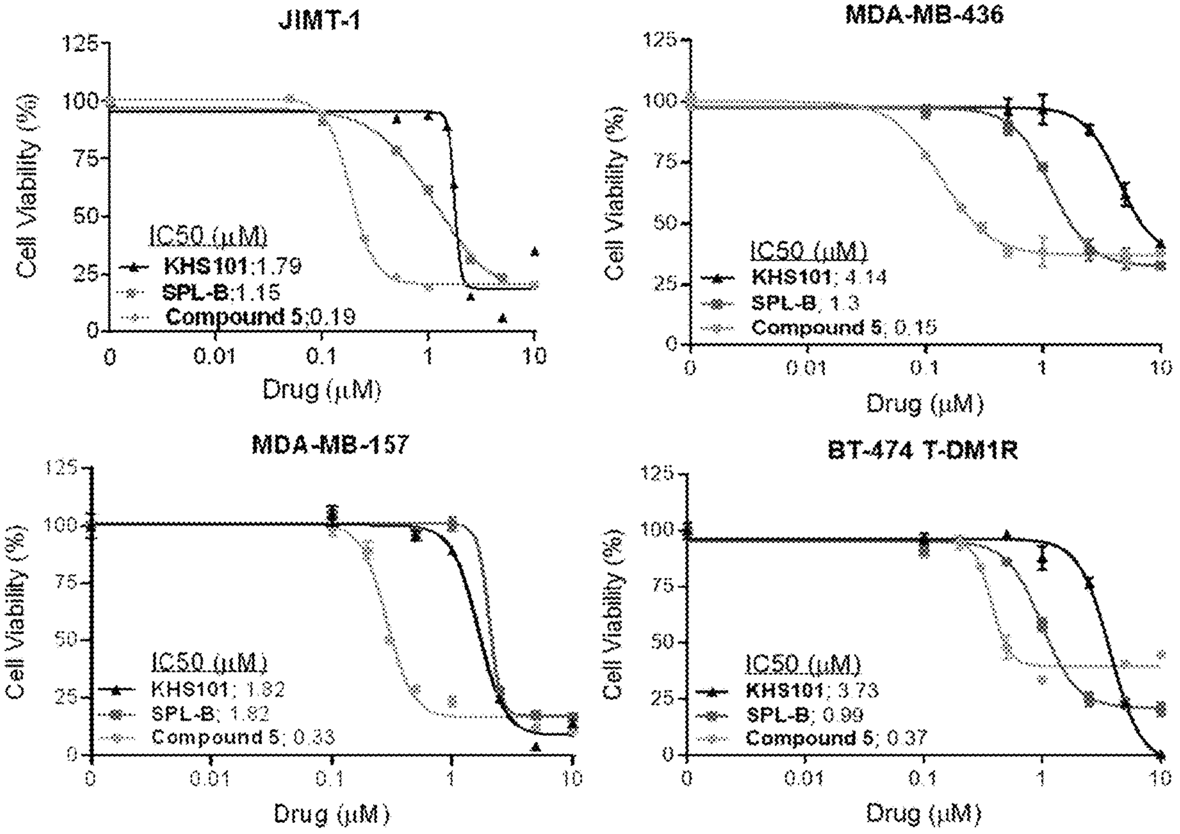
FIG. 5A are graphs showing the pharmacological inhibition of TACC3 with three different inhibitors and their effect on cell viability of breast cancer cell lines ($IC_{50}$: inhibitory concentration 50%). Cell viability was measured by Sulforhodamine B (SRB) assay as triplicates in all the following cell viability experiments.
Figure 5B:
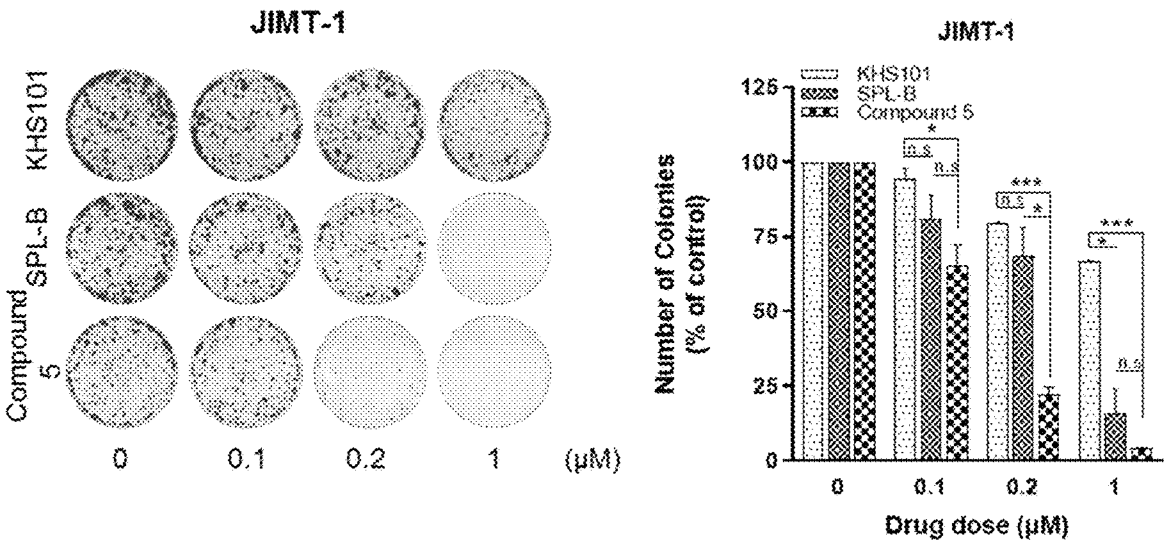
FIG. 5B shows that colony formation assay of JIMT-1 cells treated with three different TACC3 inhibitors for 12 days. Colonies were stained with crystal violet. Number of colonies was counted and analyzed using ImageJ software (lower panel). Data is presented as means±SD. *: p<0.05; : p<0.01; *: p<0.001.
Figure 5C:
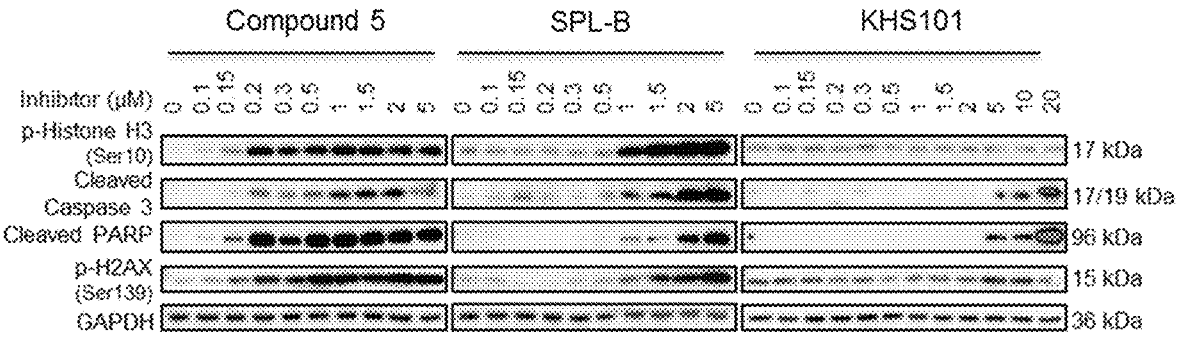
FIG. 5C shows western blot analysis of JIMT-1 cells treated with compound 5, SPL-B or KHS101 to test the effect of dose responses on mitotic arrest, DNA damage and apoptosis markers. The same amount of protein and the same exposure time were used in Western blot experiments to compare the effects of three drugs on these markers.
Figure 5D:
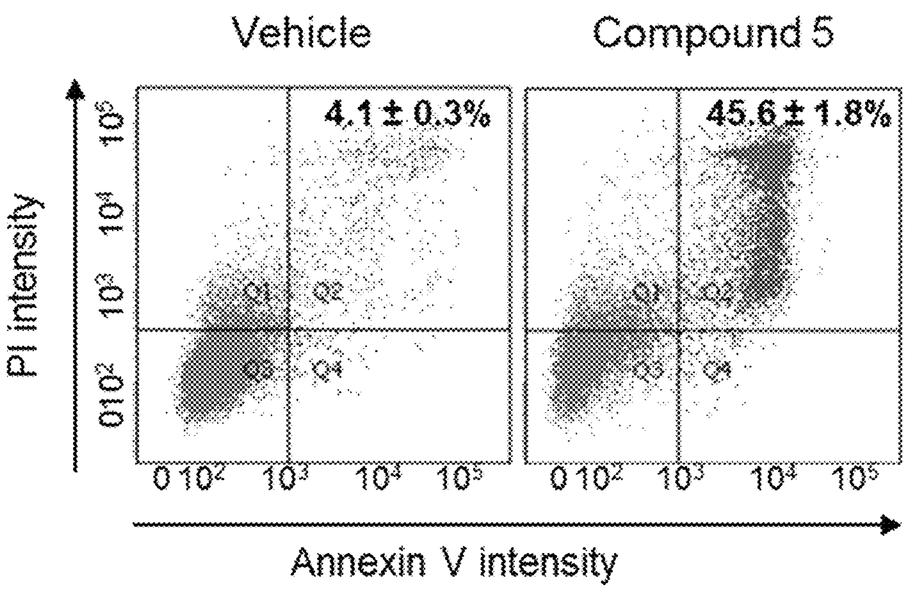
FIG. 5D is a plot showing Annexin V/PI staining of compound 5 (500 nM)-treated JIMT-1 cells. The percentage of Annexin V/PI double positive cells are provided on the graph.
Figure 7A:
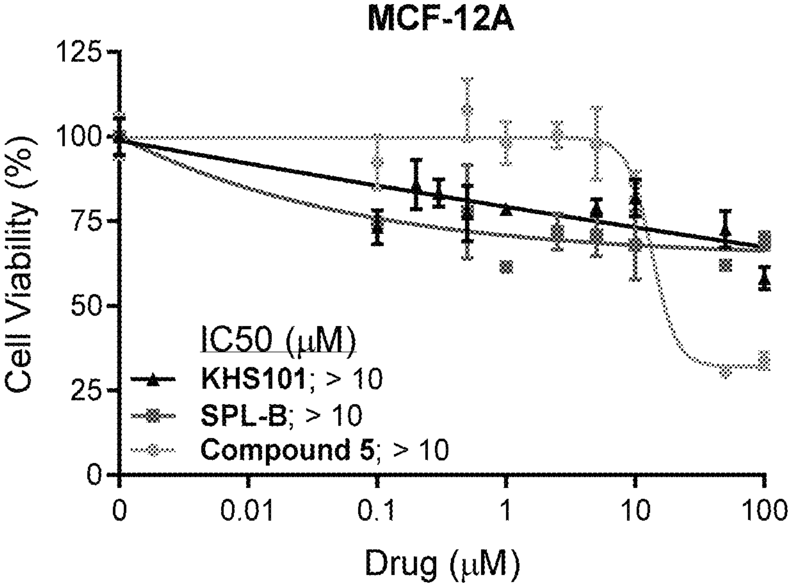
FIG. 7A shows the pharmacological inhibition of TACC3 with three different inhibitors and their effect on cell viability of normal breast cell line, MCF-12A.
Figure 7B:
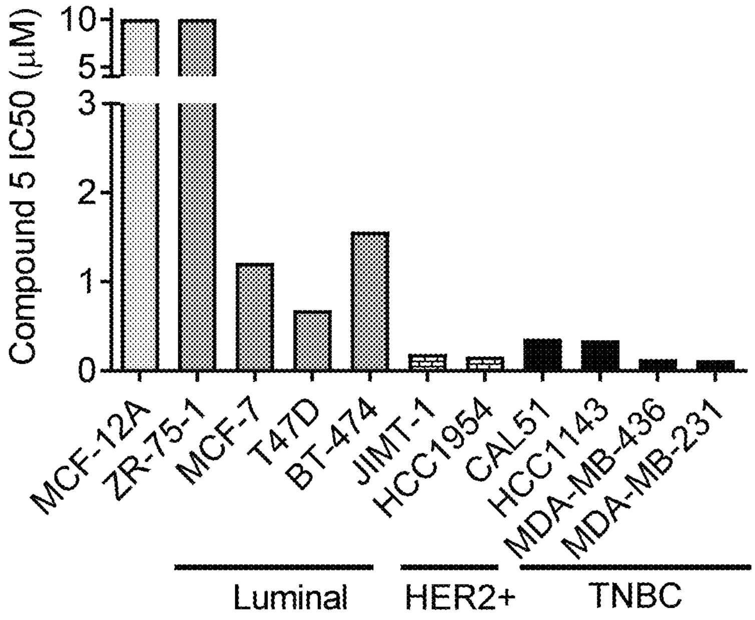
FIG. 7B shows that compound 5 $IC_{50}$ levels of breast normal epithelial cell line, MCF-12A and cancer cell lines separated according to their subtypes.
Figure 7C:
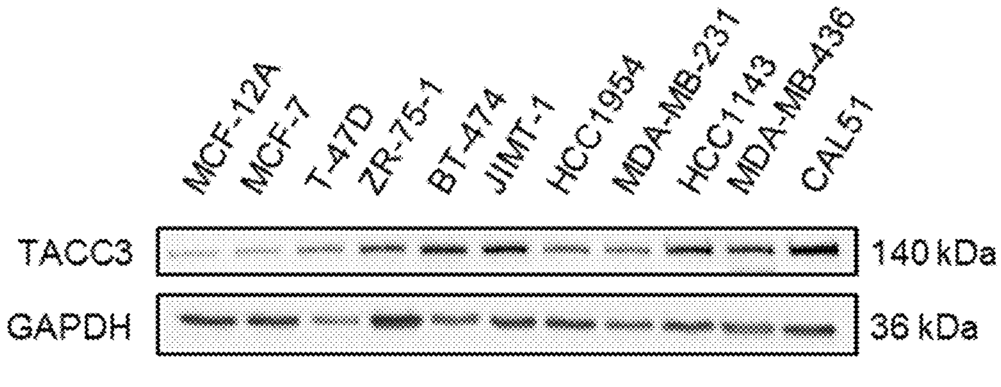
FIG. 7C shows TACC3 protein levels of these cell lines. TACC3 protein level was analyzed by Western blot. GAPDH was used as loading control.
Figure 7D:
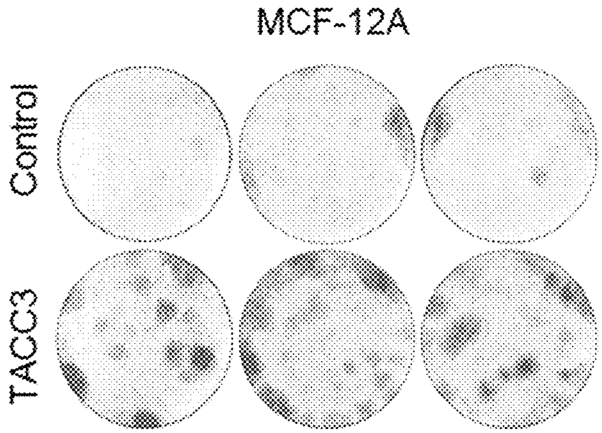
FIG. 7D shows a colony formation assay of MCF-12A cells. Cells were transiently transfected with either control or TACC3 vector (250 ng) for 48 h. Transfected cells were later seeded on 12-well plates. Cells were stained with crystal violet after 12 days.
Figure 7E:
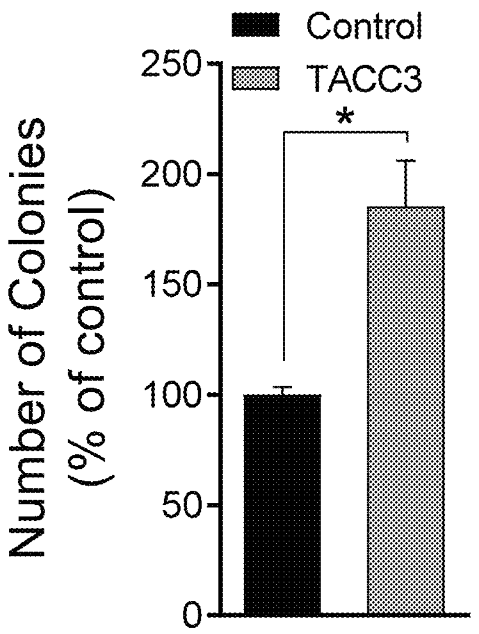
FIG. 7E shows that the number of colonies was counted and analyzed using ImageJ software. Data is presented as means±SD of three independent experiments. *: p<0.05; : p<0.01; *: p<0.001. n.s: not significant.

After that, the relative effects of TACC3 inhibitor, compound 5, with the available TACC3 inhibitors KHS101 and SPL-B on cell viability were compared. JIMT-1, MDA-MB-436, MDA-MB-157 and BT-474 T-DM1R cell lines were tested with respect to their response to these three drugs. Compound 5 was found to have a significantly lower IC$_{50}$ values than the two available TACC3 inhibitors in all cell lines tested (FIG. 5A). This marked decrease in cell viability of different cancer cell lines treated with compound 5 compared to KHS101 and SPL-B was also validated with colony formation assay using JIMT-1 cells. As a result, the average colony number of JIMT-1 cells treated with compound 5 was significantly lower than the ones treated with other two inhibitors at the same doses (FIG. 5B). Therefore, the low cell viability detected with SRB assay and low number of colonies of JIMT-1 cells indicate that compound 5 is more effective and more potent than the other two TACC3 inhibitors, KHS101 and SPL-B in vitro. Induction of mitotic arrest, apoptosis and DNA damage processes as in case of siTACC3 treatment in breast cancer cell lines were further tested upon compound 5, SPL-B and KHS101 treatments. It was demonstrated that the results of analysis using compound 5 is very consistent with the results of the experiments on the suppression of TACC3 expression using siRNA, further suggesting that compound 5 targets TACC3. As a result, siTACC3-induced mitotic arrest, DNA damage and apoptosis can be recapitulated by compound 5 in a dose-dependent manner (FIG. 5C). On the other hand, similar induction levels of these markers by SPL-B and KHS101 treatment were observed at considerably higher doses as compared to compound 5 treated cells. Although higher KHS101 doses was included, which were used by others, an induction of these markers was only observed at very high doses. Clearly, these results are consistent with the cell viability data and the IC$_{50}$ values obtained through the treatment with three inhibitors (see FIG. 5A). Furthermore, treatment of JIMT-1 cells with compound 5 for 72 h induced a prominent increase (from 4.1% to 45.6%) in the fraction of apoptotic cells as assessed by Annexin V/PI staining (FIG. 7D). These results further validate the 1) high potency of compound 5 with respect to nM range working doses, and 2) specificity with respect to the similar molecular alterations obtained by TACC3 downregulation using siRNAs.

Figure 5E:
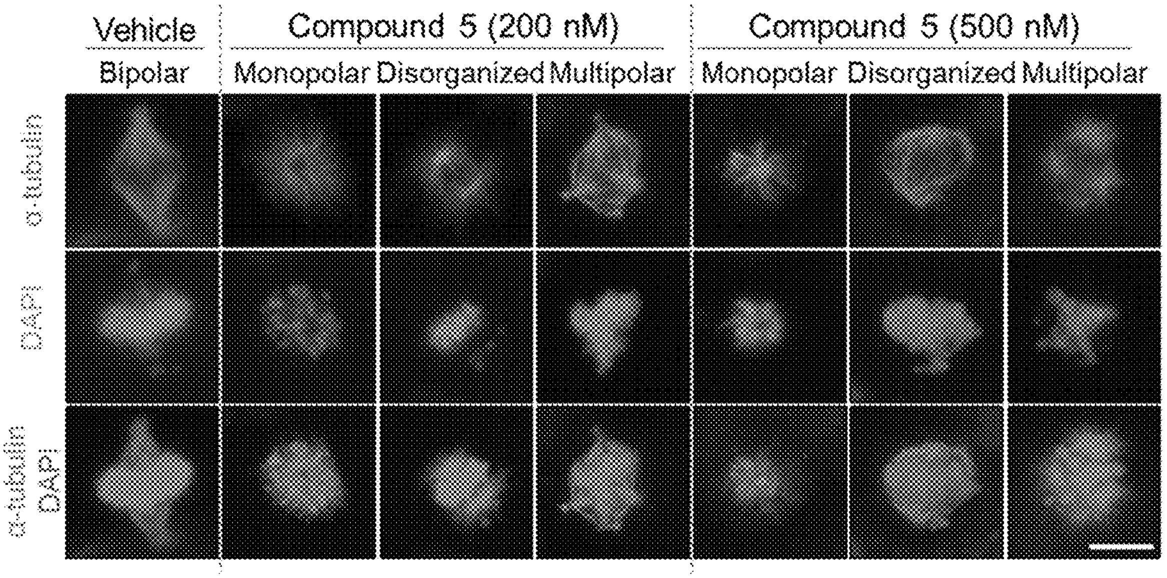
FIG. 5E show that induction of aberrant spindle formations in compound 5 treated JIMT-1 cells. Cells were treated with two different doses of compound 5 for 12 h, fixed in methanol and then stained with anti-α-tubulin (green) antibody. DNA was stained with DAPI (blue). Scale bar: 10 m.
Figure 5F:
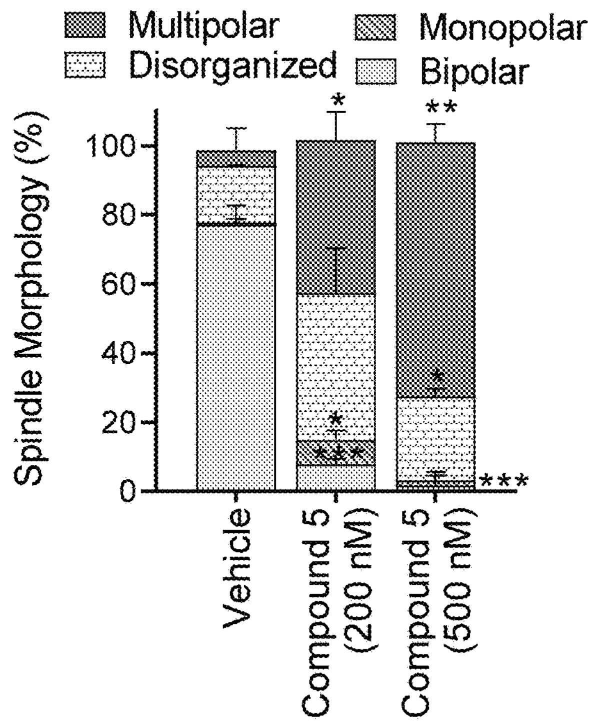
FIG. 5F is a graph showing the quantification of spindle abnormalities as seen in D. The data represent the mean values and the standard deviations (SDs) of three independent experiments (t-test) *: p<0.05; : p<0.01; *: p<0.001. Significance was determined by comparison with vehicle group.
Figure 5G:
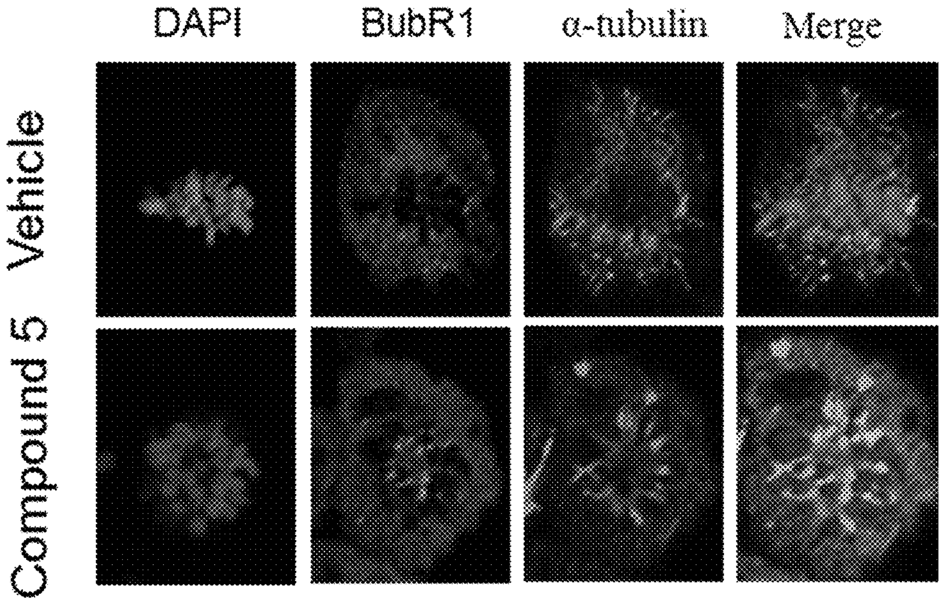
FIG. 5G shows immunofluorescence staining of SAC marker, BubR1 (red) and α-tubulin (green) in vehicle versus compound 5 (500 nM)-treated JIMT-1 cells.
Figure 5H:
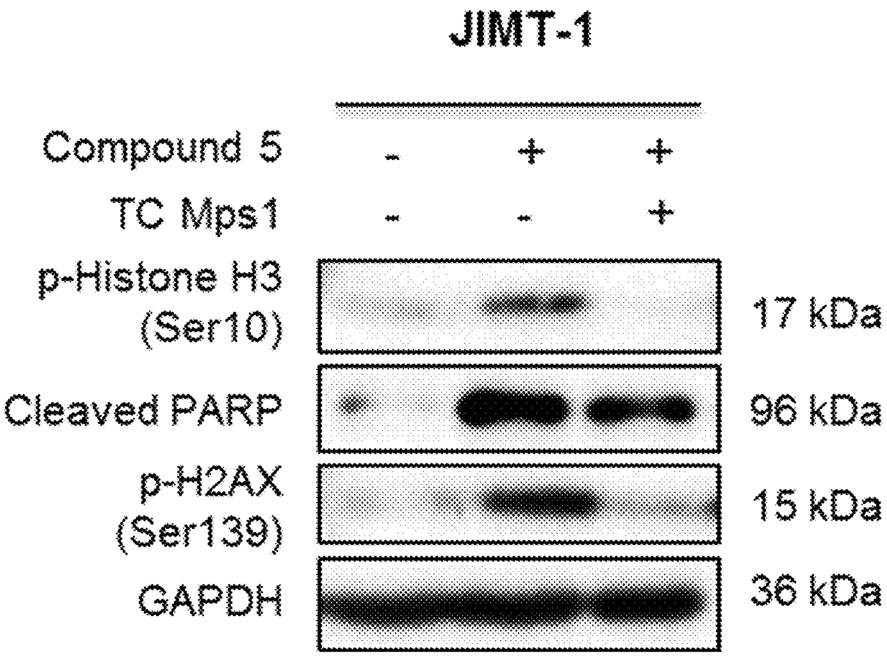
FIG. 5H shows western blot analysis of mitotic arrest, DNA damage and apoptosis markers showing mitotic slippage in compound 5 treated JIMT-1 cells upon treatment with a spindle checkpoint kinase (Mps1) inhibitor, TC Mps1. JIMT-1 cells were treated with 200 nM compound 5 for 24 h followed by 12 h treatment with 1 M TC Mps1. GAPDH was used as a loading control.

The present inventors then tested a potential disruption of mitotic spindles as a result of TACC3 inhibition, which was previously demonstrated to cause severe spindle defects (Schneider, Essmann et al. 2007). Inhibition of TACC3 with compound 5 has led to formation of aberrant spindle structures in a dose-dependent manner (FIG. 5E). The most prominent phenotype seen upon TACC3 inhibition by compound 5 was the formation of multipolar spindles characterized by improperly aligned chromosomes at the metaphase plate (73.4% frequency upon treatment with the highest dose) in JIMT-1 cells (FIG. 5F). The presence of spindle defects activates the spindle assembly checkpoint (SAC) that further leads to mitotic arrest to provide the necessary time for repairing the spindle defects (Musacchio and Salmon 2007). To demonstrate SAC activation upon TACC3 inhibition, we performed immunofluorescence staining of BuBR1, a marker of SAC activation (Chen 2002). In compound 5-treated JIMT-1 cells, we observed an increased localization of BuBR1 to chromosomes upon compound 5 treatment (FIG. 5G). To further test the contribution of an active SAC signaling to compound 5-induced mitotic arrest, DNA damage and cell death, we inhibited the SAC kinase, Mps1 using a specific inhibitor (TC Mps1 (Choi, Min et al. 2017)) in compound 5-treated cells, and analyzed the expression of relevant markers. As shown in FIG. 5H, inhibiting Mps1 kinase caused a prominent loss of mitotic arrest, apoptosis and DNA damage suggesting that compound 5 may function by activating SAC upon inducing severe spindle defects that further leads to prolonged mitosis, apoptotic cell death and DNA damage.

Figure 6D:
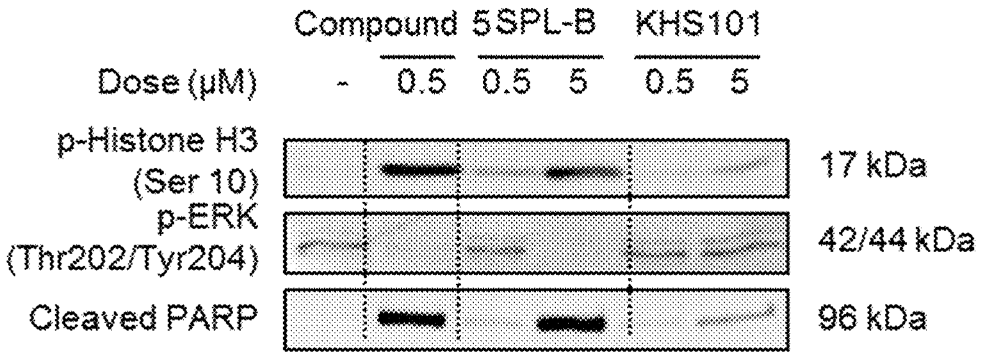
FIG. 6D shows western blot analysis of mitotic arrest marker, p-Histone H3 as well as the ERK phosphorylation (Thr202/Tyr204) in RT112 cells upon treatment with TACC3 inhibitors at different doses for 24 h.

FGFR3-TACC3 oncogenic fusion proteins are detected in numerous solid tumors and are emerging as attractive therapeutic targets that will enable selective targeting of fusion-harboring cancers (Costa, Carneiro et al. 2016). To test whether compound 5 treatment is able to inhibit the growth of fusion-carrying cell lines, we utilized two human urinary bladder cancer cell lines, RT112 and RT4 that are known to harbor FGFR3-TACC3 fusion protein (Williams, Hurst et al. 2013). Western blot analysis of TACC3 revealed a higher expression in RT112 cells (FIG. 6A) that was further accompanied by a stronger response to compound 5 as demonstrated by a lower IC50 in RT112 cells (FIGS. 6B and C). Despite a relatively lower sensitivity to TACC3 inhibition in RT4 cells (potentially due to lower TACC3 levels), compound 5 yielded the lowest IC50 value in both models as compared to SPL-B and KHS101, suggesting that compound 5 might be a highly relevant therapeutic opportunity to target FGFR3-TACC3 fusion-harboring tumors (FIG. 6B). Moreover, compound 5 decreased ERK1/2 phosphorylation, which is a marker for activated FGFR signaling along with a strong mitotic arrest (FIG. 6D) at minimum 10× lower doses than other TACC3 inhibitors, suggesting that compound 5 specifically blocks the function of FGFR3-TACC3 fusion protein.

Figure 6E:
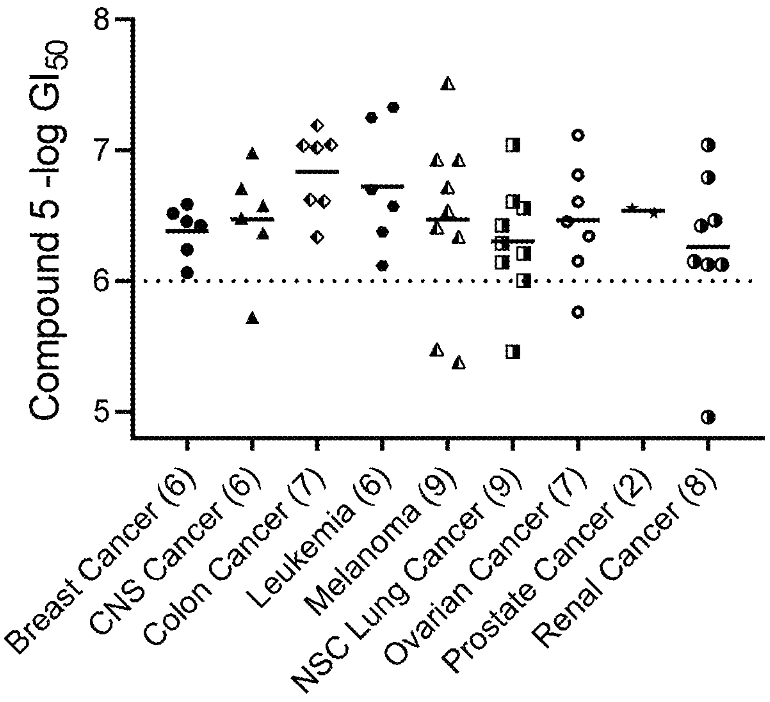
FIG. 6E is a graph showing average $GI_{50}$ values (M) determined from the NCI-60 five-dose screen for compound 5. Black dotted line indicates 1 M threshold.
Figure 6F:
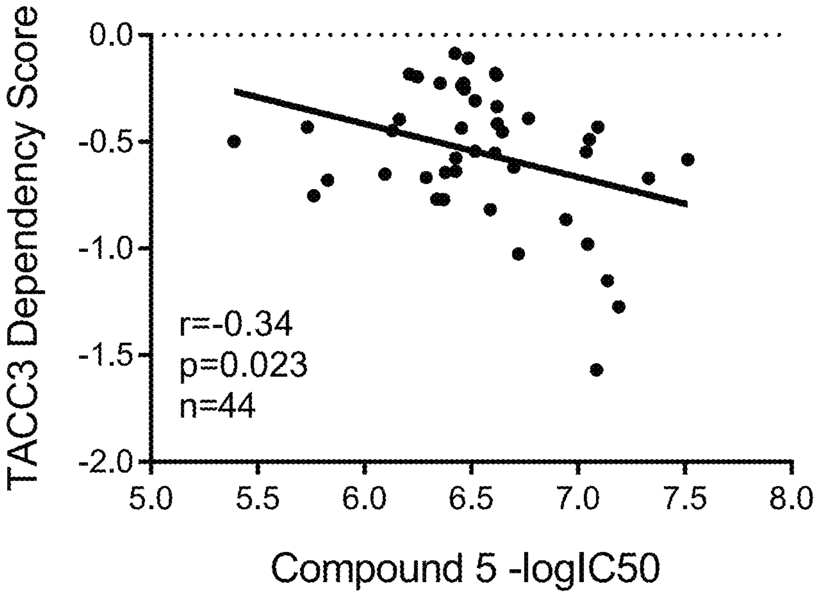
FIG. 6F is a graph showing the correlation between $GI_{50}$ values of compound 5 and TACC3 dependency score obtained from DepMap.org. A lower score means that TACC3 is more likely to be dependent in a given cell line.

Following these promising results in breast cancer cell lines, compound 5 was also tested in other cancer types. Therefore, compound 5 was screened for the anti-proliferative activity on NCI-60 human cell lines. Analysis of the five-dose screen reveals that almost all cell lines were found to be sensitive to compound 5 treatment with less than 1 M 50% growth inhibition ($GI_{50}$) value suggesting its possible applications in other cancer types (FIG. 6E). Notably, we found that GI50 values of NCI-60 cell lines show a positive correlation with the TACC3 dependency score obtained from DepMap.org (McFarland, Ho et al. 2018) (FIG. 6F). This indicates that cells which are more dependent on TACC3, i.e. having low TACC3 dependency score, are more sensitive to compound 5. Collectively, these data demonstrate the strong anti-cancer activity of compound 5, highlighting its potential applications also in various cancer types.

Figure 7F:
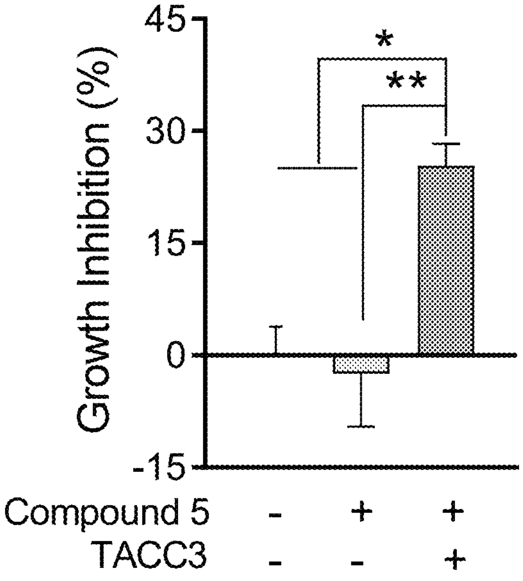
FIG. 7F is a graph showing the cell viability assay upon compound 5 treatment of TACC3 overexpressing MCF-12A cells.
Figure 7G:
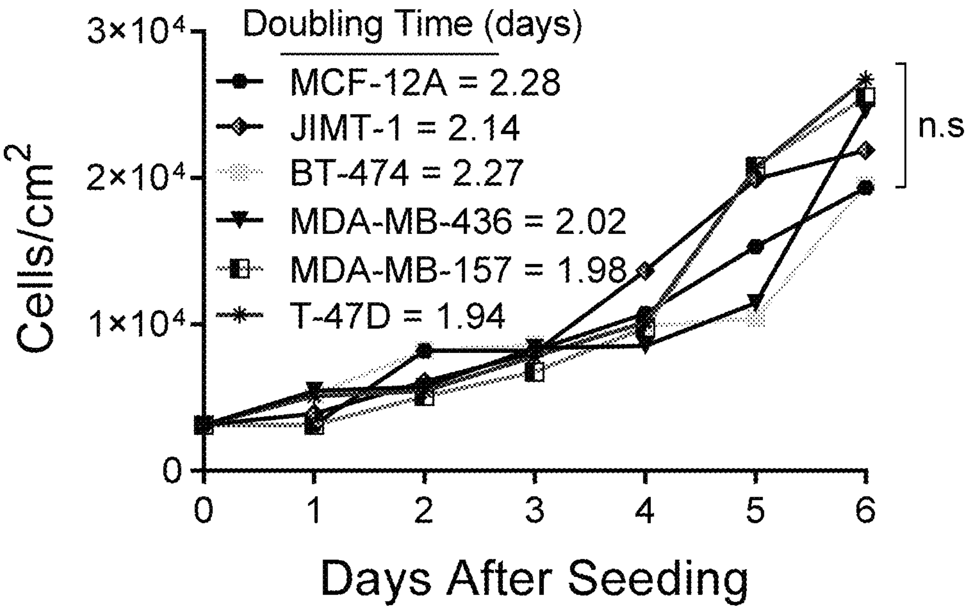
FIG. 7G shows the doubling time assessment of MCF-12A and breast cancer cell line models. Cells were plated at low density and grown for 1 week. They were then counted every day. One-way ANOVA test was used.
Figure 9A:
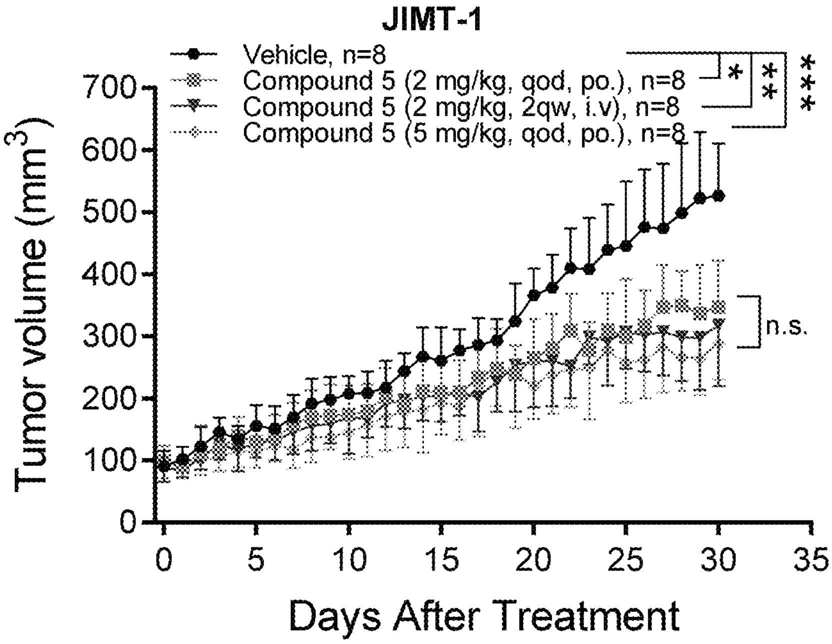
FIG. 9A shows tumor volume changes after the application of all three compound 5 groups with different dosage and administration routes.
Figure 9B:
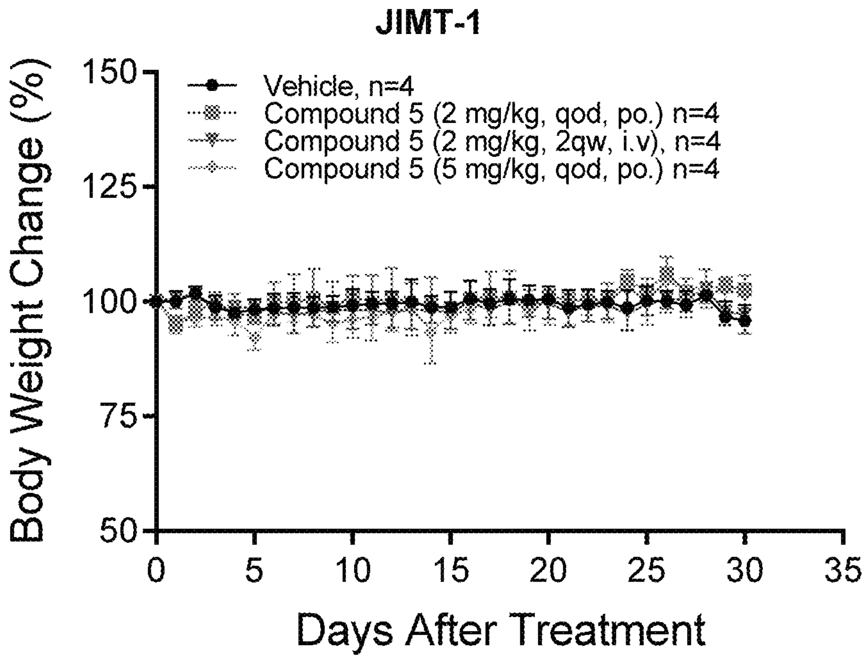
FIG. 9B shows mice body weight change during the course of treatment with different dosages and administration ways.
Figure 9C:
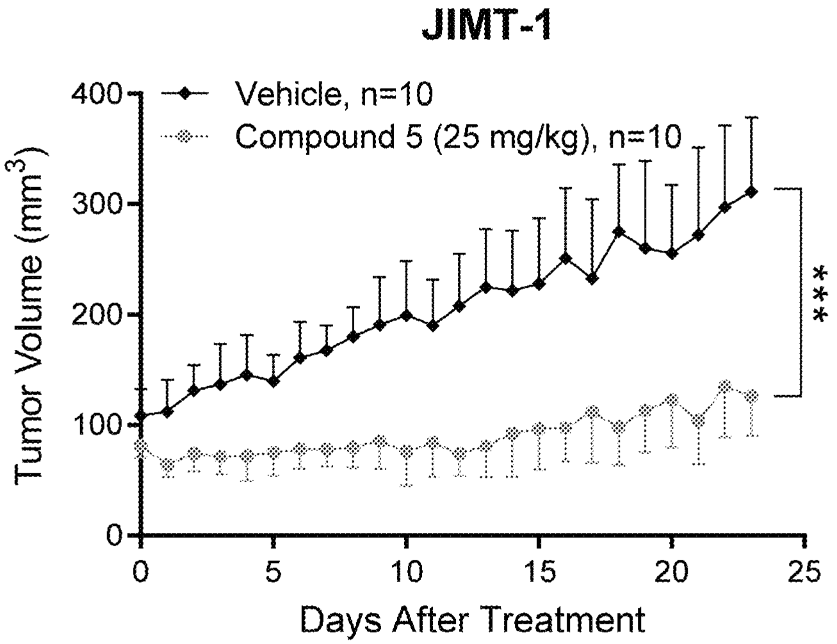
FIG. 9C shows tumor volume change of JIMT-1 xenografts after the treatment with vehicle or 25 mg/kg compound 5 in female nude mice. Treatments were started when tumors reached to 90-100 $mm^3$.
Figure 9D:
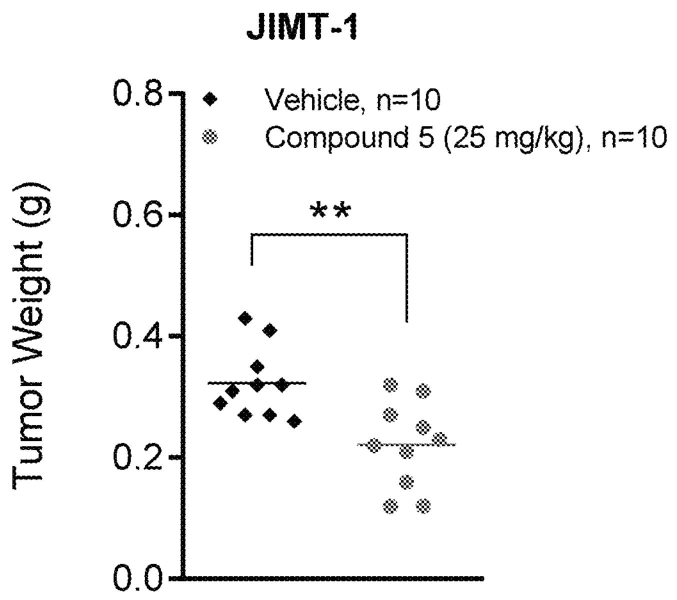
FIG. 9D shows the tumor weights of mice treated either with vehicle or compound 5.
Figure 9E:
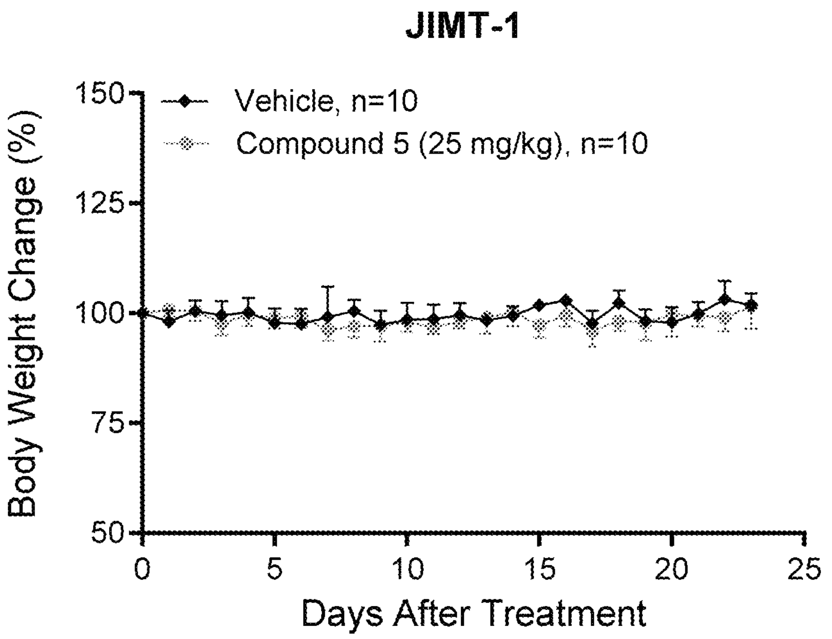
FIG. 9E shows the mice body weight change (%) following treatment.

Next, the specificity of compound 5 towards cancer cell lines over normal cells were tested. Therefore, the sensitivity of normal breast epithelial cells, MCF-12A, and several other breast cancer cells towards compound 5 was examined. Astonishingly, treatment even with high doses of compound 5 (5, 10 M) did not reach to 50% growth inhibition of cells (FIG. 7A) while compound 5 inhibited the viability of triple negative (MDA-MB-231, MDA-MB-436, CAL51 and HCC1143) and HER2-positive (JIMT-1 and HCC1954) breast cancer cell lines at lower doses compared to luminal (MCF7, T47D, ZR75 and BT-474) breast cancer cell lines (FIG. 7B). In other words, compound 5 specifically targets tumor cells while it is ineffective in normal breast cells. As shown in FIG. 6C, breast cancer cell lines that are more responsive to compound 5 express higher TACC3 levels than MCF-12A, further supporting the cancer specific high expression of TACC3. This shows that sensitivity to compound 5 correlates with aberrant TACC3 expression level in cancer cells. Besides, the low TACC3 levels might explain why MCF-12A cells did not respond to any of the TACC3 inhibitors at low doses. Moreover, a trend was observed for increased TACC3 expression in the two most aggressive breast cancer subtypes, TNBC and HER2-positive as compared to the luminal cell lines, suggesting that TACC3 expression might be associated with cancer aggressiveness. To test the transforming potential of TACC3 and dependency of cells to TACC3 to survive, we performed a clonogenic growth assay in MCF-12A cells after overexpressing TACC3. As shown in FIGS. 7D and 9E, TACC3 overexpression increased the colony formation capacity of the normal breast cell line, MCF-12A. Importantly, overexpression of TACC3 in MCF-12A cells renders them sensitive to the cytotoxic effects of compound 5, which further demonstrates the dependency of cells to TACC3 and the specificity of compound 5 (FIG. 7F). To exclude the possibility that the differences we observed between cancer and normal cells are due to the differences in the proliferation rates of these cells, we calculated their doubling times. As shown in FIG. 7G, there was no significant difference between the doubling times of MCF-12A and cancer cell lines, suggesting that responsiveness to compound 5 may not be dictated by increased rates of cell divisions.

Figure 8A:
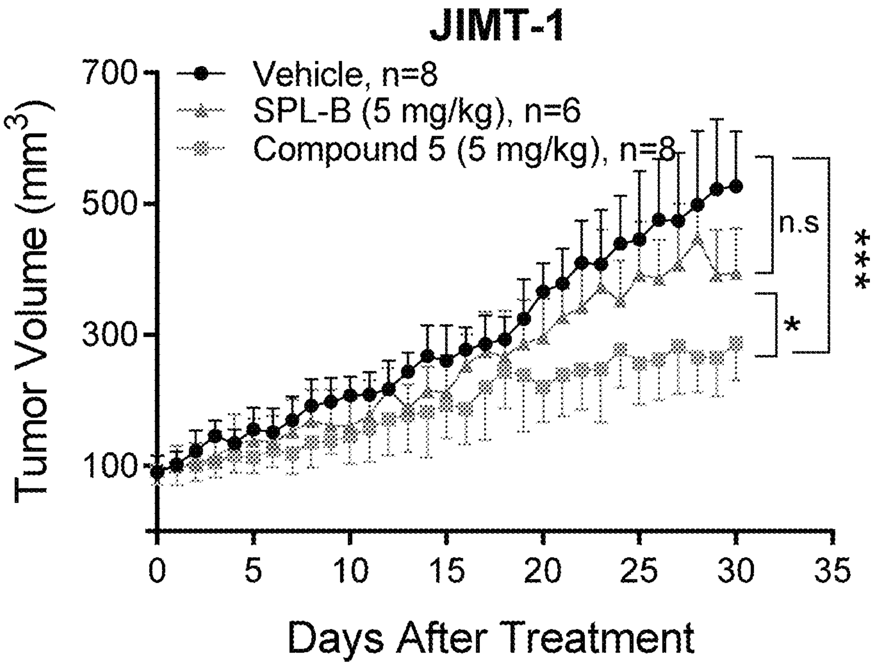
FIG. 8A shows the tumor volume change of JIMT-1 xenografts treated with vehicle, 5 mg/kg compound 5 or SPL-B orally for 30 days. Treatments were started when tumors reached to 90-100 $mm^3$.
Figure 8B:
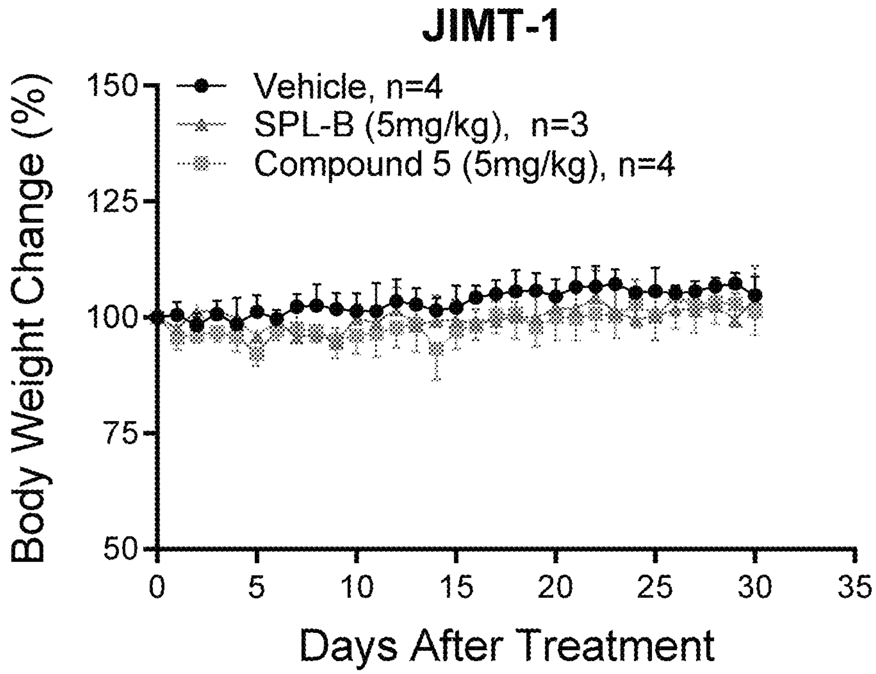
FIG. 8B shows the percent body weight changes of JIMT-1 xenografts followed for 30 days. *: p<0.05; : p<0.01; *: p<0.001; n.s: not significant.

The results described above demonstrated that breast cancer cells expressing high TACC3 levels are more sensitive to present novel disclosure TACC3 inhibitor, compound 5, in vitro. Therefore, the effect of compound 5 compared to SPL-B on tumor growth of highly tumorigenic breast cancer cell line JIMT-1 (Barok et al., 2007; Tanner et al., 2004) in immunodeficient mice was tested. For this purpose, female nude mice were injected with JIMT-1 cells into mammary fat pad (MFP) and subsequently treated with vehicle or 5 mg/kg (oral) compound 5 or SPL-B was applied every other day for 30 days. It was concluded that compound 5 showed significant reduction of tumor growth as compared to SPL-B, and there was no major effect on the body weight of mice (FIG. 8).

Figure 10A:
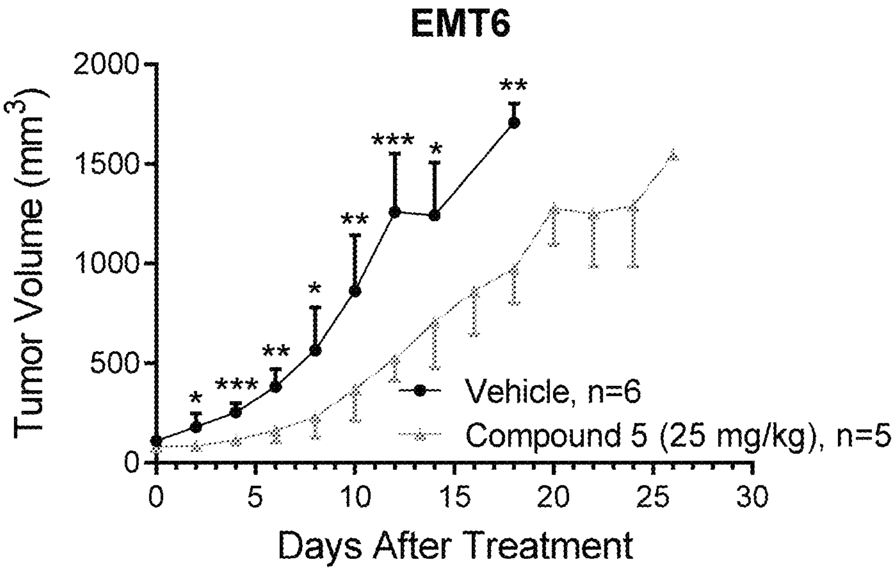
FIG. 10A shows the tumor volumetric assessment of the effect of compound 5 on a highly aggressive syngeneic mouse breast cancer model, EMT6 xenografts. Significance was calculated using multiple t-test for each data point for each day compared to vehicle control. *: $p<0.05$; : $p<0.01$; *: $p<0.001$.
Figure 10B:
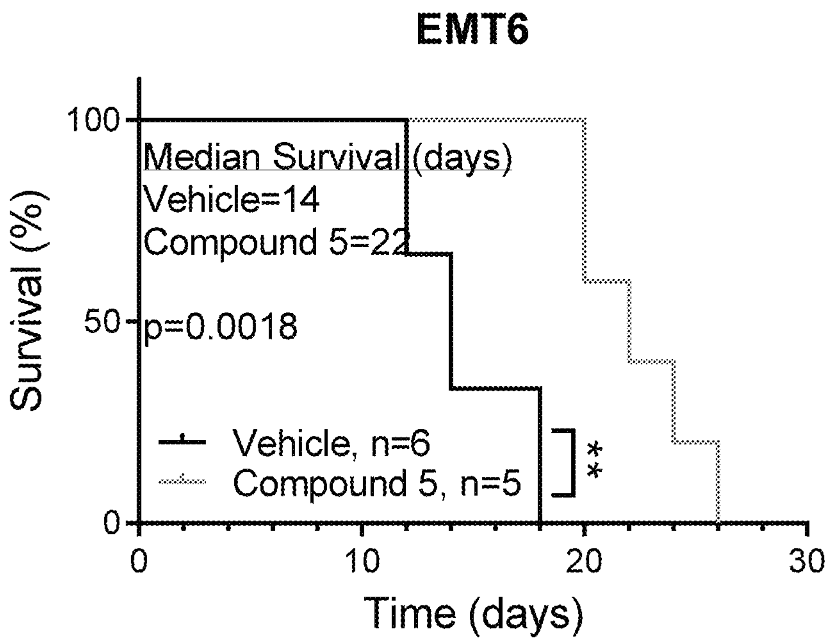
FIG. 10B is a Kaplan-Meier survival curve of EMT6 xenografts treated with vehicle (median survival 14 days) or compound 5 (median survival 22 days). P value was calculated using the log rank test.
Figure 10C:
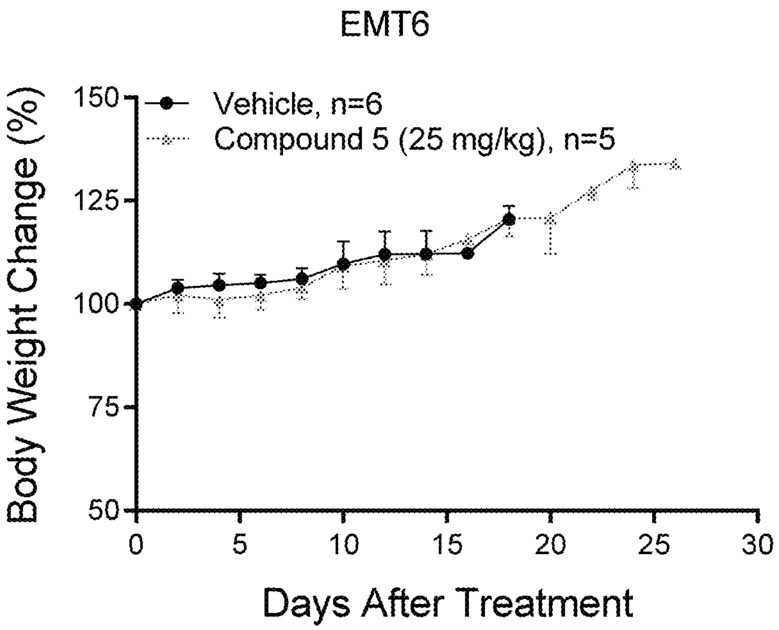
FIG. 10C shows the percent body weight changes of EMT6 xenografts following treatment.
Figure 11A:
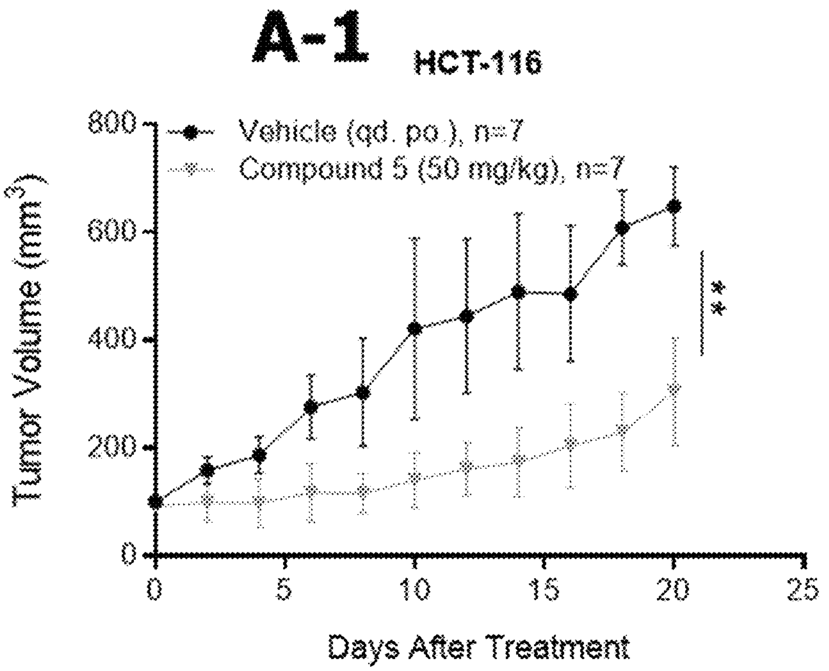
FIG. 11A shows the tumor volumetric assessment of the effect of compound 5 on colorectal carcinoma xenografts of immunocompromised (HCT-116) and syngeneic immunocompetent (CT-26) mice models. Mice were treated with vehicle or compound 5 (25 and/or 50 mg/kg) every day orally. Treatments were started when tumor volume reached to 90-100 $mm^3$. Significance was calculated using student t-test. *: $p<0.05$; : $p<0.01$.
Figure 11A:
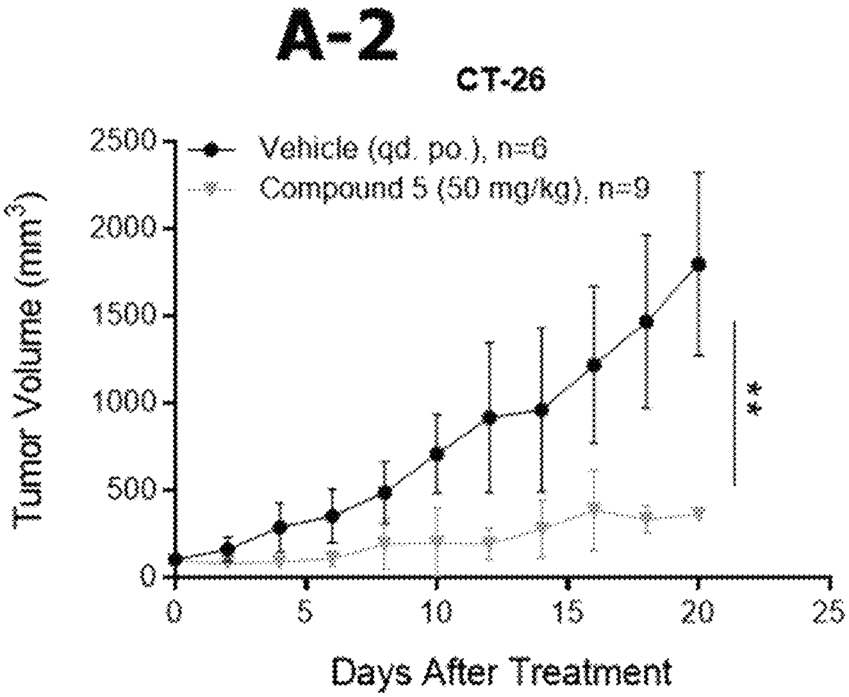
Figure 11B:
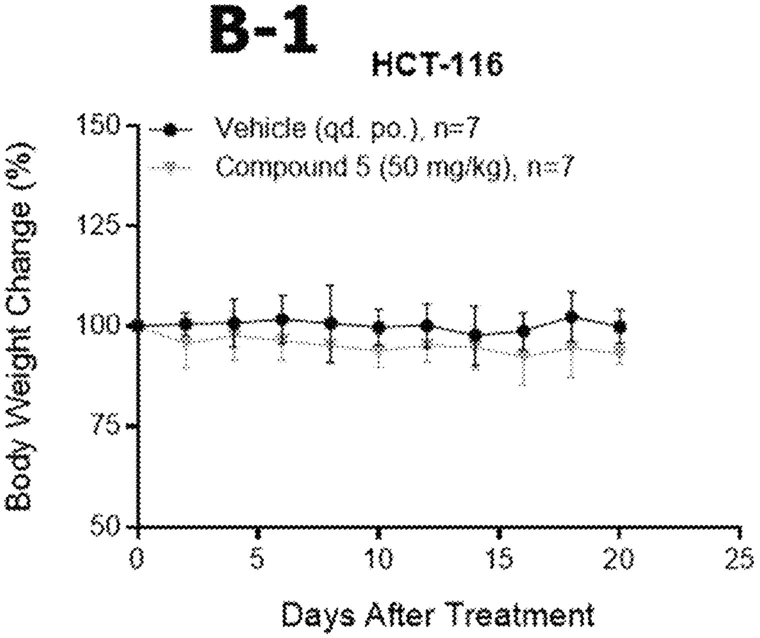
FIG. 11: Generally.
Figure 11B:
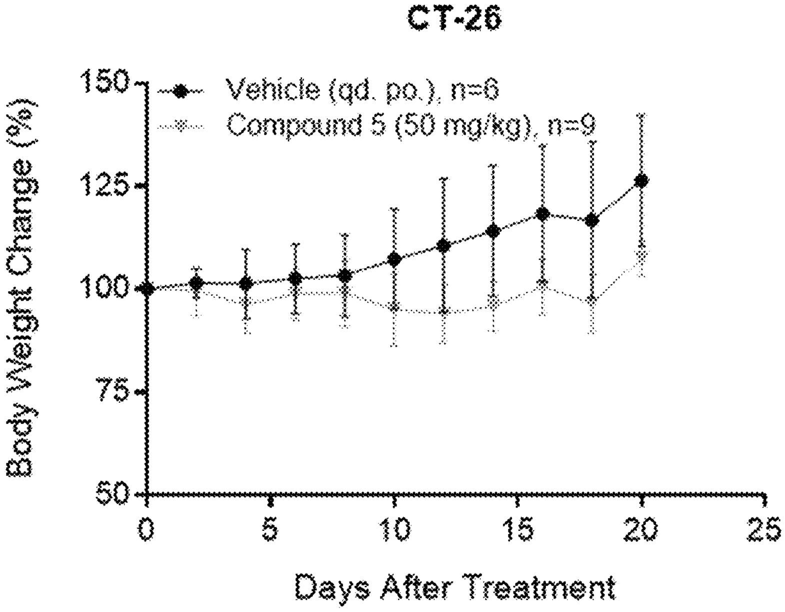

Then, different doses and administration routes of low dose compound 5 were tested using JIMT-1 xenografts. Compound 5 at doses, 2 mg/kg (po. or i.v) or 5 mg/kg (po.) every two days for 30 days, was administered into mice (FIG. 9). Tumor growth rate of all three compound 5-administrated group decreased when compared with control group and among these group (FIG. 9A). It is indicated in FIG. 9B that the administration of compound 5 did not have any negative effect on the body weight of mice. Moreover, to test the effect of a higher compound 5 dose on tumor growth compared to previous experiments to obtain better anti-tumor effect and test its tolerability, female nude mice were injected with JIMT-1 cells into mammary fat pad (MFP) and subsequently treated with vehicle or compound 5 (25 mg/kg, po.) for 23 days. Compound 5 showed very significant reduction of tumor growth compared to vehicle-treated mice (FIG. 9C). Tumor weights were significantly lower when compared to the ones of vehicle group (FIG. 9D). Importantly, compound 5 was well tolerated since the treatment did not affect the mice weight (FIG. 9E). The effect of TACC3 inhibition was also tested in vivo using an immunocompetent mouse model (FIG. 10). Murine triple negative breast cancer (TNBC) cell line, EMT6, which is a fast-growing and highly aggressive model (Yang, Yang et al. 2017), was injected into MFPs of syngeneic Balb/c mice. A significant tumor growth inhibition (FIG. 10A) and 57.1% increased lifespan (FIG. 10B) was observed in compound 5-treated mice compared to vehicle treated ones. Moreover, compound 5 was again well tolerated in the syngeneic mouse model (FIG. 10C).

In addition to breast cancer xenografts and syngeneic models, anti-tumorigenic capacity of compound 5 was tested on colon carcinoma animal models (FIG. 11). Female nude mice and Balb/c mice were injected with human colon carcinoma cell line, HCT-116, and murine colon carcinoma cell line, CT26, respectively, into flank region of mice. Mice were treated with either vehicle or 25-50 mg/kg compound 5 daily and orally. Similar to breast cancer models, compound 5 significantly impaired tumor growth (FIG. 11A) and was well tolerated in both models (FIG. 11B).

Figure 12A:
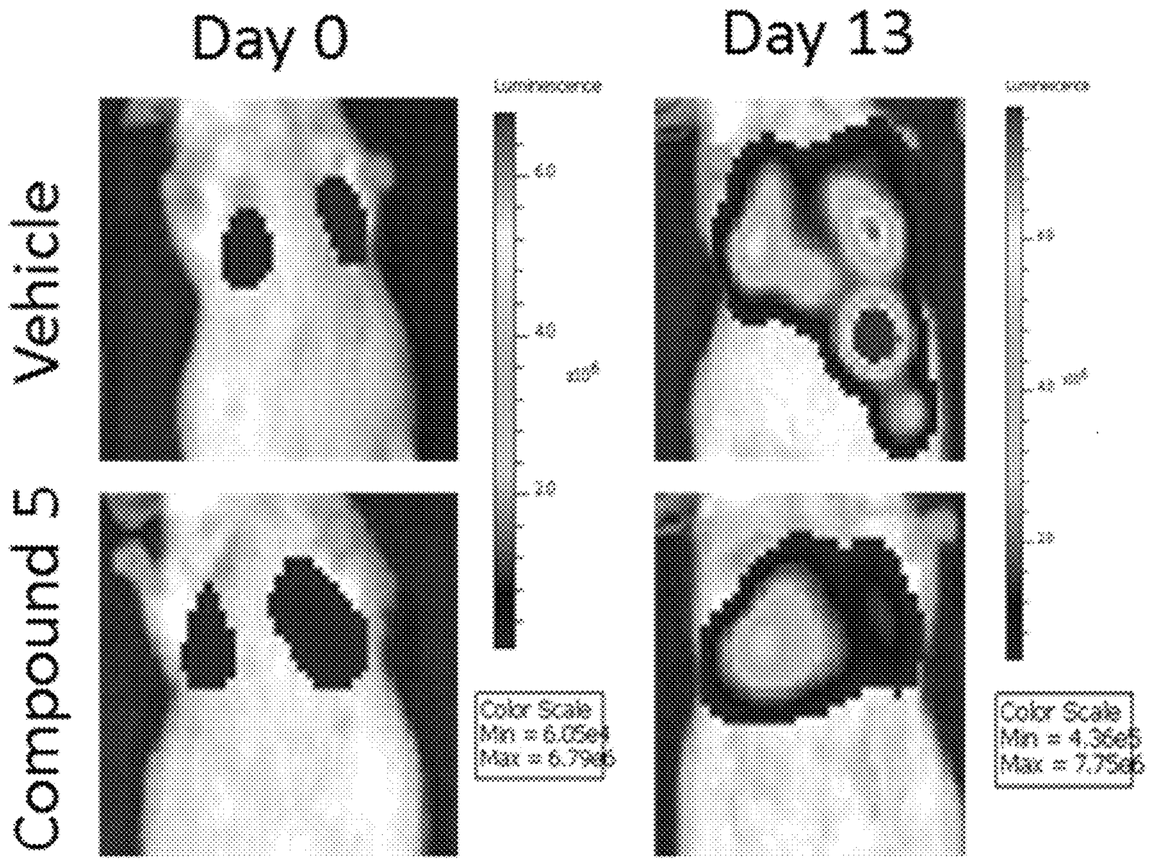
FIG. 12A shows bioluminescence (BLI) images of mice injected with 4T1.luc2 cells into tail-vein. After metastasis is established in the lungs, mice were treated either with vehicle or compound 5 (50 mg/kg) every day orally. Metastatic growth was monitored by BLI once a week with IVIS (in vivo imaging system).
Figure 12B:
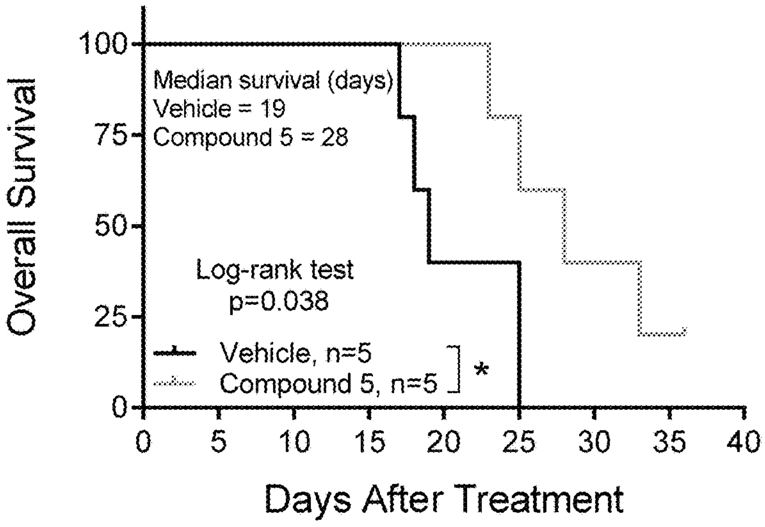
FIG. 12B is a Kaplan-Meier survival curve of 4T1.luc2 syngeneic model treated with vehicle (median survival 19 days) or compound 5 (median survival 28 days). P value was calculated using the log-rank test.

Next, to examine the effects of TACC3 inhibition on metastatic growth, an aggressive murine mammary tumor cells, 4T1-Luc2 (luciferase labelled), were injected intravenously to immunocompetent female mice. Here, the aim was to determine the effect of compound 5 on metastatic outgrowth and lung colonization using clinically relevant metastasis models. When mice showed metastatic lesions at the lungs, they were treated with either vehicle or 50 mg/kg compound 5 daily. Metastatic outgrowth was monitored with in vivo imaging system (IVIS) by measuring bioluminescence. Compound 5 was found to impair metastatic growth compared to vehicle (FIG. 12A) and significantly improved mice overall survival (FIG. 12B).

Figures 13A, 13B, 13C:
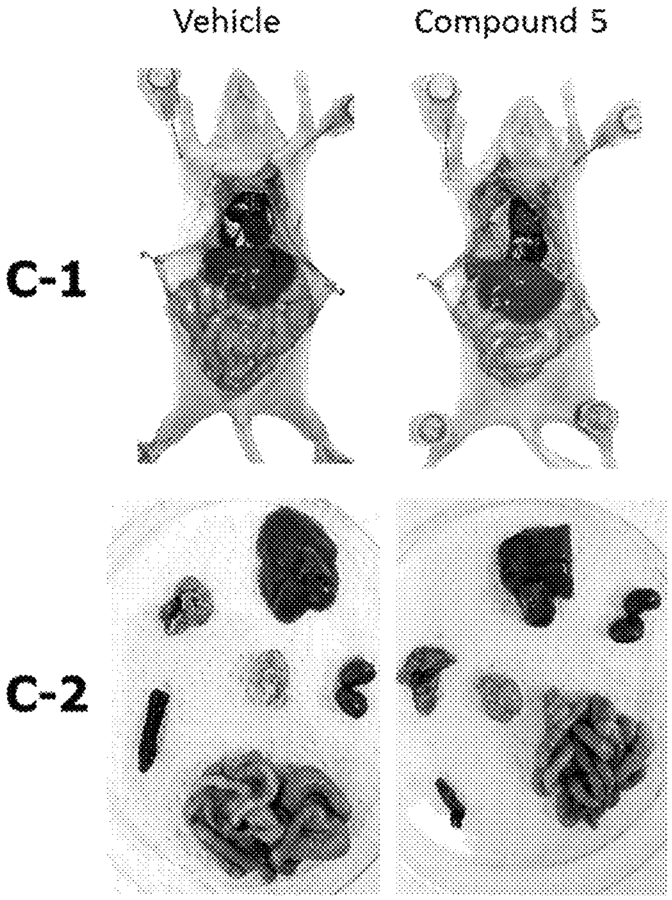
FIG. 13A shows mice body weight (g) after daily oral administration of 100 mg/kg compound 5 for 7 days.
FIG. 13B shows, ice body weight (g) after a single-dose administration of compound 5 (500 mg/kg). Mice were sacrificed at different days.
FIG. 13C are photos of mice and their organs (lower panel) treated with either vehicle or 500 mg/kg compound 5. They were sacrificed 48 h after drug treatment.

Lastly, to determine the maximum tolerated dose, nude female mice received 100 mg/kg compound 5 daily for 7 days and body weight are recorded (FIG. 13A). Compound 5 did not affect body weight and did not create any observable toxicity at this high dose. In another experiment, mice were given 500 mg/kg compound 5 only once and monitored for 1-3 days. Mice receiving compound 5 had a 10% loss of their body weight 24 h after drug treatment, but their general condition was stabilized (FIG. 13B). Organs were collected at the end of the experiment, and no organ toxicity was observable indicating that compound 5 was well tolerated (FIG. 13C).

On the basis of the overall profile, compound 5 was evaluated for its physiochemical properties and metabolic stability. Compound 5 has a medium lipophilicity with a log $D_{7.4}$ of 2.3 and demonstrated low solubility as well as low stability in both human and mouse liver microsomes, and relatively high plasma protein binding (unbound fraction of 1.13%), but good Caco-2 permeability with a low efflux ratio (AB=$190\times10^{-6}$ nm/s, ratio=<2.0) (Table 1). Concordantly, cytochrome P450 inhibition by compound 5 in human liver microsomes was also characterized in order to evaluate potential drug-drug interactions (Lin & Lu, 1998) (Table 1). Accordingly, compound 5 was a moderate inhibitor of CYP2C9 ($IC_{50}$=2.63 μM) and CYP3A (testosterone as substrate; $IC_{50}$=8.59 M) whereas it was a weak or not an inhibitor of CYP2CD6 ($IC_{50}$=18.46 M) and CYP3A ($IC_{50}$=midazolam as substrate; 30.04 M), indicating that compound 5 has low activity on the tested P450 cytochromes.

Biological Materials and Methods

Cell Culture and Reagents

Human breast cancer cell lines MDA-MB-436, MDA-MB-157, MDA-MB-231, BT-474, MCF-7, ZR-75-1 and T-47D, mouse mammary tumor cell lines EMT6 and 4T1, human bladder cancer cell lines RT112 and RT4, mouse colon carcinoma cell line CT-26, and normal human breast epithelial cell line MCF-12A were purchased from ATCC. T-DM1 resistant HER2-positive breast cancer cell line BT-474 T-DM1R was developed and characterized as described previously (Saatci et al., 2018). Human colon carcinoma cell line HCT-116 was a kind gift from Serkan Göktuna from Bilkent University, Ankara, Turkey. JIMT-1, HCC1954, CAL51 and HCC1143 were kindly provided by Ali Osmay Gure from Bilkent University. Cells were cultured in Dulbecco's modified Eagle's medium (Lonza, NJ, USA), supplemented with 10% fetal bovine serum (FBS, Lonza), 1% non-essential amino acid (NEAA), 2 mM L-glutamine (Sigma Aldrich, MO, USA) and 50 U/ml penicillin/streptomycin (P/S). BT-474 WT and T-DM1R cells were also supplemented with 0.1% insulin (Sigma Aldrich). In addition, MCF-12A cells were supplemented with 20 ng/ml epidermal growth factor (EGF) and 500 ng/ml hydrocortisone containing medium. T-47D and MCF-7 cells were cultured in phenol red-free DMEM (Gibco, Carlsbad, CA) with 10% FBS, 1% NEAA, 1% L-glutamine, 50 U/ml P/S and 0.1% insulin. EMT6, 4T1, CT-26 and RT112 cells were maintained in RPMI-1640 (Biowest, Nuaille, France) while RT4 and HCT-116 cells were cultured in McCoy's 5A (modified) (Gibco) medium supplemented with FBS, NEAA, L-glutamine and P/S. All cell lines were tested regularly using MycoAlert Mycoplasma Detection Kit (Lonza).

Isothermal Titration Calorimetry (ITC)

Purified TACC3 recombinant protein (TP310754; Origene, MD, USA) and compound 5 (5) were prepared in 25 mM Tris·HCl, pH 7.3, 100 mM glycine, 10% glycerol solution. compound 5 (5) was loaded into the sample cell and titrated with TACC3 protein (10-fold higher concentration in the syringe) in duplicate experiments. Titrations were carried out using Microcal 200 equipment (GE Healthcare, Austria) at 25° C. For each titration, 10 injections were made with 6 min spacing. The reference power was set at 2 cal/see, and the sample cell was continuously stirred at 500 rpm. In order to assess the binding efficiency between drug and protein, background data obtained by protein injected into buffer alone was subtracted from the experimental isotherms. The data was analyzed using Origin 7 Software provided along with the ITC200, and binding parameters such as association constant (Ka), number of binding sites (N) and enthalpy (ΔH) were calculated.

Drug Affinity Responsive Target Stability (DARTS)

DARTS was performed as previously described [[(26)]]. Briefly, JIMT-1 cells were grown to 70-80% confluency and lysed in RIPA lysis buffer without SDS and sodium deoxycholate. Concentration of the protein extract was determined with BCA Protein Assay Reagent Kit (Thermo Scientific, IL, USA) and diluted to 4 g/l in lysis buffer. Cell lysate was split into aliquots of 99 μl and mixed with 1 μl of 100× concentrated solutions of 10 uM of compound 5 and SPL-B, separately. Cell lysate-drug mixtures were incubated at room temperature on a shaker for 20 minutes to allow binding. Later, 20 μl of each sample was mixed with 2 μl of 8 ng/l pronase solution (Sigma Aldrich) or buffer only (undigested) and incubated at room temperature for 12 minutes. Protein digestion was stopped by adding 2 μl of 20× protease inhibitor (Roche, Switzerland) and incubating on ice for 10 min. Then, lysates were mixed with 8 μl of 4×SDS loading buffer and heated at 70° C. for 10 min. SDS-PAGE was performed with anti-TACC3 and anti-CDK4 antibody as negative control.

Inhibitor Treatments, Cell Viability Assays and Annexin V/PI Staining

KHS101 (Sigma Aldrich) and SPL-B (Axon MedChem, VA, USA) were dissolved in 100% DMSO to yield a stock concentration of 50 mM. Newly synthesized molecules were dissolved in 100% DMSO to yield a stock concentration of 10 mM. For cell viability assay, JIMT-1 ($3\times10^3$ cells/well), BT-474 WT and T-DM1R ($6\times10^3$), MDA-MB-436 ($4\times10^3$), MDA-MB-157 ($3\times10^3$), HCC1954 ($5\times10^3$), CAL51 ($5\times10^3$), HCC1143 ($4.5\times10^3$), MDA-MB-231 ($4.5\times10^3$), MCF-7 ($7\times10^3$), T-47D ($6\times10^3$), RT112 ($6\times10^3$), RT4 ($6\times10^3$), and MCF-12A ($5\times10^3$) cells were seeded into 96-well plates, and 24 hours after cell seeding inhibitor treatments were performed at different concentrations. Cell viability was measured 72 hours after treatment with Sulforhodamine B (SRB, Sigma Aldrich) assay as recommended by the manufacturer. For western blotting, different concentrations of KHS101, SPL-B or compound 5 were given to JIMT-1 ($1.5\times10^5$) and RT112 ($2\times10^5$) cells for 24 hours. Annexin V/PI staining (Biolegend, USA) was performed according to manufacturer's instructions using JIMT-1 cells treated with 500 nM compound 5 for 48 hours.

Transient Transfection with siRNAs and Overexpression Vectors

For cell viability assays, JIMT-1 ($3\times10^3$ cells/well), BT-474 T-DM1R ($6\times10^3$), MDA-MB-436 ($4\times10^3$) and MDA-MB-157 ($3\times10^3$), cells were seeded into 96-well plates in P/S-free growth medium. 24 hours after seeding, cells were transfected with two different siRNAs targeting TACC3 (Dharmacon, CO, USA) at a final concentration of 20 nM (siTACC3 #1: D-004155-03 and siTACC3 #2: D-004155-02) using Lipofectamine 2000™ (Invitrogen, CA) transfection reagent as described previously (Mutlu et al., 2016). 72 hours following transfection, cell viability was measured using SRB assay. To assess the TACC3 knockdown levels upon siRNA transfections, JIMT-1 ($1.5\times10^5$), BT-474 T-DM1R ($2\times10^5$), MDA-MB-436 ($1.5\times10^5$) and MDA-MB-157 ($1.5\times10^5$) cells were transfected with two different TACC3 siRNAs for 48 hours. Knockdown efficiency at mRNA and protein levels was analyzed by quantitative real-time PCR (qRT-PCR) and western blotting, respectively. For transient TACC3 overexpression, MCF-12A cells were transfected with 250 ng of empty or TACC3 vector (OHu21751; Genscript, NJ, USA) for 48 hours.

Colony Formation Assay

For monolayer culture, single-cell suspensions of JIMT-1 cells ($3\times10^3$ cells/well) were plated in a 12-well plate. After 6 hours incubation, cells were treated with different doses of compound 5 (5), SPL-B and KHS101. In order to test the colony formation capacity of MCF-12A cells during TACC3 overexpression, MCF-12A cells ($2\times10^5$) were seeded into 6-well plates and TACC3 transfection was performed next day. 48 h following transfection, cells were counted and $1\times10^3$ cells/well were plated into 12-well plates. For both experimental setups, the media were refreshed every 4 days, and cells were incubated for 12 days. Cells were then fixed with 2% paraformaldehyde for 15 min and stained with 1% crystal violet (Merck, Darmstadt, Germany) for 15 min at RT. Surviving colonies (composed of at least 50 cells) were counted with ImageJ software (NIH).

Doubling Time Assessment

To assess doubling time, normal breast epithelial cell line MCF-12A and breast cancer cell lines were plated ($3\times10^4$ cells/well) in 6-well plates. Cells were collected by trypsinization and cell number was counted every 24 h for one week. Growth curves for these cells were drawn as number of cells/$cm^2$ versus days after seeding. The doubling time was calculated using the following formula;

$$\text{Doubling time } (DT) = \frac{t \times \ln 2}{\ln\left(\frac{Xe}{Xb}\right)}$$

where t is the time spent in the logarithmic phase of cell growth, Xe and Xb are cell numbers at the end and beginning of the logarithmic phase, respectively.

Immunofluorescence

Immunofluorescence staining of JIMT-1 cells were performed as previously described (Cizmecioglu, Arnold et al. 2010). Basically, $1.5\times10^5$ JIMT-1 cells/well were seeded on glass coverslip in 6-well plates. Next day, the cells were treated with either vehicle, 200 nM or 500 nM compound 5 for 12 hours. Then, they are fixed with ice-cold methanol for 10 min at −20° C. Cells were then blocked with 3% BSA in PBS solution for 1 hour at RT and incubated with primary and secondary antibodies for 1 hour at RT. Cells were counter stained with DAPI for 5 min (0.01 g/ml). Lastly, cover slides were mounted using ImmunoHistomounth (Santa Cruz). Images were taken with an upright fluorescent microscope equipped with DIC prisms (upright).

NCI-60 Cancer Cell Line Panel Screening

Compound 5 (5) was submitted to the National Cancer Institute (NCI number S807620) for screening in the NCI-60 panel of human tumor cell lines, which consists of 60 human cancer cell lines from 9 different cancer types. compound 5 (5) was first tested in a single-dose screen at a concentration of 10 μM in each cell line. After obtaining the results for the single dose assay, an analysis of the Development Therapeutics Program (DTP) was performed, and compound 5, which satisfied the predetermined threshold inhibition criteria, was selected for the NCI full panel 5 doses assay. compound 5 was then tested twice in the five-dose NCI-60 screen at doses ranging from 10 nM to 100 μM, which determines the $GI_{50}$ (50% growth inhibition), TGI (total growth inhibition) and $LC_{50}$ (lethal dose concentration inducing 50% cell death) values for 60 cell lines. Detailed screening methodology can be accessed from https://dtp.cancer.gov/discovery_development/nci-60/methodology.htm webpage. Briefly, 24 h after cell seeding into 96-well plates, cells were treated with 5-log M concentration range of the compound for 2 days. Cytotoxicity was assessed using SRB assay. The data presented in the FIGS. are the average values of both experiments.

Mice Experiments

Six-to-eight-week-old female athymic nude or Balb/c mice were housed with a temperature-controlled and 12-hour light/12-hour dark cycle environment. This study was carried out in accordance with Institutional Animal Care and Use Committee of Bilkent University and performed according to the institution's guidelines and animal research principles. For in vivo breast cancer tumor growth in nude mice, $4\times10^6$ JIMT-1 cells were prepared in 150 μl of 1:1 DMEM and Matrigel (Corning, NY, USA), v/v) and injected into the mammary fat pads (MFP) of female nude mice. Mouse weight and tumor volume were measure daily using calipers. Tumor volumes were calculated as length$\times$width$^2\times$ 0.5. Once the tumor volume had reached about 90-100 $mm^3$, xenografts were randomized into groups. Animals were treated with vehicle (0.05% HPMC (hydroxypropyl methylcellulose) in ddH2O and 2% Tween-80), or compound 5 (every other day (qod.) at different doses—po. or iv. and administration ways—2 or 5 mg/kg). In a separate experiment, animals were also tested for a higher dose of compound 5 (25 mg/kg). The effect of compound 5 (5 mg/kg, qod., po.) on tumor growth was also compared with SPL-B (5 mg/kg, qod., po.) using JIMT-1 cells. Mice were sacrificed 20-30 days after initiation of the treatments, and the tumors were collected and stored for subsequent analyses. In order to test compound 5 effect in an immunocompetent female Balb/c mice model, an aggressive mouse breast cancer cell line was used. $1\times10^6$ EMT-6 cells were prepared in PBS and injected into MFPs of mice. Similarly, once the tumor volume had reach to 90-100 $mm^3$, mice were randomized into two groups and received either vehicle or 25 mg/kg compound 5 every day orally. Survival was calculated using a predefined tumor volume cut-off of 1500 $mm^3$.

Additionally, compound 5 was tested upon induction of lung metastasis. Highly aggressive and metastatic 4T1-Luc2 (luciferase labelled) cells were prepared in PBS as $1\times10^6$ cells/mouse and injected intravenously to Balb/c female mice. Metastasis development was monitored using in vivo imaging system (IVIS) and bioluminescence was quantified regularly. Once lung metastases were developed, mice were randomized into two groups and received either vehicle or 50 mg/kg compound 5 every day orally. Survival was calculated when mice died.

In addition to breast cancer models, anti-tumorigenic effects of compound 5 was tested in colon carcinoma animal models both in immunodeficient nude mice (for HCT-116) and syngeneic immunocompetent Balb/c mice (for CT-26). $4\times10^6$ HCT-116 and $1\times10^6$ cells were prepared either in matrigel:PBS or in PBS, respectively, and injected subcutaneously into flank region of mice. Similarly, once the tumor volume had reach to 90-100 $mm^3$, mice were randomized into two groups and received either vehicle or 25-50 mg/kg compound 5 every day orally for 20-25 days. Mice body weight was measured regularly.

For toxicity analysis, nude female mice received 100 mg/k compound 5 for 7 days or received vehicle or 500 mg/kg compound 5 once orally. Mice body weight was measured regularly, and organs were collected for determination of possible toxicity.

Bioinformatics Analyses

TACC3 differential plot between different tumor and normal tissues was constructed using The Cancer Genome Atlas (TCGA) patients (Akbani et al., 2014) and data was downloaded from http://firebrowse.org/. For survival analysis and prognostic significance of TACC3, different independent publicly available cancer datasets were used. One is the Molecular Taxonomy of Breast Cancer International Consortium (METABRIC) dataset (Curtis, Shah et al. 2012). TACC3 expression levels of METABRIC Discovery and Validation set was used for overall survival of breast cancer patients. Patients from 25th and 75th quartiles of TACC3 levels were used and defined as low and high TACC3, respectively. The association between TACC3 expression and patient overall survival of gastric cancer was analyzed using Kaplan Meier plotter database, which includes information on overall survival of 876 gastric cancer patients (Szasz et al., 2016). Data for disease free survival of prostate cancer patients composed of 122 patients were retrieved from The Cancer Genome Atlas (TCGA) database using https://www.cancer.gov/tega and patients were spearated based on $25^{th}$ and $75^{th}$ percentiles. Finally, relapse free survival data of lung cancer patients were obtained from GSE31210 dataset and similarly, $25^{th}$ and $75^{th}$ percentile of patients were used for this analysis (Okayama, Kohno et al. 2012). Gene set enrichment analysis (GSEA) analysis of mitosis and DNA repair-related gene sets, available at the Broad Institute website (http://software.broadinstitute.org/gsea/index.jsp), was done using breast cancer METABRIC Validation data set (n=995) where patients were divided into two groups (high vs. low) based on TACC3 expression levels. For the analysis of TACC3 dependency of NCI-60 cell lines, we used dependency data from combined RNAi screens of Broad Institute, Novartis and Marcotte et al. (13) which is available in https://depmap.org/portal/. Multivariate Cox regression analysis was done using METABRIC dataset in SPSS software. TACC3 level, tumor grade, tumor stage, ER, PR and HER2 status were selected as covariates. TACC3 expression was separated based on 25th percentiles.

Statistical Analyses

Data were analyzed using GraphPad Prism software (GraphPad Software, Inc) and expressed as mean±standard deviation from three independent experiments unless otherwise indicated. Statistical significance of two group comparisons was determined by two-tailed Student's t-test. To compare the doubling time curves of different cell lines, one-way ANOVA was used. A multiple t-test was used to determine pair-wise significances between the treatment groups of tumor volumes of EMT6 xenografts. A p and an adjusted p (q) value of less than 0.05 were considered to be statistically significant. Kaplan-Meier survival curve analysis was performed using Log-rank (Mantel-Cox) test.

Example 3: Further Exemplary Biological Results

| | JIMT-1 | | JIMT-1 |
|---|---|---|---|
| 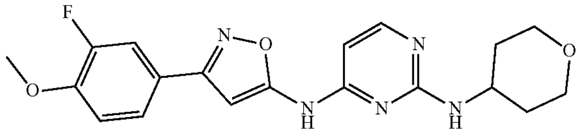 [SMILES: COc1ccc(-c2cc(Nc3ccnc(NC4CCOCC4)n3)on2)cc1F] | 18.5 | 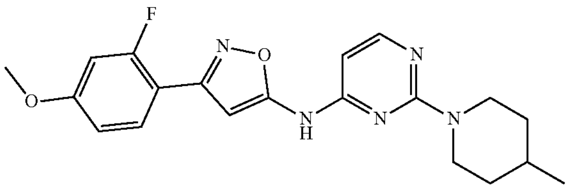 | |
| 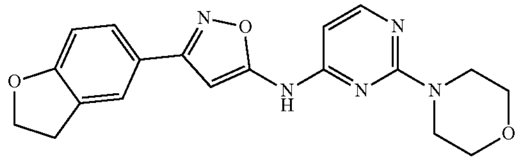 [SMILES: c1cc(Nc2cc(-c3ccc4c(c3)CCO4)no2)nc(N2CCOCC2)n1] | 0.417 | 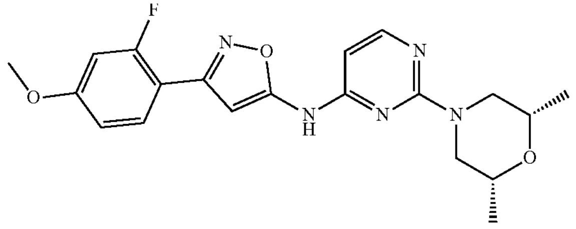 | |
| 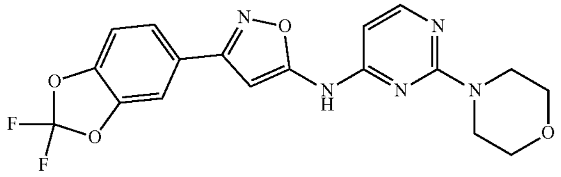 [SMILES: FC1(F)Oc2ccc(-c3cc(Nc4ccnc(N5CCOCC5)n4)on3)cc2O1] | >10 | 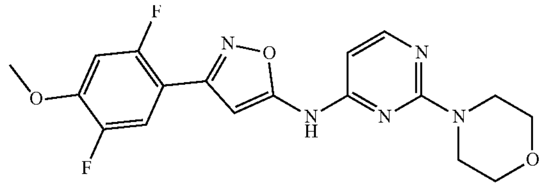 [SMILES: COc1cc(F)c(-c2cc(Nc3ccnc(N4CCOCC4)n3)on2)cc1F] | |
| 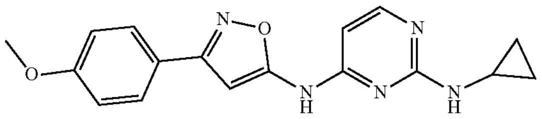 [SMILES: COc1ccc(-c2cc(Nc3ccnc(NC4CC4)n3)on2)cc1] | 0.108 | 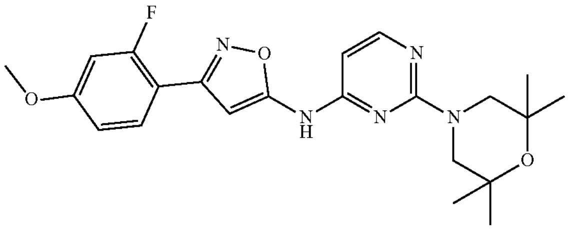 | |

-continued
| | JIMT-1 | | JIMT-1 |
|---|---|---|---|
| 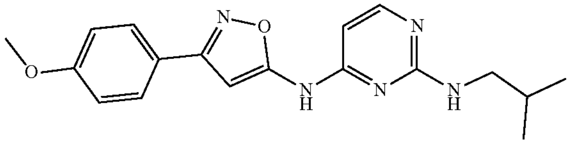 [SMILES: COc1ccc(-c2cc(Nc3ccnc(NCC(C)C)n3)on2)cc1] | 0.429 | 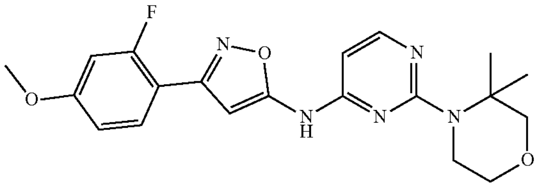 | |
| 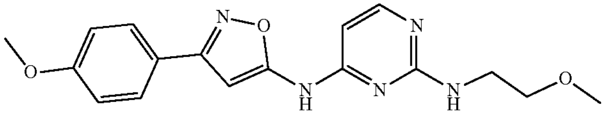 | 0.694 | 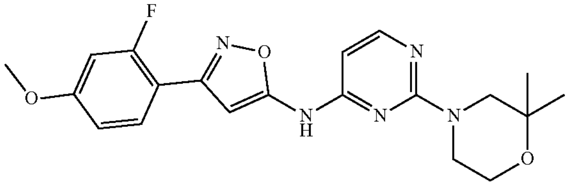 | |
| 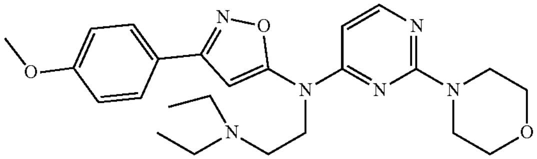 [SMILES: CCN(CC)CCN(c1ccnc(N2CCOCC2)n1)c1cc(-c2ccc(OC)cc2)no1] | >10 | 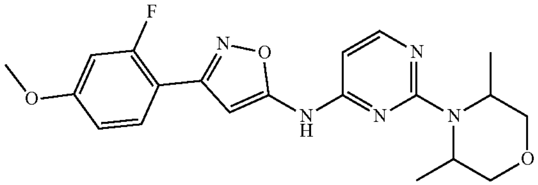 [SMILES: COc1ccc(-c2cc(Nc3ccnc(N4C(C)COCC4C)n3)on2)c(F)c1] | |
| 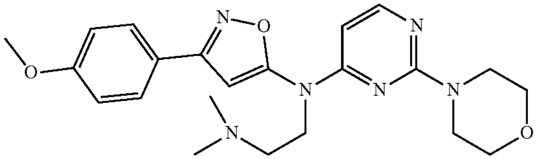 [SMILES: COc1ccc(-c2cc(N(CCN(C)C)c3ccnc(N4CCOCC4)n3)on2)cc1] | >10 | 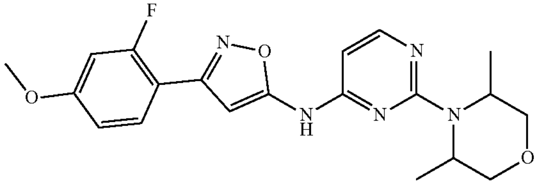 [SMILES: COc1ccc(-c2cc(Nc3ccnc(N4C(C)COCC4C)n3)on2)c(F)c1] | |
| 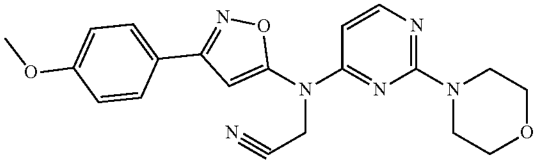 [SMILES: COc1ccc(-c2cc(N(CC#N)c3ccnc(N4CCOCC4)n3)on2)cc1] | >10 | 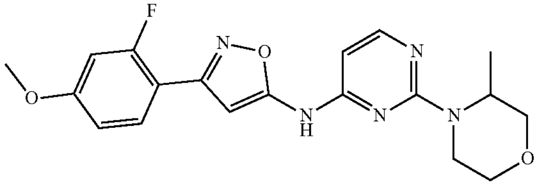 [SMILES: COc1ccc(-c2cc(Nc3ccnc(N4CCOCC4C)n3)on2)c(F)c1] | |

-continued
| | JIMT-1 | | JIMT-1 |
|---|---|---|---|
| 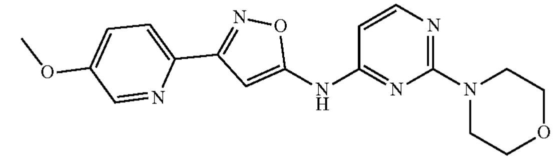 [SMILES: COc1ccc(-c2cc(Nc3ccnc(N4CCOCC4)n3)on2)nc1] | >10 | 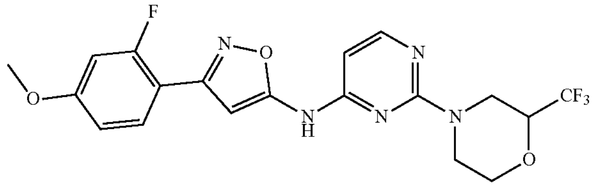 [SMILES: COc1ccc(-c2cc(Nc3ccnc(N4CCOC(C(F)(F)F)C4)n3)on2)c(F)c1] | |
| 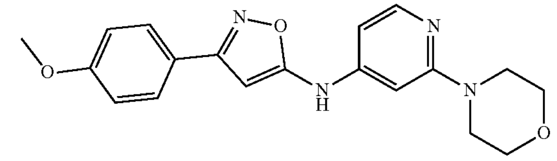 [SMILES: COc1ccc(-c2cc(Nc3ccnc(N4CCOCC4)c3)on2)cc1] | >10 | 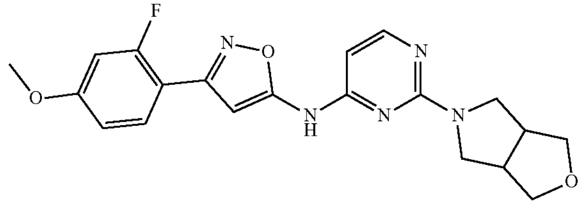 [SMILES: COc1ccc(-c2cc(Nc3ccnc(N4CC5COCC5C4)n3)on2)c(F)c1] | |
| 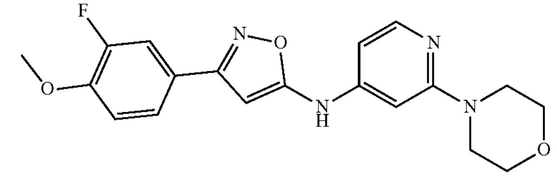 [SMILES: COc1ccc(-c2cc(Nc3ccnc(N4CCOCC4)c3)on2)cc1F] | >10 | 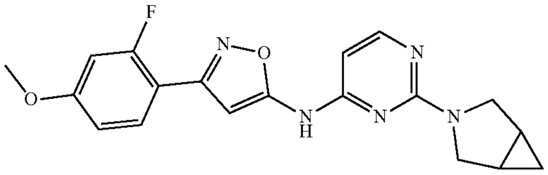 [SMILES: COc1ccc(-c2cc(Nc3ccnc(N4CC5CC5C4)n3)on2)c(F)c1] | |
| 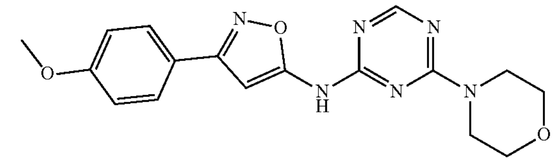 [SMILES: COc1ccc(-c2cc(Nc3ncnc(N4CCOCC4)n3)on2)cc1] | 125 | 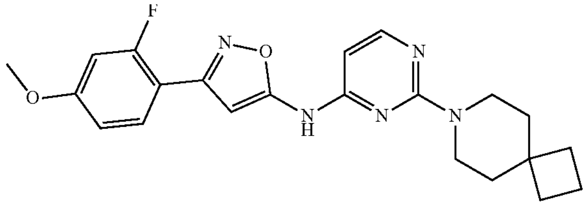 [SMILES: COc1ccc(-c2cc(Nc3ccnc(N4CCC5(CCC5)CC4)n3)on2)c(F)c1] | |
| 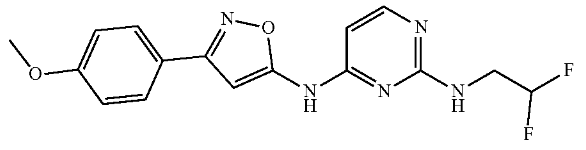 [SMILES: COc1ccc(-c2cc(Nc3ccnc(NCC(F)F)n3)on2)cc1] | 110 | 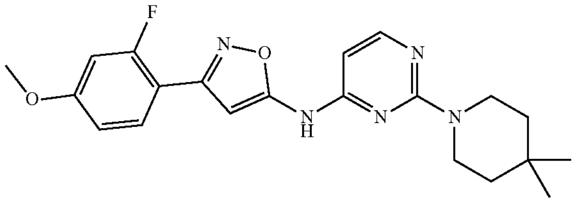 | |

-continued
| | JIMT-1 | | JIMT-1 |
|---|---|---|---|
| 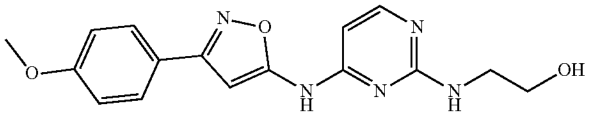 [SMILES: COc1ccc(-c2cc(Nc3ccnc(NCCO)n3)on2)cc1] | 172 | 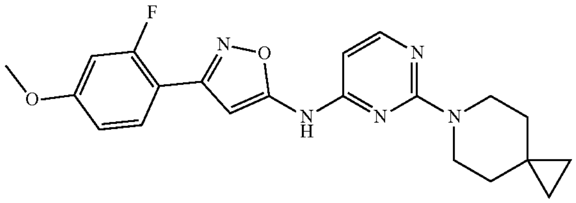 [SMILES: COc1ccc(-c2cc(Nc3ccnc(N4CCC5(CC4)CC5)n3)on2)c(F)c1] | |
| 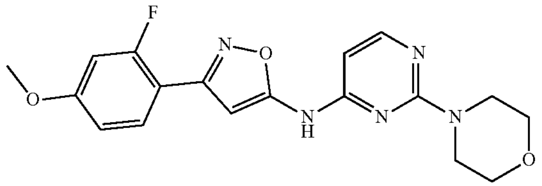 [SMILES: COc1ccc(-c2cc(Nc3ccnc(N4CCOCC4)n3)on2)c(F)c1] | 0.051 | 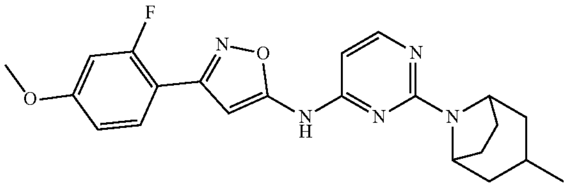 | |
| 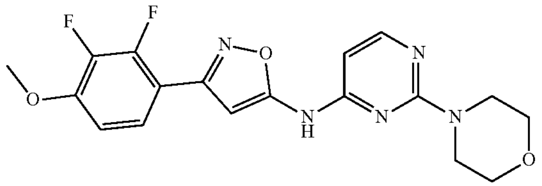 [SMILES: COc1ccc(-c2cc(Nc3ccnc(N4CCOCC4)n3)on2)c(F)c1F] | 77.9 | 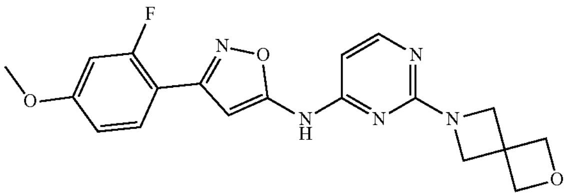 [SMILES: COc1ccc(-c2cc(Nc3ccnc(N4CC5(COC5)C4)n3)on2)c(F)c1] | |
| 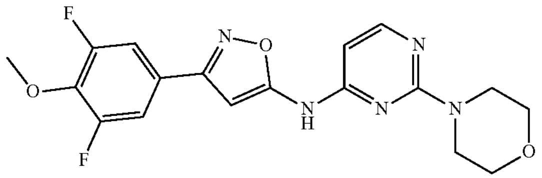 [SMILES: COc1c(F)cc(-c2cc(Nc3ccnc(N4CCOCC4)n3)on2)cc1F] | 22.9 | 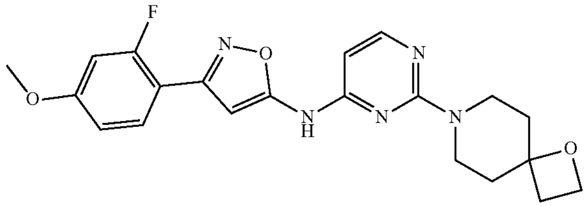 [SMILES: COc1ccc(-c2cc(Nc3ccnc(N4CCC5(CCO5)CC4)n3)on2)c(F)c1] | |
| 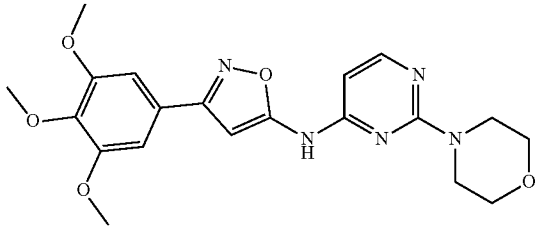 [SMILES: COc1cc(-c2cc(Nc3ccnc(N4CCOCC4)n3)on2)cc(OC)c1OC] | 0.4 | 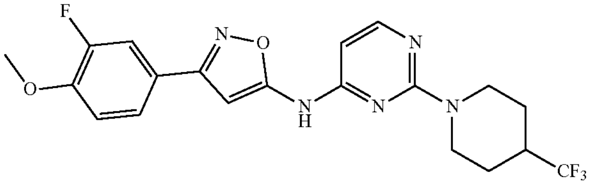 [SMILES: COc1ccc(-c2cc(Nc3ccnc(N4CCC(C(F)(F)F)CC4)n3)on2)cc1F] | 0.121 |

-continued
| | JIMT-1 | | JIMT-1 |
|---|---|---|---|
| 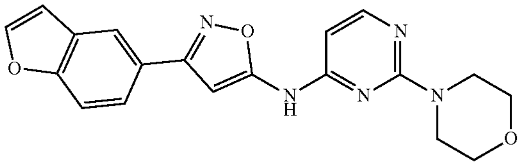 [SMILES: c1cc(Nc2cc(-c3ccc4occc4c3)no2)nc(N2CCOCC2)n1] | 0.4 | 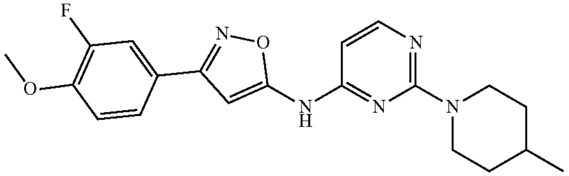 | 0.032 |
| 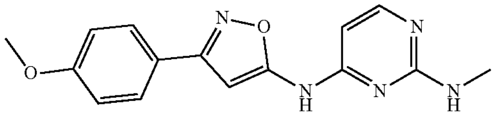 | 3.54 | 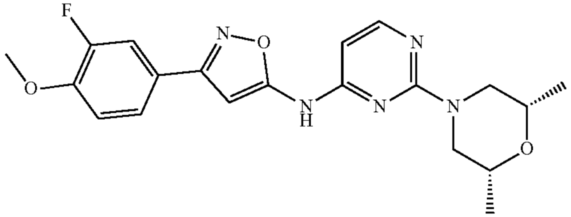 | 0.122 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. A compound of formula I:

(I)

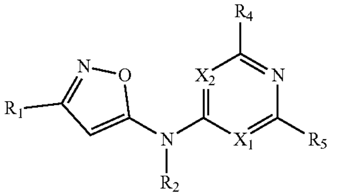

or a pharmaceutically acceptable salt thereof, wherein $X_1$ is N or $CR_6$;

$X_2$ is N or $CR_3$;

$R_1$ is aryl;

$R_2$ is H or alkyl;

$R_3$, $R_4$ and $R_6$ are each independently H, alkyl, alkenyl, alkynyl, halo, hydroxyl, carboxyl, acyl, acetyl, ester, thioester, alkoxy, phosphoryl, amino, amide, cyano, nitro, azido, alkylthio, cycloalkyl, or sulfonamide;

$R_5$ is heterocyclyl; and provided that the compound is not

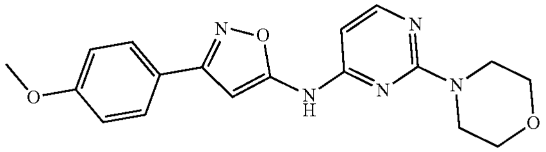 [SMILES: COc1ccc(-c2cc(Nc3ccnc(N4CCOCC4)n3)on2)cc1]

pharmaceutically acceptable salt thereof.

2. The compound of claim 1, wherein $R_1$ is aryl.

3. The compound of claim 1, wherein $R_1$ is substituted with alkyl, alkenyl, alkynyl, halo, hydroxyl, carboxyl, acyl, acetyl, ester, thioester, alkoxy, phosphoryl, amino, amide, cyano, nitro, azido, alkylthio, cycloalkyl, alkylsulfonyl, or sulfonamide.

4. The compound of claim 1, wherein $R_1$ is substituted with alkyl, alkyloxy, alkylthio, aralkyloxy, hydroxyl, halo, or amino.

5. The compound of claim 1, wherein $R_2$ is H.

6. The compound of claim 1, wherein $R_3$ is H or halo.

7. The compound of claim 1, wherein $R_5$ is a nitrogen containing heterocyclyl and the nitrogen is directly bonded to the aryl or heteroaryl ring bearing the $R_4$ substituent.

8. The compound of claim 1, wherein the compound is selected from:

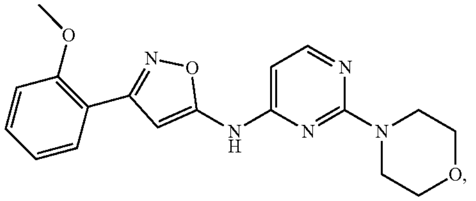

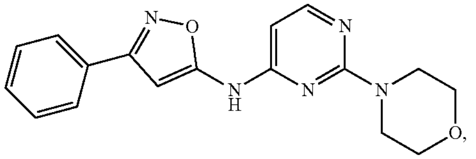

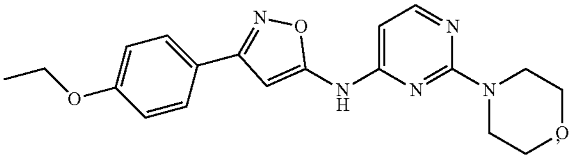

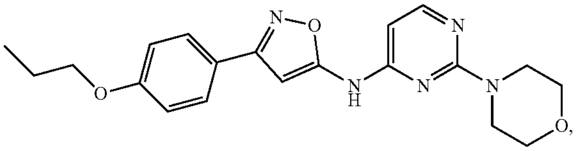

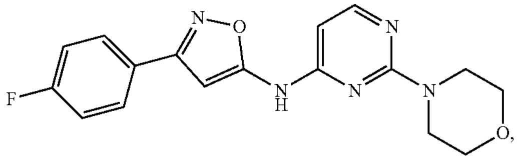

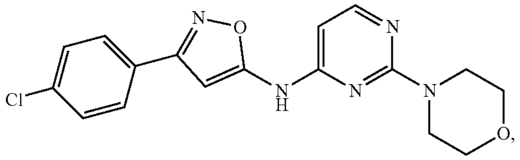

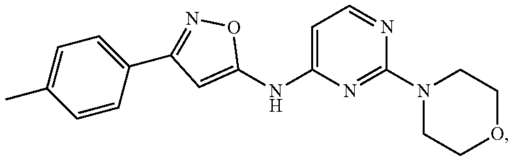

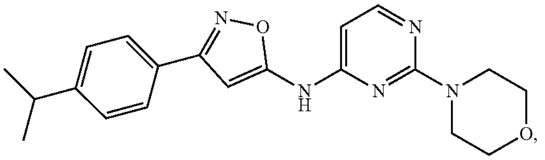

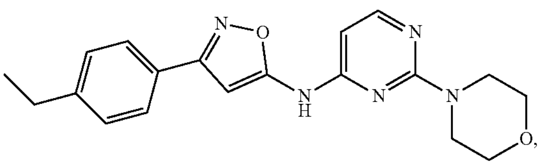

-continued
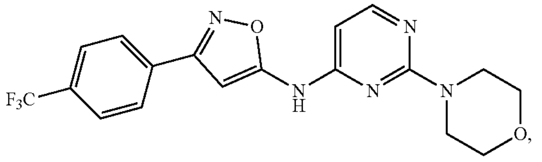
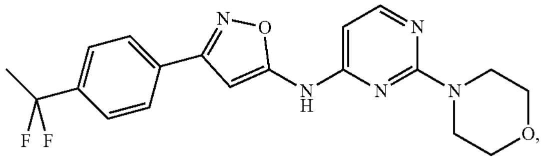
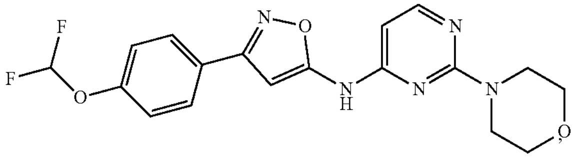
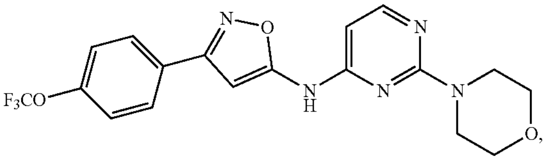
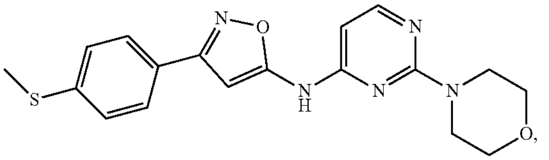
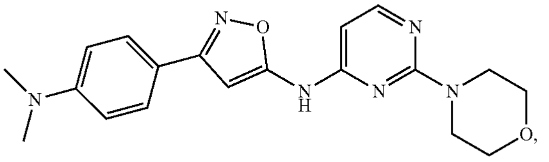
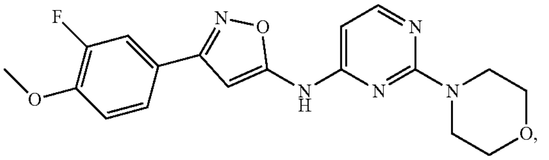
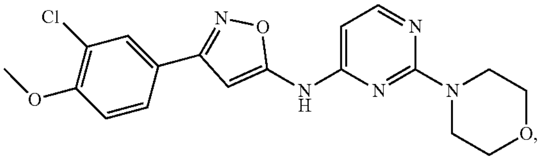
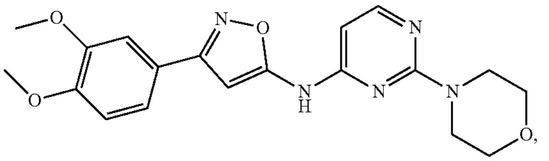
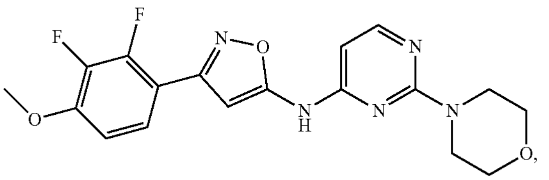
-continued
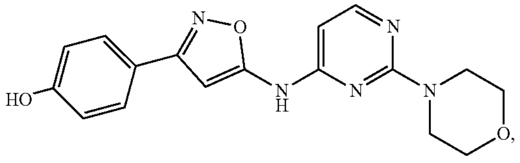
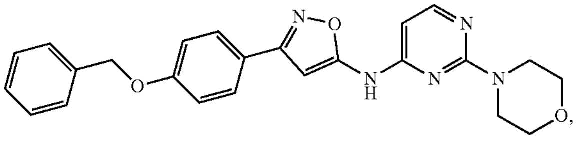
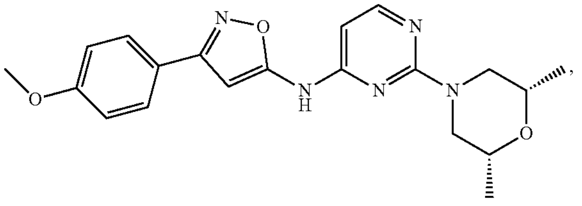
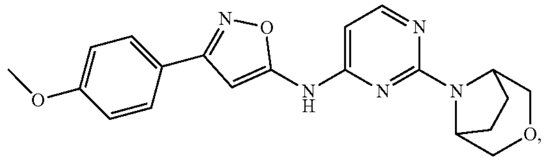
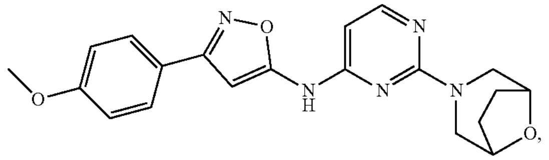
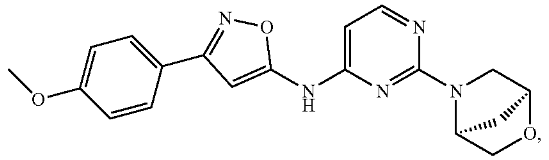
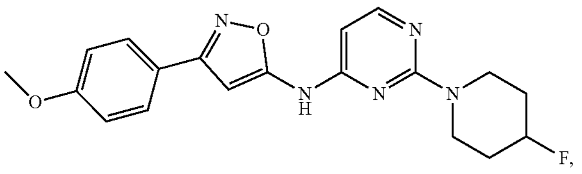
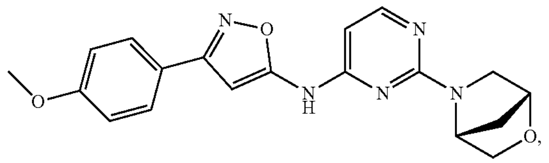
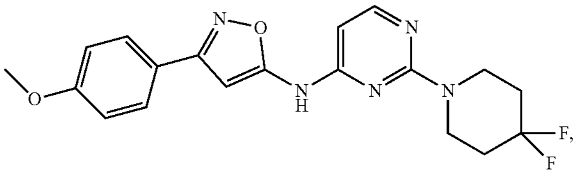
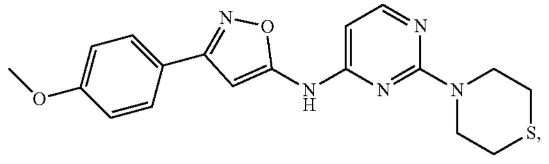

-continued
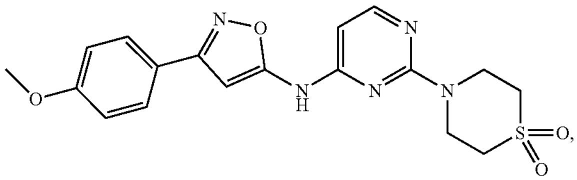,
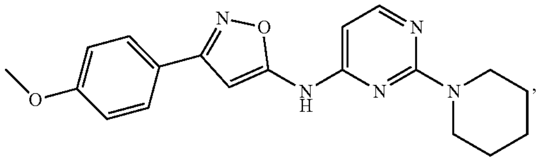,
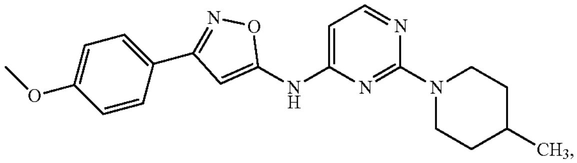,
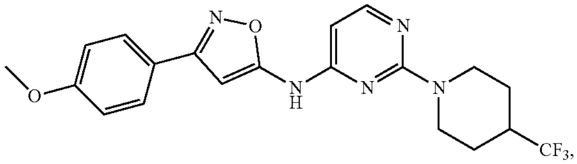,
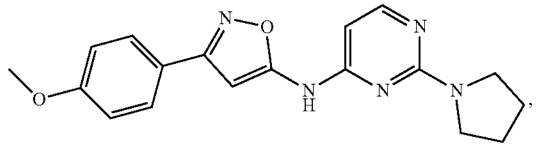,
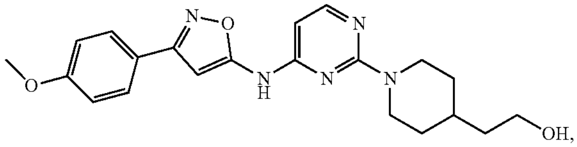,
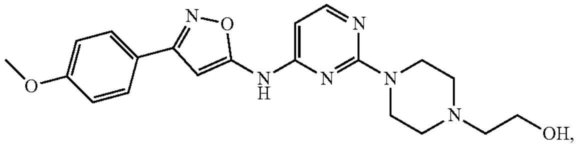,
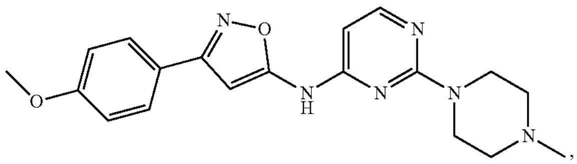,
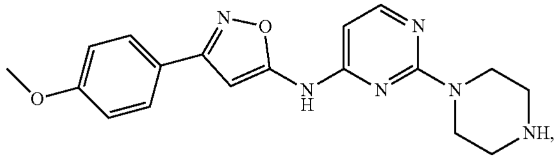,
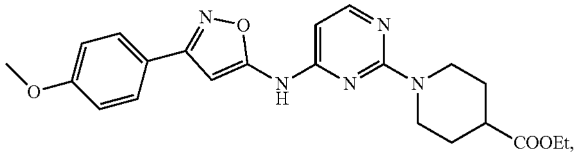,
-continued
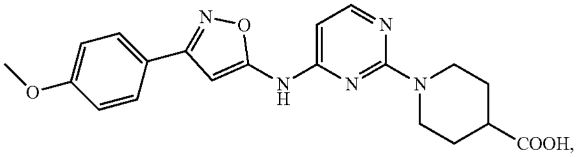,
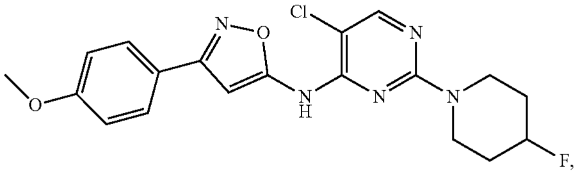,
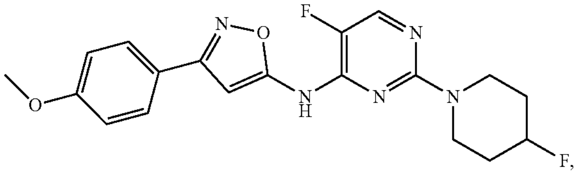,
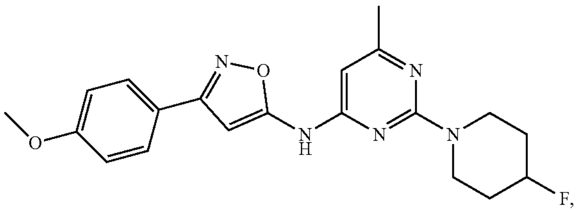,
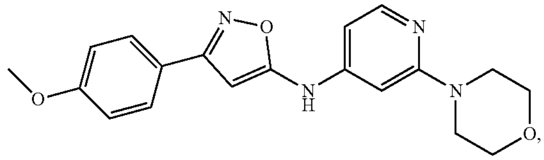,
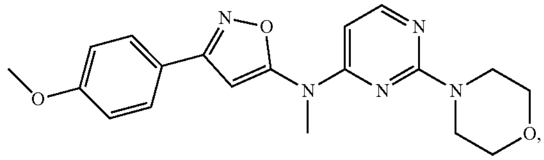,
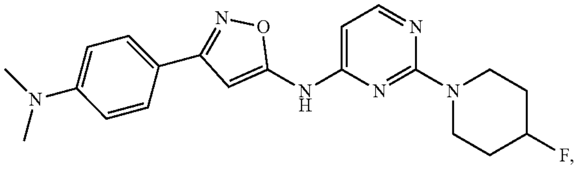,
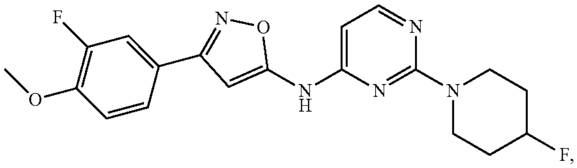,
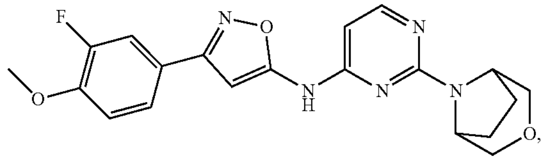,
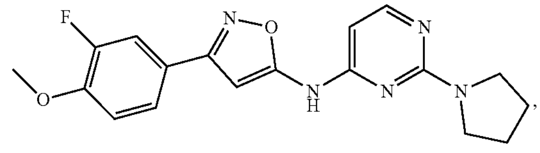, -continued
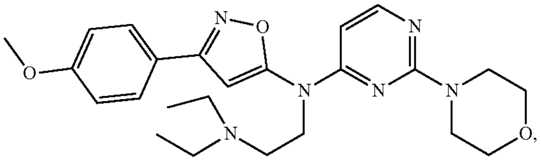,
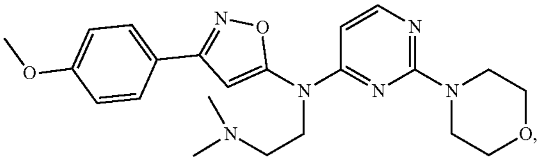,
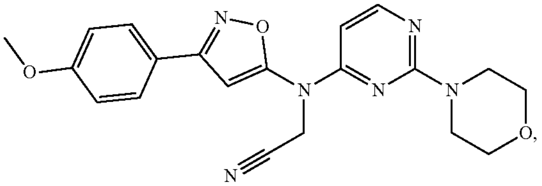,
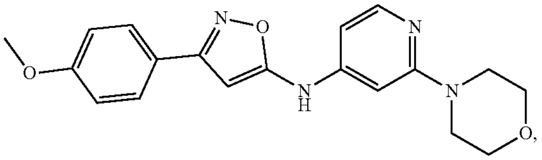,
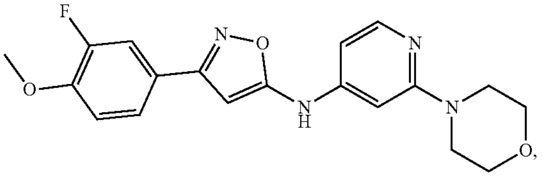,
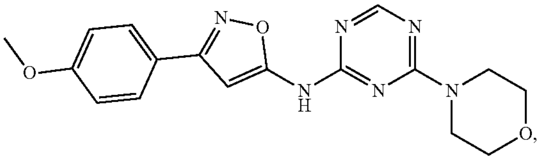,
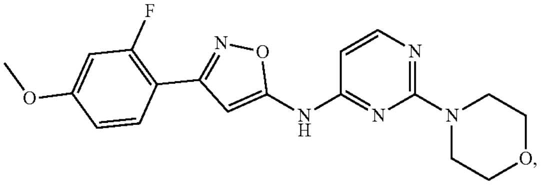,
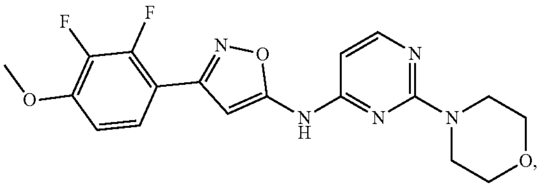,
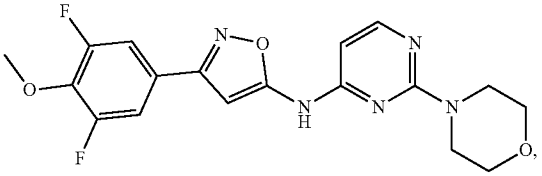,
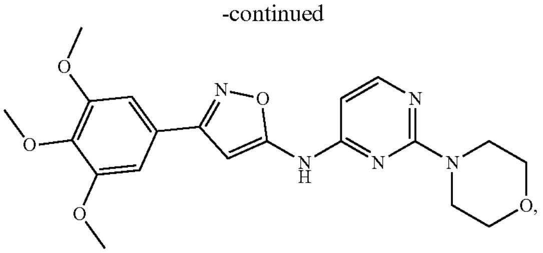,
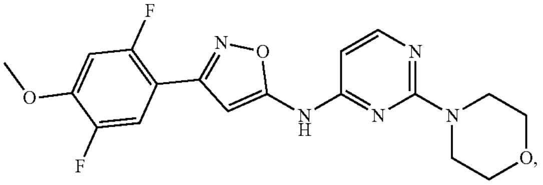,
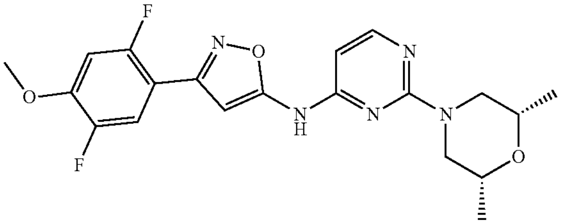,
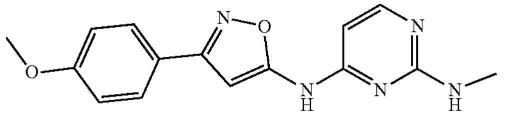,
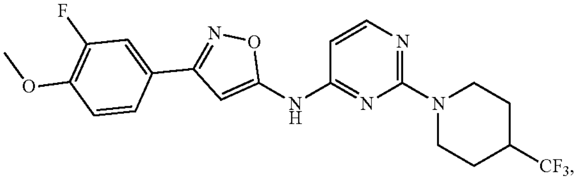,
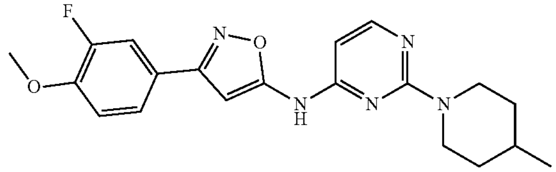,
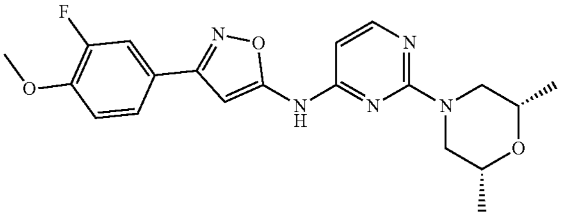,
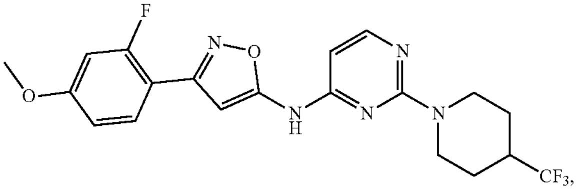,
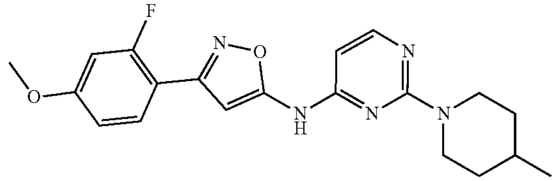, -continued
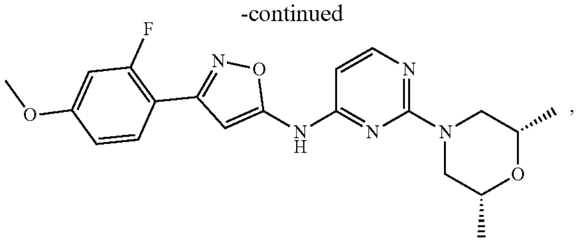
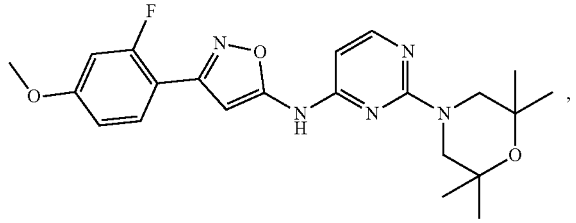
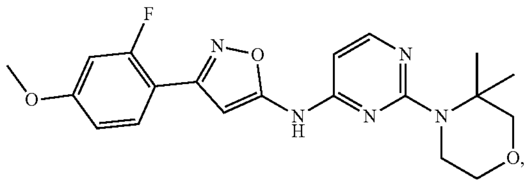
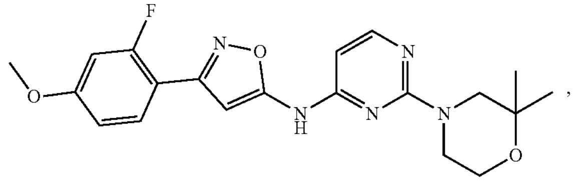
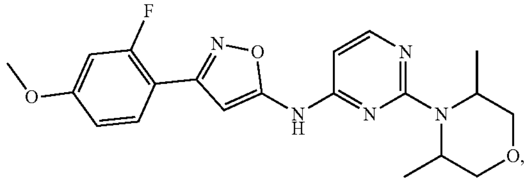
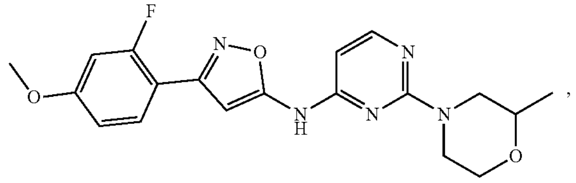
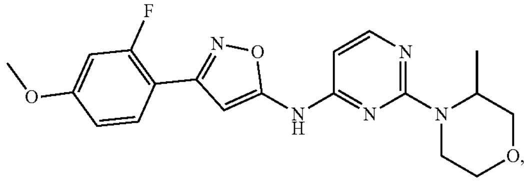
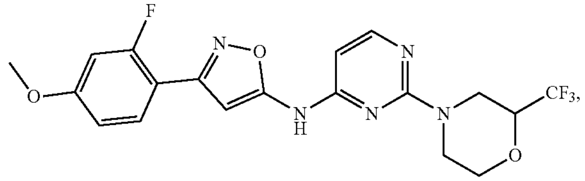
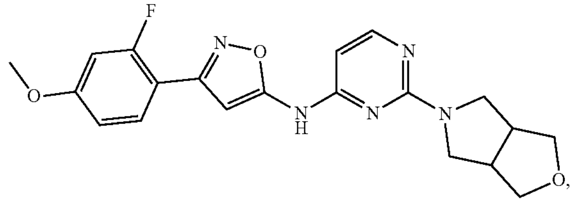
-continued
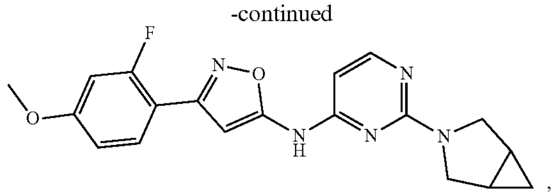
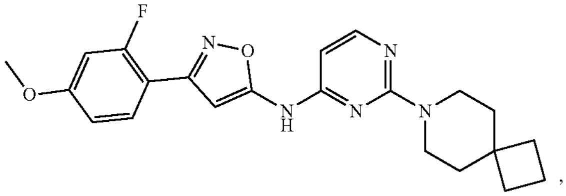
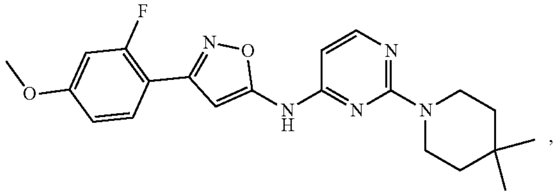
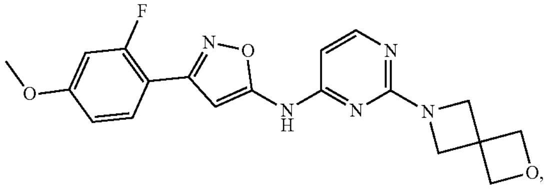
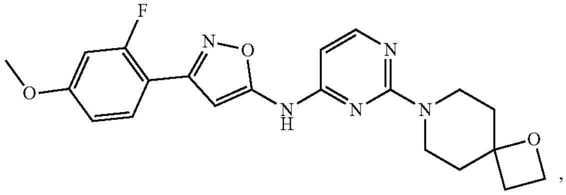
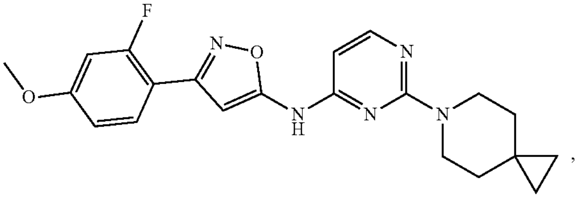
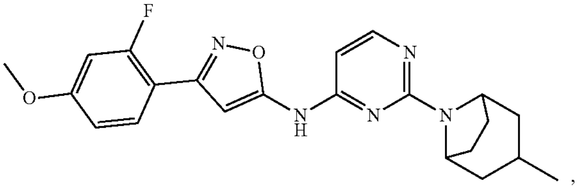
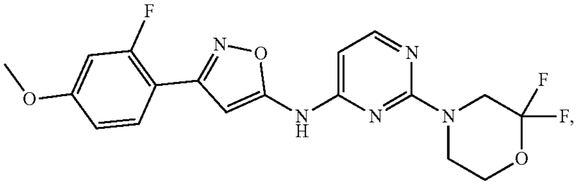
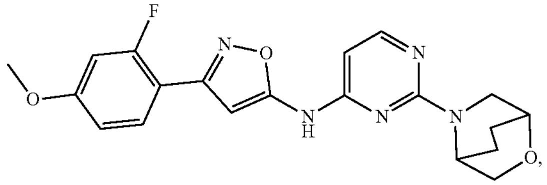

-continued
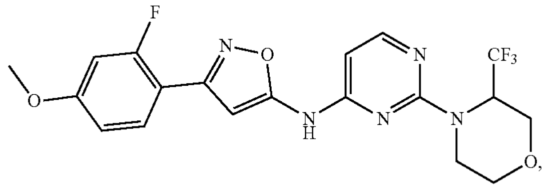
,
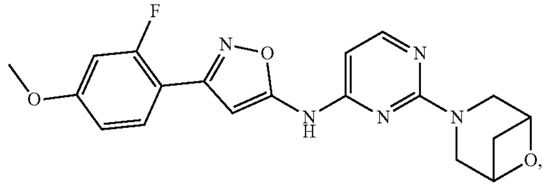
,
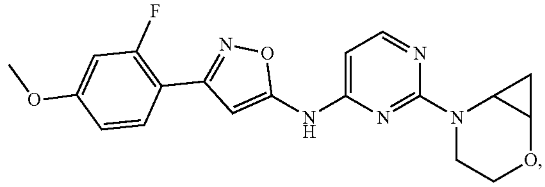
,
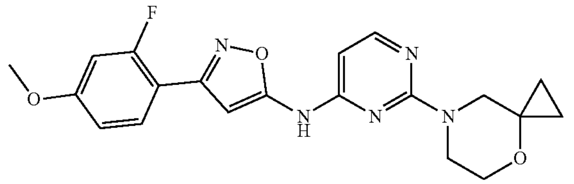
,
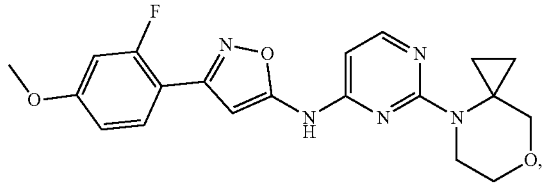
,
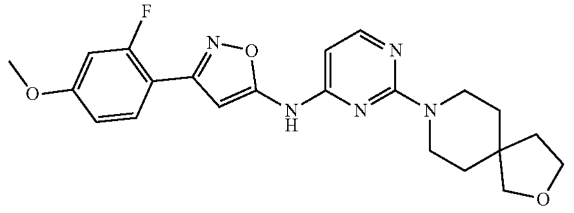
,
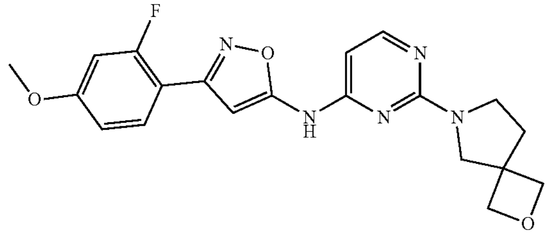
,
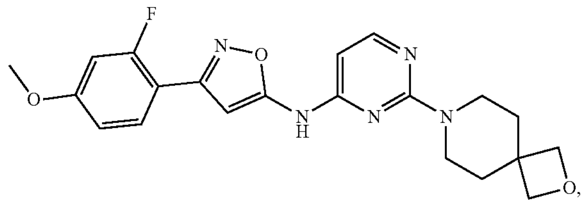
,
-continued
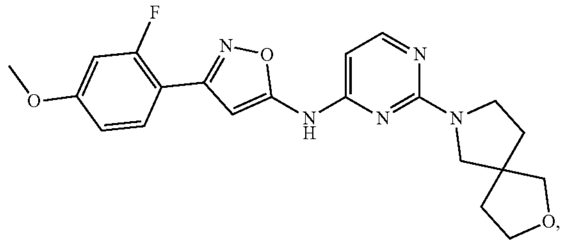
,
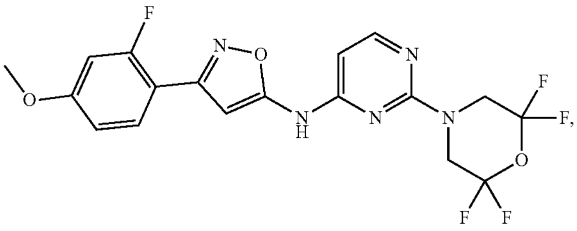
,
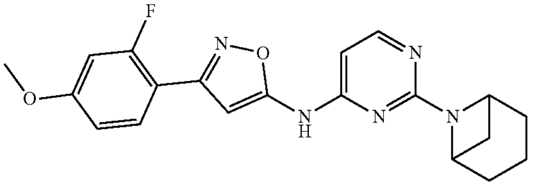
,
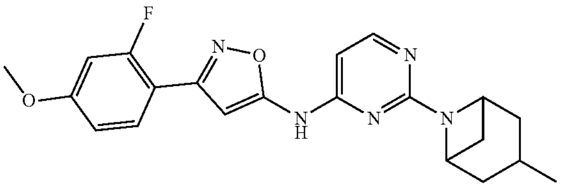
,
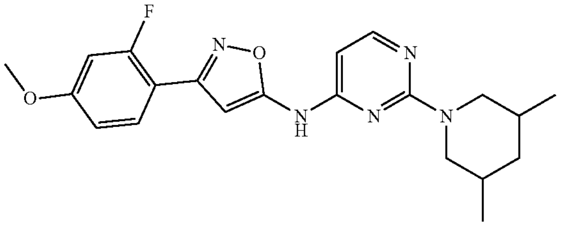
,
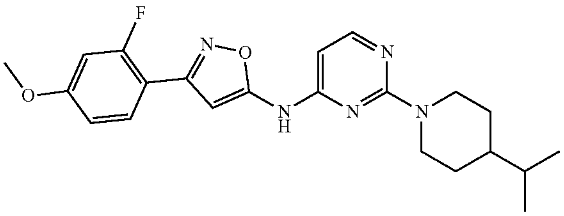
,
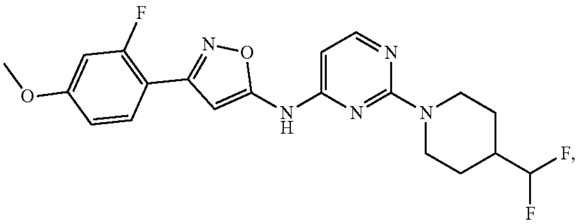
, -continued
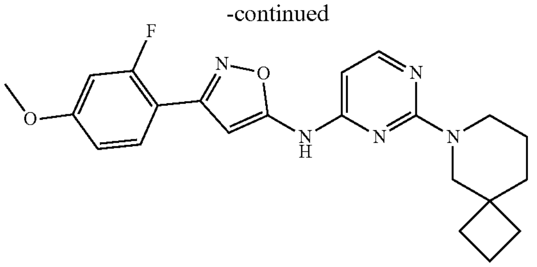
,
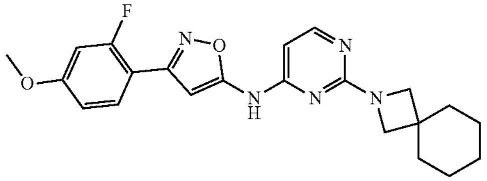
, and
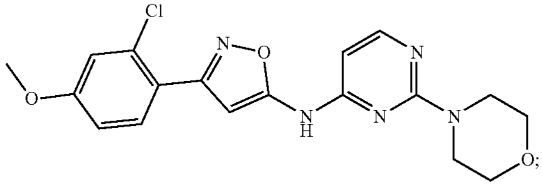
;
or a pharmaceutically acceptable salt thereof.
9. A pharmaceutical composition comprising a compound of claim 1 and a pharmaceutically acceptable excipient.
10. The compound of claim 1, wherein $X_1$ is N.
11. The compound of claim 1, wherein $X_2$ is $CR_3$.
* * * * *